US011434526B2

(12) United States Patent
Ismagilov et al.

(10) Patent No.: US 11,434,526 B2
(45) Date of Patent: *Sep. 6, 2022

(54) ENHANCED NUCLEIC ACID IDENTIFICATION AND DETECTION

(71) Applicant: CALIFORNIA INSTITUTE OF TECHNOLOGY, Pasadena, CA (US)

(72) Inventors: Rustem F. Ismagilov, Altadena, CA (US); Bing Sun, Shandong (CN); Jesus Rodriguez Manzano, Pasadena, CA (US); Eugenia Khorosheva, South Pasadena, CA (US); Matthew S. Curtis, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 299 days.

This patent is subject to a terminal disclaimer.

(21) Appl. No.: 16/224,617

(22) Filed: Dec. 18, 2018

(65) Prior Publication Data

US 2019/0352705 A1    Nov. 21, 2019

Related U.S. Application Data

(63) Continuation of application No. 15/030,202, filed as application No. PCT/US2014/060977 on Oct. 16, 2014, now Pat. No. 10,196,684.

(60) Provisional application No. 61/893,051, filed on Oct. 18, 2013, provisional application No. 61/943,784, filed on Feb. 24, 2014, provisional application No. 61/968,191, filed on Mar. 20, 2014, provisional application No. 61/993,183, filed on May 14, 2014, provisional application No. 62/063,293, filed on Oct. 13, 2014.

(51) Int. Cl.

| | | |
|---|---|---|
| *C12Q 1/68* | (2018.01) | |
| *C12Q 1/6848* | (2018.01) | |
| *C12Q 1/6844* | (2018.01) | |
| *C12Q 1/6851* | (2018.01) | |
| *C12Q 1/686* | (2018.01) | |
| *C12Q 1/6865* | (2018.01) | |
| *C12Q 1/70* | (2006.01) | |

(52) U.S. Cl.
CPC ........... *C12Q 1/6848* (2013.01); *C12Q 1/686* (2013.01); *C12Q 1/6844* (2013.01); *C12Q 1/6851* (2013.01); *C12Q 1/6865* (2013.01); *C12Q 1/707* (2013.01)

(58) Field of Classification Search
None
See application file for complete search history.

(56) References Cited

U.S. PATENT DOCUMENTS

| | | |
|---|---|---|
| 5,854,033 A | 12/1998 | Lizardi |
| 6,410,278 B1 | 6/2002 | Notomi et al. |
| 7,618,776 B2 | 11/2009 | Lizardi |
| 9,040,239 B2 | 5/2015 | Zheng et al. |
| 9,121,061 B2 | 9/2015 | Vaisvila et al. |
| 9,200,260 B2 | 12/2015 | Correa, Jr. et al. |
| 9,267,117 B2 | 2/2016 | Guan et al. |
| 9,415,392 B2 | 8/2016 | Ismagilov et al. |
| 9,447,461 B2 | 9/2016 | Ismagilov et al. |
| 9,464,319 B2 | 10/2016 | Ismagilov et al. |
| 9,803,237 B2 | 10/2017 | Ismagilov et al. |
| 9,808,798 B2 | 11/2017 | Ismagilov et al. |
| 9,822,356 B2 | 11/2017 | Ismagilov et al. |
| 9,873,907 B2 * | 1/2018 | Zeiner ............... C12Q 1/6806 |
| 10,196,684 B2 * | 2/2019 | Ismagilov ............ C12Q 1/686 |
| 2004/0265897 A1 | 12/2004 | Lizardi |
| 2007/0190531 A1 | 8/2007 | Mitani et al. |
| 2008/0293589 A1 | 11/2008 | Shapero |
| 2009/0092967 A1 * | 4/2009 | Yao ..................... C12Q 1/6844 435/6.12 |
| 2012/0196330 A1 * | 8/2012 | Nelson ................ C12Q 1/6858 435/91.2 |
| 2012/0264132 A1 | 10/2012 | Ismagilov et al. |
| 2012/0322058 A1 | 12/2012 | Regan |
| 2012/0329038 A1 * | 12/2012 | Ismagilov ............ B01F 5/0085 435/5 |
| 2016/0288121 A1 | 10/2016 | Ismagilov et al. |
| 2017/0152553 A1 | 6/2017 | Ismagilov et al. |

FOREIGN PATENT DOCUMENTS

| | | | |
|---|---|---|---|
| EP | 2371951 A1 | 10/2011 | |
| EP | 3058100 A2 | 8/2016 | |
| WO | 2004/009849 A1 | 1/2004 | |
| WO | 2010/091111 A1 | 8/2010 | |
| WO | WO-2010091111 A1 * | 8/2010 | ........... C12Q 1/6844 |
| WO | 2010/117620 A2 | 10/2010 | |
| WO | 2011/067378 A1 | 6/2011 | |
| WO | 2012/016357 A1 | 2/2012 | |
| WO | 2012/109500 A2 | 8/2012 | |

(Continued)

OTHER PUBLICATIONS

Joneja et al. Linear nicking endonuclease-mediated strand displacement DNA amplification. Anal Biochem., vol. 414(1), p.*

Kargar, M., et al. Loop-mediated isothermal amplification assay for rapid detection of Hepatitis C virus. Indian J Virol., vol. 23(1), p. 18-23, 2012.*

Bickle, TA., et al., "Biology of DNA Restriction", *Microbial. Rev.*, Jun. 1993; vol. 57, No. 2 :434-450. 18 Pages.

Boulet, GA, et al., "Nucleic acid sequence-based amplification assay for human papillomavirus mRNA detection and typing: evidence for DNA amplification," *J Clin Micro biol.* Jul. 2010 48(7): 2524-9. 7 Pages.

(Continued)

*Primary Examiner* — Suryaprabha Chunduru
(74) *Attorney, Agent, or Firm* — Steinfl + Bruno LLP

(57) ABSTRACT

The present invention relates to assays, including amplification assays, conducted in the presence of modulators. These assays can be used to detect the presence of particular nucleic acid sequences. In particular, these assays can allow for genotyping or other genetic analysis.

19 Claims, 47 Drawing Sheets

Specification includes a Sequence Listing.

(56) References Cited

FOREIGN PATENT DOCUMENTS

| WO | 2013/159116 A1 | 10/2013 |
| WO | 2014/055963 A1 | 4/2014 |
| WO | 2014/172688 A1 | 10/2014 |
| WO | 2015/009967 A1 | 1/2015 |
| WO | 2015/058008 A2 | 4/2015 |

OTHER PUBLICATIONS

Chen, F., et al., "Recognition of an expanded genetic alphabet by type-II restriction endonucleases and their application to analyze polymerase fidelity," Nucl. Acids Res. 39 (9)3949-3961.2011. 14 Pages.

Chen, F., et al., "Reconstructed evolutionary adaptive paths give polymerases accepting reversible terminators for sequencing and SNP detection," Proc. Natl. Acad. Sci. USA4107 (5) 1948-1953. 2010. 7 Pages.

Choi, et al., "Peptide nucleic acid-based array for detecting and genotyping human papillomaviruses," J. Clin Microbial, 2009, 47(6): 1785-1790. 7 Pages.

Christian, et al., "Targeting DNA double-strand breaks with TAL effector nucleases," Genetics186, 757-61. 2010. 14 Pages.

Communication Pursuant to Article 94(3) from Examining Division for EP Patent Application No. 14853582.6 filed on Oct. 16, 2014, dated Mar. 12, 2020. 6 pages.

Communication Pursuant to Article 94(3) from Examining Division for EP Patent Application No. 14853582.6 filed on Oct. 16, 2014, dated Mar. 20, 2019. 7 pages.

Cong, L., et al., "Multiplex genome engineering using CRISPR/Cas systems," Science 2013 339 (6121): 819-823. 7 Pages.

Craw, P., et al., "Isothermal nucleic acid amplification technologies for point-of-care diagnostics: a critical review," Lab on a Chip, 12, 2469-2486. 2012. 19 Pages.

D. J. Alexander, An Overview of the Epidemiology of Avian Influenza, Vaccine, 2007, 25, 30:5637-44. Abstract Only. 2 pages.

Donis-Keller, et al., "Site-specific enzymatic cleavage of RNA," Nucleic Acids Res., 7(1): 179-92. 1979. 15 Pages.

Du, W. B., et al.,. "SlipChip." Lab Chip9, 2286-2292, 2009. 8 Pages.

European Patent Office; Extended European Search Report and Opinion. EP Patent Application No. 14853582.6 filed on filed Oct. 16, 2014, dated Mar. 21, 2017. 7pages.

Fan et al., "Non-Invasive prenatal measurement of the fetal genome" Nature 487, 320-324, 2012. 9 Pages.

Fan, H. C., et al., "Noninvasive diagnosis of fetal aneuploidy by shotgun sequencing DNA from maternal blood." Proc. Natl. Acad. Sci., U.S.A. 105, 42, 16266-16271, 2008. 7 Pages.

Fan, H. C., et al., "Microfluidic digital PCR enables rapid prenatal diagnosis of fetal aneuploidy." Am. J. Ob. Gynecol. 200, 543.e1-543.e7, 2009. 8 Pages.

Feng Sehn, et al., "Digital PCR on a SlipChip" LabChip 10: 2666-2672. 2010. 9 Pages.

Feng Shen et al., "Digital Isothermal Quantification of Nucleic Acids via Simultaneous Chemical Initiation of Recombinase Polymerase Amplification Reactions on SlipChip" Analytical Chemistry, 2011. 83:3533-3540.

Feng Shen, et al., "Multiplexed Quantification of Nucleic Acids with large Dynamic Range Using Multivolume Digital RT-PCR on a rotational SlipChip tested with HIV and Hepatitis C Viral Load" JACS 133: 17705-17712. 2011. 9 pages.

Feng Shen, et al., "Nanoliter Multiplex PCR Arrays on a SlipChip" Analytical Chemistry, 82: 4606-4612. 2010. 8 Pages.

Fraser, et al., "Structural and Mechanistic insights into Hepatitis C viral translation initiation" Nature Reviews Microbiology.5: 29-38. 2007. 11 Pages.

Gansen, et al., "Digital LAMP in a sample self-digitization (SD) chip." Lab Chip12, 2247-2254. 2012. 9 pages.

Heyries, K., et al., "Megapixel digital PCR". Nat. Methods8, 8, 649-651, 2011. 6 Pages.

Hoshika, S., et al., "Artificial Genetic Systems: Self-Avoiding DNA in PCR and Multiplexed PCR," Angew. Chem. Int. Ed.49 (32) 5554-5557, 2010. 5 Pages.

Hoshika, S., et al., "Self-Avoiding Molecular Recognition Systems (SAMRS)," Nucleic Acids Symp. Series. No. 52 (1) 129-130. 2008. 4 Pages.

International Search Report for International Application No. PCT/US14/60977 filed on Oct. 16, 2014 on behalf of California Institute of Technology, dated Apr. 23, 2015. 7 pages . . . .

International Preliminary Report on Patentability for International Application No. PCT/US2014/060977 filed on Oct. 16, 2014 on behalf of California Institute of Technology, dated Apr. 19, 2016. 10 pages . . . .

Johnson, V.A., et al., "Update of the Drug Resistance Mutations in HIV-1," Mar. 2013, Topics in Antiviral Medicine, vol. 21, Issue 1:6-14. 10 Pages.

Joneja et al., "Linear nicking endonuclease-mediated strand displacement DNA amplification," Anal Biochem, Jul. 2011, vol. 414, No. 1, pp. 58-69. 13 Pages.

Kaihatsu, et al., "Rapid Identification of Swine-Origin Influenza A Virus by Peptide Nucleic Acid Chromatography", Antivirals & Antiretrovirals, 5(4): 077-079, 2013. 4 Pages.

Kaneko H, Kawana T, Fukushima E, and Suzutani T, "Tolerance of loop-mediated isothermal amplification to a culture medium and biological substances", J. Biochem., Biophys. Methods, 70: 499-501 (2007).

Kargar, M., et al., "Loop-Mediated Isothermal Amplification Assay for Rapid Detection of Hepatitis C virus," Indian J Virol. Jun. 2012; 23(1): 18-23. 7 Pages.

Kasarjian, JKA.,et al., "Four new type I restriction enzymes identified in Escherichia coli clinical isolates", Nucleic Acids Res. 2005; 33(13): e114, 9 Pages.

Kim, et al., "Genotyping with CRISPR-Cas-derived RNA guided endonucleases," Nat Common. 5, 3157. 2014. 9 Pages.

Landry, M. L., "Diagnostic tests for influenza infection", Curr Opin Pediatr, 2011,23: 91-97. 8 Pages.

Laos, R., et al. "Directed Evolution of Polymerases To Accept Nucleotides with Nonstandard Hydrogen Bond Patterns," Biochemistry 2013, 52, 5288-5294. 8 pages.

Lartillot, N., et al., "PhyloBayes 3: A Bayesian software package for phylogenetic reconstruction and molecular dating", Bioinformatics, 2009, vol. 25, No. 17, 2286-2288. 4 pages.

Leconte, A.M., et al., "Directed evolution of DNA polymerases for next-generation sequencing," Angew. Chem. Int. Ed., 2010. 49:5921-5924. 5 Pages.

Li, CM, et al., "Cell type specific over-expression of chromosome 21 genes in fibroblasts and fetal hearts with trisomy 21," BMC Medical Genetics 2006, 7: 24. 16 Pages.

Li, L., et al., "Natural-like replication of an unnatural base pair for the expansion of the genetic alphabet and biotechnology applications," J. Am. Chem. Soc., 2014. 136:826-829. 5 pages.

Li, Z., et al., "Site-specifically arraying small molecules or proteins on DNA using an expanded genetic alphabet," Chem. Eur. J.,19:14205-14209. Issue 42, Oct. 2013. 6 Pages.

Liu, K., et al., "SATe-II: very fast and accurate simultaneous estimation of multiple sequence alignments and phylogenetic trees", Syst Biol, Advance access publication Dec. 2011, 61(1): 90-106. 18 Pages.

Liu, W., et al., "SlipChip for Immunoassays in Nanoliter Volumes," Anal. Chem. vol. 82, No. 8, 3276-3282, 2010. 8 Pages.

Lo., YMD, et al., "Plasma placental RNA allelic ratio permits noninvasive prenatal chromosomal aneuploidy detection," Nat. Med. 2007, vol. 13, No. 2, 218-223. 7 pages.

Lo, YMD, et al., "Presence of fetal DNA in maternal plasma and serum," Lancet350, 485-487. 1997. 4 Pages.

Machado, M., et al., "Phred-Phrap package to analyses tools: a pipeline to facilitate population genetics re-sequencing studies", Investig Genet, 2011, 2, 3. 8 Pages.

Mali, et al., "RNA-guided human genome engineering via Cas 9," Science, 339: 823-826. 2013. 6 Pages.

Mali, P., et al., "Cas9 as a versatile tool for engineering biology," Nat Methods, 2013, 10(10): 957-963. 8 Pages.

(56) References Cited

OTHER PUBLICATIONS

Malyshev, D.A., et al., "Efficient and sequence-independent replication of DNA containing a third base pair establishes a functional six-letter genetic alphabet," *Proc. Natl. Acad. Sci. USA*, 2012 vol. 109, No. 30:12005-12010. 7 Pages.

Mani, N., et al., "Clinically Relevant HCV Drug Resistance Mutations Figures and Tables," from HCV Phenotype Working Group, HCV Drug Development Advisory Group, Ann Forum Collab HIV Res. vol. 14 (2): 2012; 1-10. 9 Pages.

Munster, V. J., et al., "Spatial, temporal, and species variation in the prevalence of influenza A viruses in wild migratory birds," PLoS Pathog, 2007, vol. 3, Issue 5, e61, 0630-0638. 10 Pages.

Non-Final Office Action for U.S. Appl. No. 15/030,202, filed Apr. 18, 2016 on behalf of California Institute of Technology, dated Mar. 8, 2018. 16 pages . . . .

Notice of Allowance for U.S. Appl. No. 15/030,202, filed Apr. 18, 2016 on behalf of California Institute of Technology, dated Sep. 14, 2018. 7 pages . . . .

Orozovic, G., et al., "Detection of Resistance Mutations to Antivirals Oseltamivir and Zanamivir in Avian Influenza A Viruses Isolated from Wild Birds,". PLoS ONE. Jan. 6, 2011. vol. 6(1): e16028. doi: 10.1371/journal.pone.0016028. 11 Pages.

Orum et al., "Single base pair mutation analysis by PNA directed PCR clamping" Nucleic Acids Res 1993, 21 (23): 5332-5336. 5 Pages.

Ottesen, E. A., et al., "Microfluidic digital PCR enables multigene analysis of individual environmental bacteria". Science 314 (5804), 1464-1467, 2006. 6 Pages.

Pellicelli, A M., et al., "HCV genotype 1a shows a better virological response to antiviral therapy than HCV genotype 1b," BMC Gastroenterol. Nov. 16, 2012; 12:162. 8 Pages.

Posada, D., "jModelTest: phylogenetic model averaging," *Mol Biol Evol*, 2008, 25(7): 1253-1256. 5 Pages.

Qian et al., "Scaling up Digital Circuit Computation with DNA Strand Displacement Cascades", *Science*; vol. 332: 1196-1201. 2011. 8 Pages.

Ray, et al., "Peptide nucleic acid (PNA): its medical and biotechnical applications and promise for the future" *FASEB*, J, vol. 14:1041-1060. 2000. 21 pages.

Selck, D.A., et al., "Increased Robustness of Single-Molecule Counting with Microfluidics, Digital Isothermal Amplification, and a Mobile Phone versus Real-Time Kinetic Measurements," *Analytical Chemistry*, 2013. 85:11129-11136. 9 Pages.

Seo , Y.J., "Site-specific labeling of DNA and RNA using an efficiently replicated and transcribed class of unnatural base pairs," J. Am. Chern. Soc. 2011, 133:19878-19888. 12 Pages.

Shalem, O., et al., "Genome-scale CRISPR-Cas9 knockout screening in human cells," Science 2014, vol. 343(6166): 84-87. 6 Pages.

Sherlock Biosciences: Better Diagnostic Testing Should be Elementary. An Overview. Downloaded from the web at: https://sherlock.bio/technology/ on Oct. 7, 2020. 6 Pages.

Silva, et al., "Meganucleases and other tools for targeted genome engineering: perspectives and challenges for gene therapy," Curr Gene Ther., 11: 11-27. 2011. 19 Pages.

Smith et al., Mutation detection with MutH, MutL, and MutS mismatch repair proteins Proc Natl Acad Sci, 1996, vol. 93(9): 4374-4379. 7 pages.

Stamatakis, "RAxML version 8: a tool for phylogenetic analysis and post-analysis of large phylogenies," Bioinformatics 2014, vol. 30, No. 9, pp. 1312-1313. doi: 10.1093/bioinformatics/btu033.

Summons to attend oral proceedings pursuant to Rule 115(1) EPC for EP Application No. 14853582.6 filed on Oct. 16, 2014 on behalf of California Institute of Technology, dated Jul. 6, 2021. 10 pages.

Sun, B., et al., "Measuring Fate and Rate of Single-Molecule Competition of Amplification and Restriction Digestion, and Its Use for Rapid Genotyping Tested with Hepatitis C Viral RNA" Genotype Determination, Angew. Chem. Int. Ed. 2014, 53, 8088-8092. 6 Pages.

Sun, B., et al., "Mechanistic evaluation of the pros and cons of digital RT-LAMP for HIV-1 viral load quantification on a microfluidic device and improved efficiency via a two-step digital protocol". Anal Chem 85(3):1540-1546. 2013. 8 pages.

Tatsumi, et al., "Rapid Screening assay for KRAS mutations by the modified smart amplification process," J Mol Diagn 2008, 10(6): 520-526. 8 Pages.

Thorsen, T., et al., "Microfluidic large-scale integration". *Science* 288, 580-584, 2002. 6 Pages.

Tong, Yanhong et al. "Multiple strategies to improve sensitivity, speed and robustness of isothermal nucleic acid amplification for rapid pathogen detection", BMC Biotechnology, Biomed Central Ltd, vol. 11, No. 1, May 11, 2011, p. 50. 7 pages.

Tsongalis et al., "Branched DNA technology in Molecular Diagnostics," *Am J Clin Pathol* 2006; 126: 448-453. 7 Pages.

Tsugunori Notomi, et al., "Loop-mediated isothermal amplification of DNA", Nucleic Acids Res. vol. 28(12). E63. Jun. 15, 2000. 8 Pages.

Urnov et al., "Highly efficient endogenous human gene correction using designed zinc-finger nucleases", Nature, 2005. vol 435: 646-651.

U.S. Appl. No. 61/516,628, filed Apr. 5, 2011 on behalf of Rustem Ismagilov.

U.S. Appl. No. 61/518,601, filed May 9, 2011 on behalf of Rustem Ismagilov.

U.S. Appl. No. 61/611,295, filed Mar. 25, 2012 on behalf of Romualdas Vaisvila.

U.S. Appl. No. 61/722,968, filed Nov. 6, 2012 on behalf of Yu Zheng.

U.S. Appl. No. 61/723,427, filed Nov. 7, 2012 on behalf of Ivan Correa.

U.S. Appl. No. 61/724,041, filed Nov. 8, 2012 on behalf of Shengxi Guan.

U.S. Appl. No. 62/038,036, filed Aug. 15, 2014 on behalf of Stefano Begolo.

U.S. Appl. No. 61/340,872 filed on behalf of Rustem F. Ismagilov, filed Mar. 22, 2010. 589 pages.

U.S. Appl. No. 61/162,922 filed on behalf of Rustem F. Ismagilov, filed Mar. 24, 2009. 89 pages.

U.S. Appl. No. 61/262,375 filed on behalf of Rustem F. Ismagilov, filed Nov. 18, 2009. 130 pages.

Wang, et al., "A one-step reverse transcription loop-mediated isothermal amplification for detection and discrimination of infectious bursal disease virus" Virol J, 2011. vol 8, No. 108. pp. 1-7. Especially p. 2 col. 2 para 2, p. 3 col. 1 para 1, p. 3 fig 1 A, p. 4col. 2 para 2, p. 5 col. 2 para 1, p. 5 fig 3. 8 Pages.

Wang, QQ, et al., "Rapid detection of hepatitis C virus RNA by a reverse transcription loop-mediated isothermal amplification assay," FEMS Immunol Med Microbial, 2011, Oct.; 63(1):144-147. 6 Pages.

Wang, T., et al., "Genetic screens in human cells using the CRISPR-Cas9 System," *Science* 2014, 343(6166): 80-84. 7 Pages.

Wegrzyn, J. L., et al., "PineSAP-sequence alignment and SNP identification pipeline", *Bioinformatics*, 2009, vol. 25, No. 19, 2609-2610. 2 Pages.

Weisinger, R. M., et al., "Mesofluidic Devices for DNA-Programmed Combinatorial Chemistry," *PLOS ONE* 2012; 7 (3), e32299. 9 Pages.

Weisinger, R. M., et al., "Highly Parallel Translation of DNA Sequences into Small Molecules," PLOS ONE 2012; 7 (3), e28056. 8 Pages.

Written Opinion for International Application No. PCT/US14/60977 filed on Oct. 16, 2014 on behalf of California Institute of Technology, dated Apr. 23, 2015. 9 pages . . . .

Yang J, et al.,, "Detection of hepatitis C virus by an improved loop-mediated isothermal amplification assay." *Arch Virol*. Aug. 2011;156(8):1387-1396.11 Pages.

Yang, Z., et al., "Conversion strategy using an expanded genetic alphabet to assay nucleic acids," Anal. Chem. 85(9): 4705-4712. 2013. 9 Pages.

Yang, Z., et al., "Enzymatic incorporation of a third nucleobase pair," Nucl. Acids Res. 35 (13) 4238-4249. 2007. 13 Pages.

Yang, Z., et al., "Expanded Genetic Alphabets in the Polymerase Chain Reaction," *Angew. Chem. Int. Ed*.49 (1)177-180. 2010. 5 Pages.

(56) References Cited

OTHER PUBLICATIONS

Decision of Refusal for EP Application No. 14853582.6 filed Oct. 16, 2014 on behalf of California Institute of Technology dated Apr. 7, 2022. 12 pages.
Decision to Refuse a European Patent Application for EP Application No. 14853582.6 filed Oct. 16, 2014 on behalf of California Institute of Technology dated May 18, 2022. 9 pages.

* cited by examiner

FIG. 24A
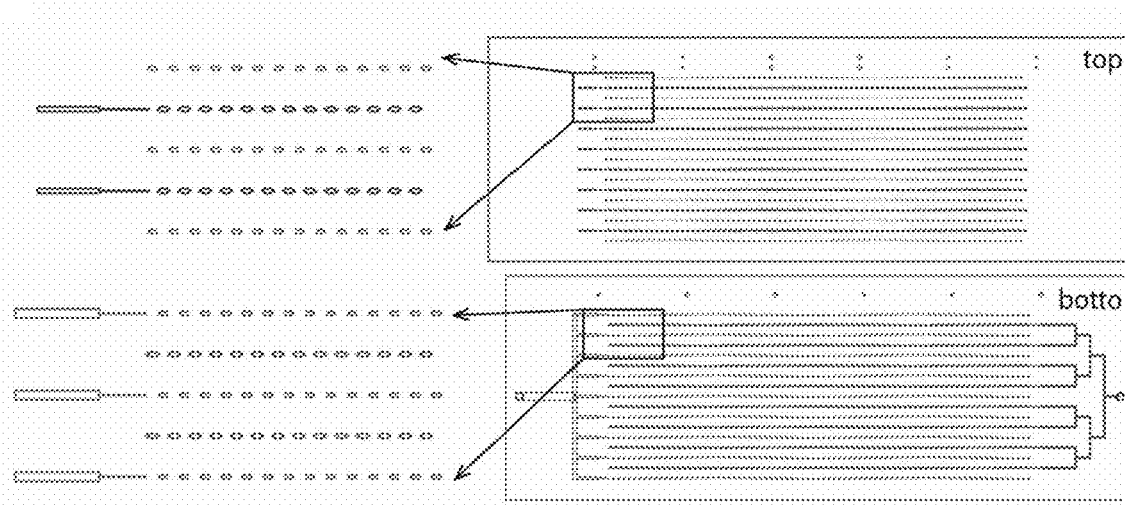
FIG. 24B
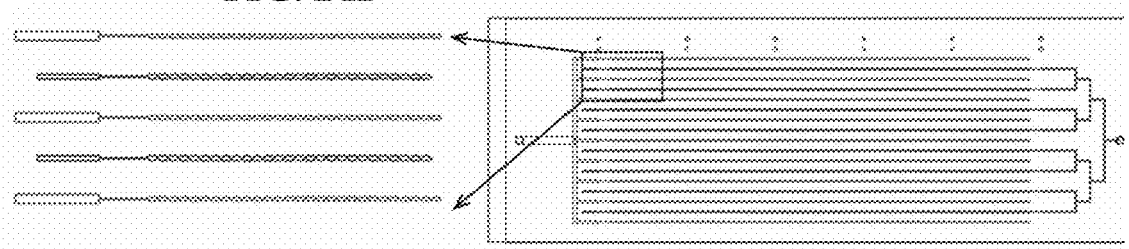
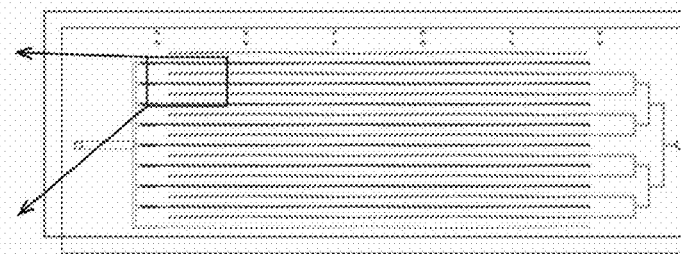
FIG. 24C

FIG. 32A
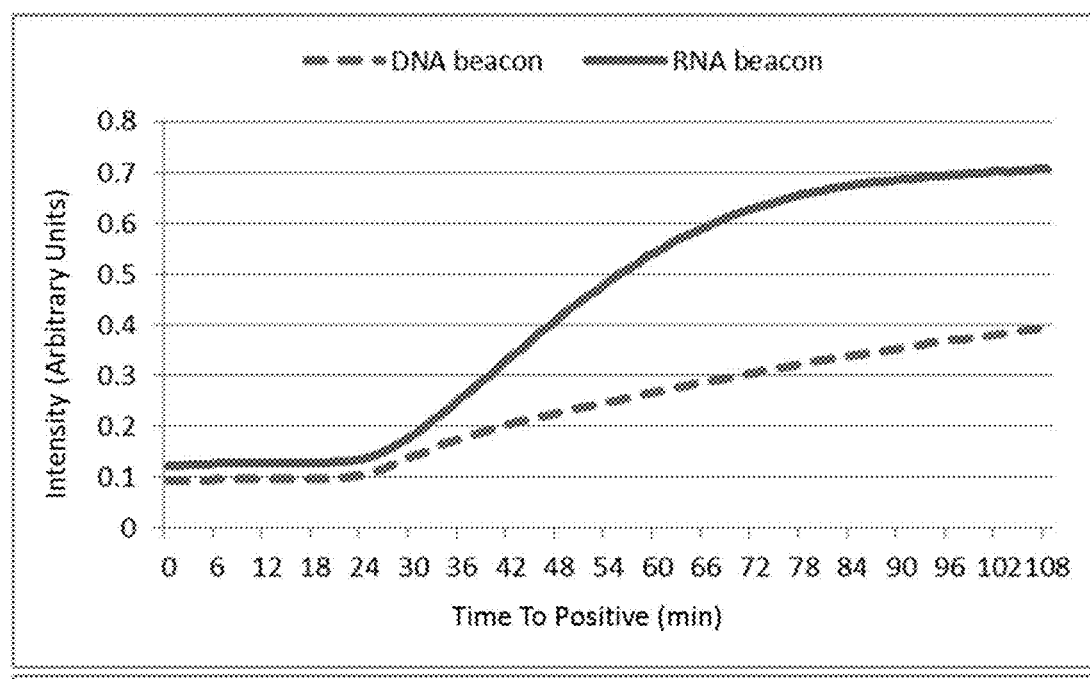
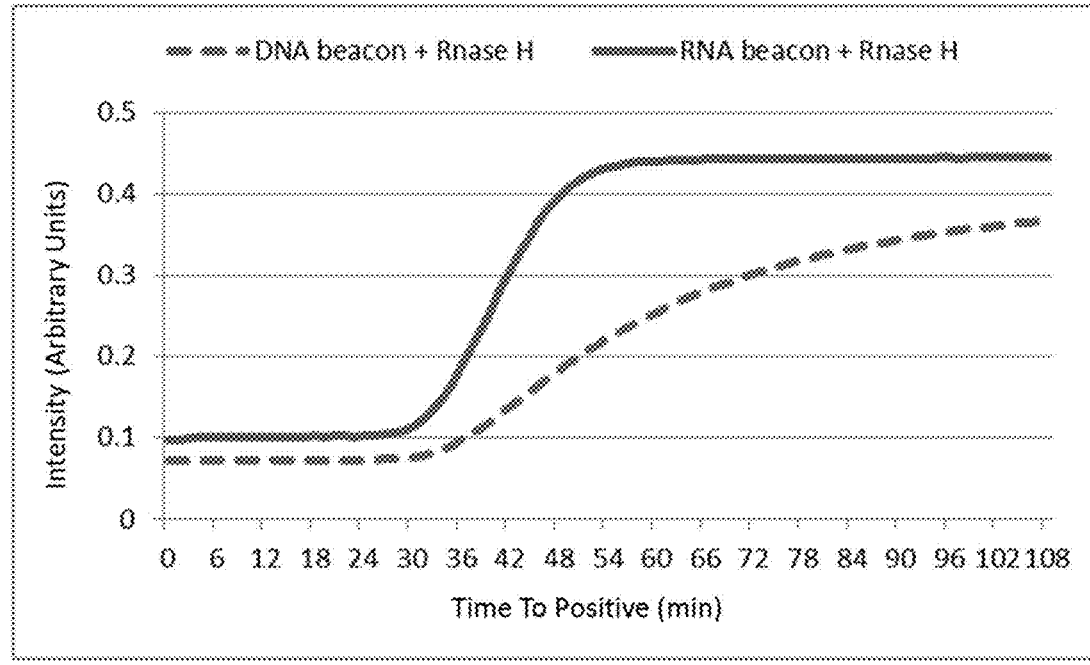
FIG. 32B

FIG. 33A
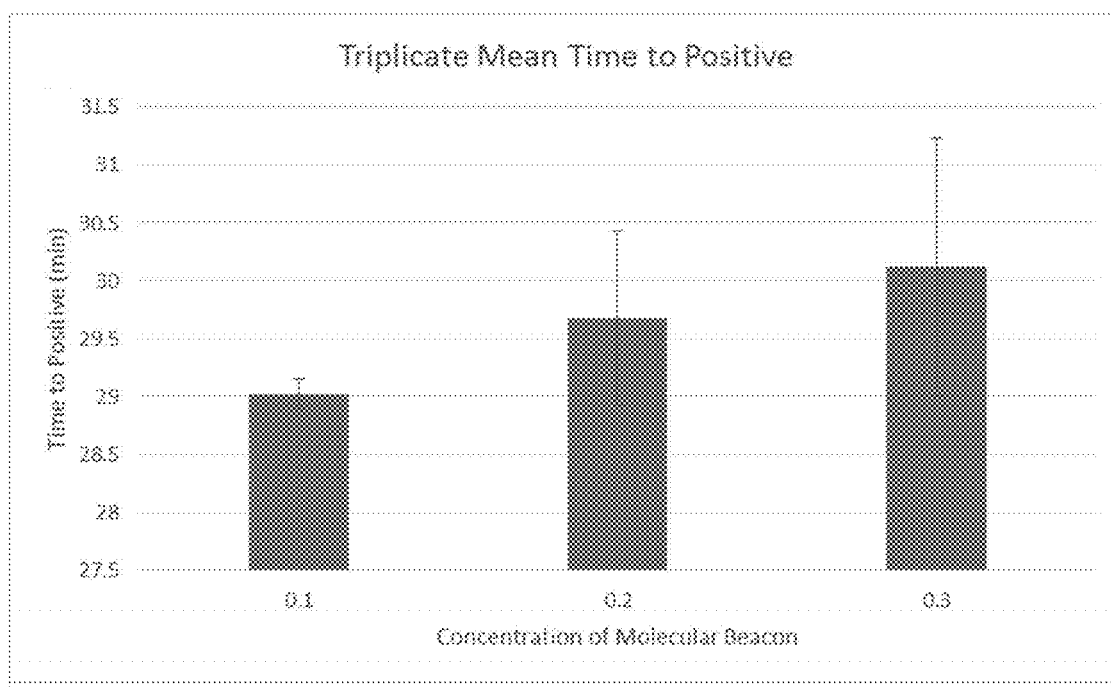
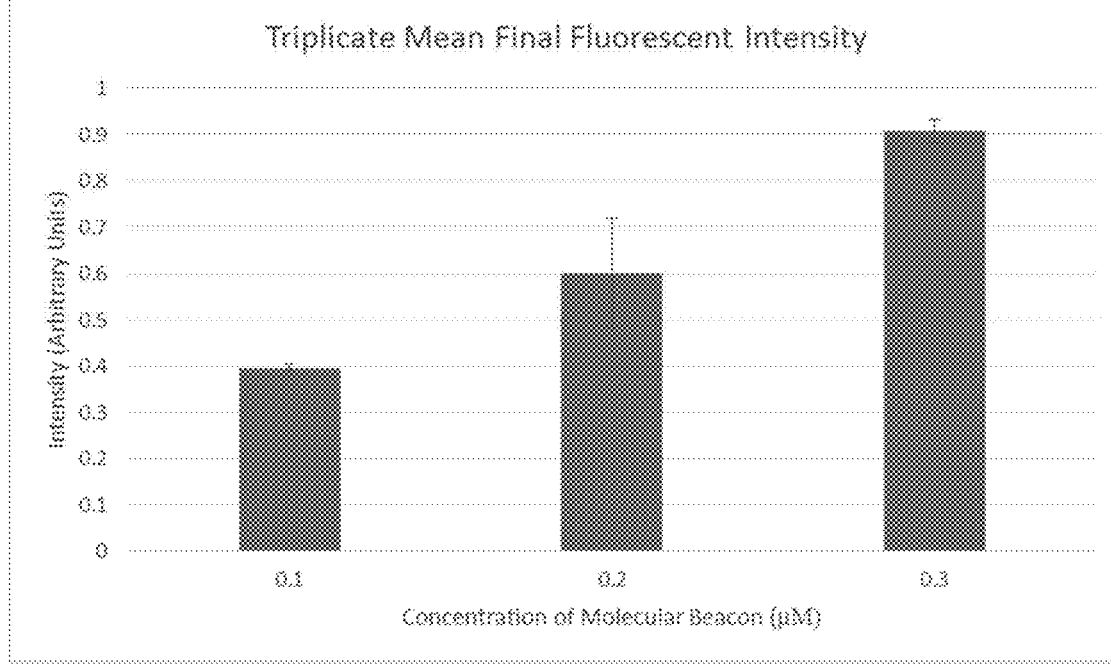
FIG. 33B

FIG. 34A
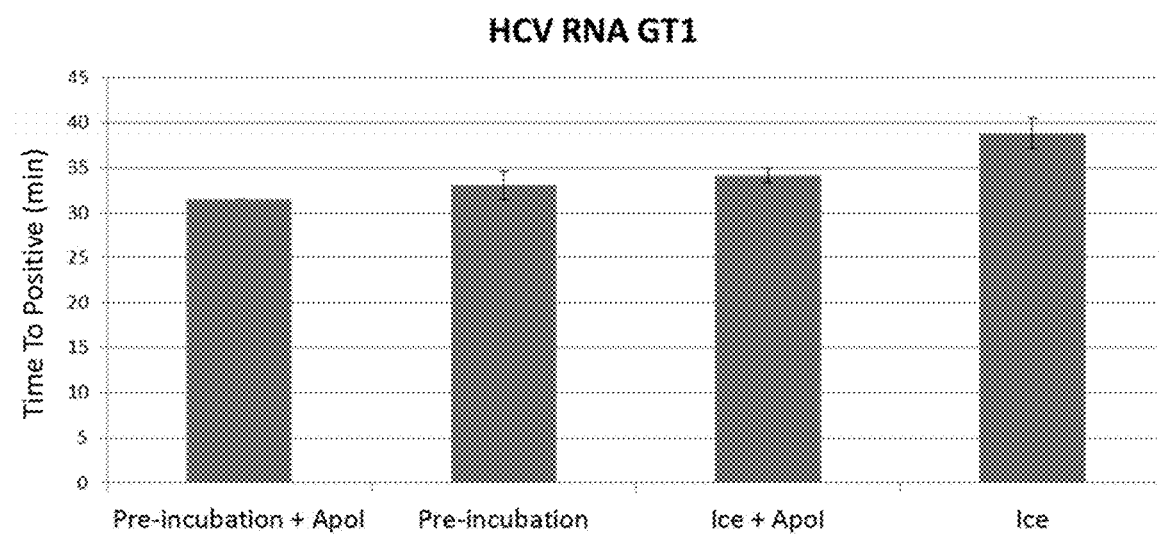
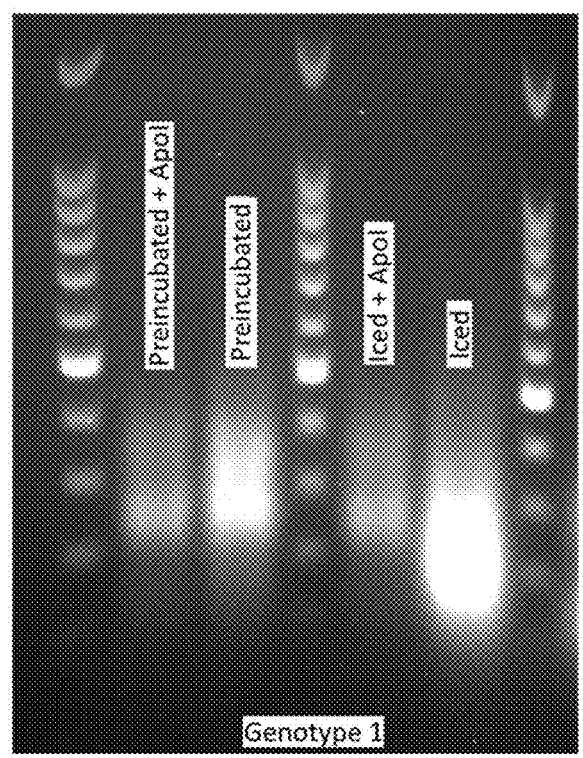
FIG. 34B

SEQUENCE LISTING

<160> NUMBER OF SEQ ID NOS: 101

<210> SEQ ID NO 1
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aattctaata cgactcacta tagggcaagc accctatcag gcagta                    46

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gtctagccat ggcgttagta                                                 20

<210> SEQ ID NO 3
<211> LENGTH: 37
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' FAM
<220> FEATURE:
<223> OTHER INFORMATION: 3' BHQ1

<400> SEQUENCE: 3
cgatcgagcc atagtggtct gcggaaccgg tcgatcg                              37

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
aatctccagg cagtgtcgcc                                                 20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gaccggacat agagtaaatt                                                 20

<210> SEQ ID NO 6
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
cggggcactc gcaagcaccc tatcaggcag taccacaagg cctttcgcga cccaactgat    60

<210> SEQ ID NO 7
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
cggggcactc gcaagcactc taccagacag tgccacaagg cctttcgcga cccaactgat    60

<210> SEQ ID NO 8
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
taatacgact cactataggg caagcaccct atcaggcagt a    41

<210> SEQ ID NO 9
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
taattctaat acgactcact atagggcaag caccctatca ggcagta    47

<210> SEQ ID NO 10
<211> LENGTH: 32
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' FAM
<220> FEATURE:
<223> OTHER INFORMATION: 3' BHQ1

<400> SEQUENCE: 10
cgtacggtct gcggaaccgg tgagtacgta cg    32

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
acggaggcta tgaccyggta    20

<210> SEQ ID NO 12
<211> LENGTH: 18
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 12
cttcacggag gctatgac                                                    18

<210> SEQ ID NO 13
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
aattctaata cgactcacta tagggagaag gatgttgcct agccaggart t               51

<210> SEQ ID NO 14
<211> LENGTH: 50
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(34)
<223> OTHER INFORMATION: Inosine

<400> SEQUENCE: 14
aattctaata cgactcacta tagggagaag gatnatgttg cctagccagg                 50

<210> SEQ ID NO 15
<211> LENGTH: 39
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' FAM
<220> FEATURE:
<223> OTHER INFORMATION: 3' BHQ1

<400> SEQUENCE: 15
cctgcaccag aatacgactt ggagctcata acgtgcagg                             39

<210> SEQ ID NO 16
<211> LENGTH: 39
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' FAM
<220> FEATURE:
<221> NAME/KEY: modified_base
<222> LOCATION: (18)..(18)
<223> OTHER INFORMATION: Inosine
<220> FEATURE:
<223> OTHER INFORMATION: 3' BHQ1

<400> SEQUENCE: 16
cctgcactaa catcatgntc ctccaaygtg tcgtgcagg                             39

<210> SEQ ID NO 17
<211> LENGTH: 19
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
aggacgtyaa gttcccggg                                                    19

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gatcgttggt ggagtttac                                                    19

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tcctaaacct caaagaaaaa c                                                 21

<210> SEQ ID NO 20
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
aattctaata cgactcacta tagggagaag ggccaaggrt acccgggctg                  50

<210> SEQ ID NO 21
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
aattctaata cgactcacta tagggagaag gtcrttgcca tagaggggcc                  50

<210> SEQ ID NO 22
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
aattctaata cgactcacta tagggagaag gggagccatc cygcccaccc                  50

<210> SEQ ID NO 23
<211> LENGTH: 35
<212> TYPE: DNA
```

-continued

<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' FAM
<220> FEATURE:
<223> OTHER INFORMATION: 3' BHQ1

<400> SEQUENCE: 23
cctgcaaaga cttccgagcg gtcrcaacct gcagg                                35

<210> SEQ ID NO 24
<211> LENGTH: 35
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' FAM
<220> FEATURE:
<223> OTHER INFORMATION: 3' BHQ1

<400> SEQUENCE: 24
cctgcaagga agacttccga gcggtcrcat gcagg                                35

<210> SEQ ID NO 25
<211> LENGTH: 38
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' FAM
<220> FEATURE:
<223> OTHER INFORMATION: 3' BHQ1

<400> SEQUENCE: 25
cctgcaaaga cttccgagcg gtcrcaacct cgtgcagg                             38

<210> SEQ ID NO 26
<211> LENGTH: 36
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' FAM
<220> FEATURE:
<223> OTHER INFORMATION: 3' BHQ1

<400> SEQUENCE: 26
cctgcagggt gtgcgcgcga cgaggaagac tgcagg                               36

<210> SEQ ID NO 27
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
aattctaata cgactcacta tagggaaatc tacggatagc aagttrgc                  48

<210> SEQ ID NO 28

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ccaaaggcag aagaaagtca                                                      20

<210> SEQ ID NO 29
<211> LENGTH: 32
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' FAM
<220> FEATURE:
<223> OTHER INFORMATION: 3' BHQ1

<400> SEQUENCE: 29
cgcgatggag gttaargcrg cggcgtatcg cg                                        32

<210> SEQ ID NO 30
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
aattctaata cgactcacta tagggaaact ccaagtcgta ttctggtt                       48

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
cgaccttgtc gttatctgtg a                                                    21

<210> SEQ ID NO 32
<211> LENGTH: 34
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' FAM
<220> FEATURE:
<223> OTHER INFORMATION: 3' BHQ1

<400> SEQUENCE: 32
cgcgatttca cggaggctat gactaggtat cgcg                                      34

<210> SEQ ID NO 33
<211> LENGTH: 45
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 33
aattctaata cgactcacta tagggaaatg aatgatctga ggtag          45

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ttcttctcca tcctymta          18

<210> SEQ ID NO 35
<211> LENGTH: 35
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' FAM
<220> FEATURE:
<223> OTHER INFORMATION: 3' BHQ1

<400> SEQUENCE: 35
cgcgataarg ccctrgaytg ycagatctaa tcgcg          35

<210> SEQ ID NO 36
<211> LENGTH: 49
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (42)..(42)
<223> OTHER INFORMATION: a, c, g, t, unknown or other

<400> SEQUENCE: 36
aattctaata cgactcacta tagggaaaca caacattggt anattgact          49

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ggtgaahrcc tggaaakcra a          21

<210> SEQ ID NO 38
<211> LENGTH: 36
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' FAM
<220> FEATURE:
<223> OTHER INFORMATION: 3' BHQ1

<400> SEQUENCE: 38
cgcgatcacr gtcacygaga rygayatccg atcgcg         36

<210> SEQ ID NO 39
<211> LENGTH: 36
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' FAM
<220> FEATURE:
<223> OTHER INFORMATION: 3' BHQ1

<400> SEQUENCE: 39
cgcgatcgac acccgytgyt tygactcaag atcgcg         36

<210> SEQ ID NO 40
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
aattctaata cgactcacta tagggaaaaa gtggytcaat ggagta         46

<210> SEQ ID NO 41
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
caaggatgat yctgatgac         19

<210> SEQ ID NO 42
<211> LENGTH: 35
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' FAM
<220> FEATURE:
<221> NAME/KEY: modified_base
<222> LOCATION: (17)..(17)
<223> OTHER INFORMATION: a, c, g, t, unknown or other
<220> FEATURE:
<223> OTHER INFORMATION: 3' BHQ1

<400> SEQUENCE: 42
cgcgatccct yctagcncag garcaactga tcgcg         35

<210> SEQ ID NO 43
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
aattctaata cgactcacta tagggaaagc tagaaggatg gagaar         46

```
<210> SEQ ID NO 44
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
garacagcta gacacact                                                 18

<210> SEQ ID NO 45
<211> LENGTH: 31
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' FAM
<220> FEATURE:
<223> OTHER INFORMATION: 3' BHQ1

<400> SEQUENCE: 45
gcgatcggct aggcaacatc atcatgatcg c                                  31

<210> SEQ ID NO 46
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
cctcccggga gagccatag                                                19

<210> SEQ ID NO 47
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
tccaagaaag gacccggtct ttttctgcgg aaccggtgag tac                     43

<210> SEQ ID NO 48
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gtcctggcaa ttccggt                                                  17

<210> SEQ ID NO 49
<211> LENGTH: 43
<212> TYPE: DNA
<213> ORGANISM: Artificial Sequence
<220> FEATURE:
<223> OTHER INFORMATION: Description of Artificial Sequence: Synthetic
      primer
<220> FEATURE:
```

```
<221> NAME/KEY: modified_base
<222> LOCATION: (16)..(16)
<223> OTHER INFORMATION: Inosine

<400> SEQUENCE: 49
tccaagaaag gacccngtct ttttctgcgg aaccggtgag tac                43

<210> SEQ ID NO 50
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (3)..(3)
<223> OTHER INFORMATION: Inosine
<220> FEATURE:
<221> NAME/KEY: modified_base
<222> LOCATION: (8)..(8)
<223> OTHER INFORMATION: Inosine

<400> SEQUENCE: 50
ttnccggnaa ttccggt                                             17

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
gcactcgcaa gcaccctatc                                          20

<210> SEQ ID NO 52
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ttgggcgtgc ccccgcaagt ttttcagtac cacaaggcct ttcgcgacc          49

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ctgctagccg agtagtgttg                                          20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (16)..(16)
```

<223> OTHER INFORMATION: Inosine

<400> SEQUENCE: 54
gcactcgcaa gcaccntatc                                               20

<210> SEQ ID NO 55
<211> LENGTH: 50
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (17)..(17)
<223> OTHER INFORMATION: Inosine
<220> FEATURE:
<221> NAME/KEY: modified_base
<222> LOCATION: (41)..(41)
<223> OTHER INFORMATION: Inosine
<220> FEATURE:
<221> NAME/KEY: modified_base
<222> LOCATION: (47)..(47)
<223> OTHER INFORMATION: Inosine

<400> SEQUENCE: 55
ttgggcgtgc ccccgcnaga tttttcagta ccacaaggcc nttcgcnacc              50

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (16)..(16)
<223> OTHER INFORMATION: Inosine

<400> SEQUENCE: 56
ctgctagccg agtagngttg                                               20

<210> SEQ ID NO 57
<211> LENGTH: 43
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (12)..(12)
<223> OTHER INFORMATION: Inosine
<220> FEATURE:
<221> NAME/KEY: modified_base
<222> LOCATION: (16)..(16)
<223> OTHER INFORMATION: Inosine

<400> SEQUENCE: 57
tccaagaaag gncccngtct ttttctgcgg aaccggtgag tac                     43

<210> SEQ ID NO 58
<211> LENGTH: 43
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base -continued

```
<222> LOCATION: (12)..(12)
<223> OTHER INFORMATION: Inosine
<220> FEATURE:
<221> NAME/KEY: modified_base
<222> LOCATION: (16)..(16)
<223> OTHER INFORMATION: Inosine

<400> SEQUENCE: 58
cccaagaaag gncccngtct ttttctgcgg aaccggtgag tac         43

<210> SEQ ID NO 59
<211> LENGTH: 45
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (14)..(14)
<223> OTHER INFORMATION: Inosine
<220> FEATURE:
<221> NAME/KEY: modified_base
<222> LOCATION: (18)..(18)
<223> OTHER INFORMATION: Inosine

<400> SEQUENCE: 59
tccaatggaa aggncccngt cttttctgc ggaaccggtg agtac         45

<210> SEQ ID NO 60
<211> LENGTH: 43
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (12)..(12)
<223> OTHER INFORMATION: Inosine
<220> FEATURE:
<221> NAME/KEY: modified_base
<222> LOCATION: (16)..(16)
<223> OTHER INFORMATION: Inosine

<400> SEQUENCE: 60
tccaagaaag gncccngtct ttttctgcgg aaccggtgag ttc         43

<210> SEQ ID NO 61
<211> LENGTH: 43
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (5)..(5)
<223> OTHER INFORMATION: Inosine

<400> SEQUENCE: 61
tccangaaag gacccggtct ttttctgcgg aaccggtgag tac         43

<210> SEQ ID NO 62
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
```

```
<221> NAME/KEY: modified_base
<222> LOCATION: (5)..(5)
<223> OTHER INFORMATION: a, c, g, t, unknown or other

<400> SEQUENCE: 62
accgnaattg ccaggac                                                    17

<210> SEQ ID NO 63
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (13)..(13)
<223> OTHER INFORMATION: Inosine

<400> SEQUENCE: 63
gtcctggcaa ttncggt                                                    17

<210> SEQ ID NO 64
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (10)..(10)
<223> OTHER INFORMATION: a, c, g, t, unknown or other
<220> FEATURE:
<221> NAME/KEY: modified_base
<222> LOCATION: (15)..(15)
<223> OTHER INFORMATION: a, c, g, t, unknown or other

<400> SEQUENCE: 64
accggaattn ccggnaa                                                    17

<210> SEQ ID NO 65
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (9)..(9)
<223> OTHER INFORMATION: a, c, g, t, unknown or other
<220> FEATURE:
<221> NAME/KEY: modified_base
<222> LOCATION: (12)..(12)
<223> OTHER INFORMATION: a, c, g, t, unknown or other
<220> FEATURE:
<221> NAME/KEY: modified_base
<222> LOCATION: (16)..(17)
<223> OTHER INFORMATION: a, c, g, t, unknown or other

<400> SEQUENCE: 65
accggaatng cngggnn                                                    17

<210> SEQ ID NO 66
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
```

```
<220> FEATURE:
<221> NAME/KEY: modified_base
<222> LOCATION: (1)..(2)
<223> OTHER INFORMATION: Inosine
<220> FEATURE:
<221> NAME/KEY: modified_base
<222> LOCATION: (6)..(6)
<223> OTHER INFORMATION: Inosine
<220> FEATURE:
<221> NAME/KEY: modified_base
<222> LOCATION: (9)..(9)
<223> OTHER INFORMATION: Inosine

<400> SEQUENCE: 66
nncccngcna ttccggt                                                17

<210> SEQ ID NO 67
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (9)..(9)
<223> OTHER INFORMATION: a, c, g, t, unknown or other
<220> FEATURE:
<221> NAME/KEY: modified_base
<222> LOCATION: (12)..(12)
<223> OTHER INFORMATION: a, c, g, t, unknown or other

<400> SEQUENCE: 67
accggaatng cngggt                                                 17

<210> SEQ ID NO 68
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (2)..(2)
<223> OTHER INFORMATION: Inosine
<220> FEATURE:
<221> NAME/KEY: modified_base
<222> LOCATION: (6)..(6)
<223> OTHER INFORMATION: Inosine
<220> FEATURE:
<221> NAME/KEY: modified_base
<222> LOCATION: (9)..(9)
<223> OTHER INFORMATION: Inosine

<400> SEQUENCE: 68
ancccngcna ttccggt                                                17

<210> SEQ ID NO 69
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
ttgggcgtgc ccccgcaagt tttcagtacc acaaggcctt tcgcgacc              48

<210> SEQ ID NO 70
<211> LENGTH: 25
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
cagtaccaca aggcctttcg cgacc                                          25

<210> SEQ ID NO 71
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
ttgggcgtgc ccccgcaag                                                 19

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
ctgctagccg agtagtgttg                                                20

<210> SEQ ID NO 73
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
ctgcggaacc ggtgagtac                                                 19

<210> SEQ ID NO 74
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
tccaagaaag gacccggtc                                                 19

<210> SEQ ID NO 75
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
tcgtcctggc aattccg                                                   17

<210> SEQ ID NO 76
<211> LENGTH: 222
<212> TYPE: DNA
```

<213> ORGANISM: Hepatitis c virus

<400> SEQUENCE: 76

```
tcgtgcagcc tccaggaccc ccctctcgg gagagccata gtggtctgcg gaaccggtga      60
gtacaccgga attgccagga cgaccgggtc ctttcttgga tcaacccgct caatgcctgg    120
agatttgggc gtgccccgc gagactgcta gccgagtagt gttgggtcgc gaaaggcctt    180
gtggtactgc ctgatagggt gcttgcgagt gcctcgggag gt                       222
```

<210> SEQ ID NO 77
<211> LENGTH: 222
<212> TYPE: DNA
<213> ORGANISM: Hepatitis c virus

<400> SEQUENCE: 77

```
tcgtacagcc tccaggcccc ccctcccgg gagagccata gtggtctgcg gaaccggtga      60
gtacaccgga attgccggga agactgggtc ctttcttgga taaacccact ctatgcccgg   120
ccatttgggc gtgccccgc aagactgcta gccgagtagc gttgggttgc gaaaggcctt    180
gtggtactgc ctgatagggt gcttgcgagt gccccgggag gt                       222
```

<210> SEQ ID NO 78
<211> LENGTH: 222
<212> TYPE: DNA
<213> ORGANISM: Hepatitis c virus

<400> SEQUENCE: 78

```
tcgtgcagcc tccaggatcc ccctcccgg gagagccata gtggtctgcg gaaccggtga      60
gtacaccgga atcgctgggg tgaccgggtc ctttcttgga gcaacccgct caataccag   120
aaatttgggc gtgccccgc gagatcacta gccgagtagt gttgggtcgc gaaaggcctt    180
gtggtactgc ctgatagggt gcttgcgagt gccccgggag gt                       222
```

<210> SEQ ID NO 79
<211> LENGTH: 222
<212> TYPE: DNA
<213> ORGANISM: Hepatitis c virus

<400> SEQUENCE: 79

```
ttgtacagcc tccaggaccc ccctcccgg gagagccata gtggtctgcg gaaccggtga      60
gtacaccgga atcgccggga tgaccgggtc ctttcttgga taaacccgct caatgcccgg   120
aaatttgggc gtgccccgc aagactgcta gccgagtagt gttgggtcgc gaaaggcctt    180
gtggtactgc ctgatagggt gcttgcgagt gccccgggag gt                       222
```

<210> SEQ ID NO 80
<211> LENGTH: 190
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 80

```
cctcccggga gagccatagt ggtctgcgga accggtgagt acaccggaat tgccgggayg      60
accgggtcct tcttggatm aacccgctca tgcccggar atttgggcgt gccccgcaa      120
gactgctagc cgagtagtgt tgggtcgcga aaggccttgt ggtactgcct gatagggtgc    180
ttgcgagtgc                                                          190
```

<210> SEQ ID NO 81
<211> LENGTH: 190
<212> TYPE: DNA
<213> ORGANISM: Hepatitis c virus

<400> SEQUENCE: 81

```
cctcccggga gagccatagt ggtctgcgga accggtgagt acaccggaat tgccaggacg      60
accgggtcct ttcgtggata aacccgctca atgcctggag atttgggcgt gcccccgcaa     120
gactgctagc cgagtagtgt tgggtcgcga aaggccttgt ggtactgcct gatagggtgc     180
ttgcgagtgc                                                            190
```

<210> SEQ ID NO 82
<211> LENGTH: 190
<212> TYPE: DNA
<213> ORGANISM: Hepatitis c virus

<400> SEQUENCE: 82

```
cctcccggga gagccatagt ggtctgcgga accggtgagt acaccggaat tgccaggacg      60
accgggtcct ttcttggatc aacccgctca atgcctggag atttgggcgt gcccccgcga     120
gactgctagc cgagtagtgt tgggtcgcga aaggccttgt ggtactgcct gatagggtgc     180
ttgcgagtgc                                                            190
```

<210> SEQ ID NO 83
<211> LENGTH: 190
<212> TYPE: DNA
<213> ORGANISM: Hepatitis c virus

<400> SEQUENCE: 83

```
cctcccggga aagccatagt ggtctgcgga accggtgagt acaccggaat taccggaaag      60
actgggtcct ttcttggata aacccactct atgtccggtc atttgggcgt gcccccgcaa     120
gactgctagc ctagtagcgt tgggttgcga acggccttgt ggtactgcct gatagggtgc     180
ttgcgagtgc                                                            190
```

<210> SEQ ID NO 84
<211> LENGTH: 190
<212> TYPE: DNA
<213> ORGANISM: Hepatitis c virus

<400> SEQUENCE: 84

```
cctcccggga gagccatagt ggtctgcgga accggtgagt acaccggaat cgctggggtg      60
accgggtcct ttcttggagc aacccgctca atacccagaa atttgggcgt gcccccgcga     120
gatcactagc cgagtagtgt tgggtcgcga aaggccttgt ggtactgcct gatagggtgc     180
ttgcgagtgc                                                            190
```

<210> SEQ ID NO 85
<211> LENGTH: 190
<212> TYPE: DNA
<213> ORGANISM: Hepatitis c virus

<400> SEQUENCE: 85

```
cctcccggga gagccatagt ggtctgcgga accggtgagt acaccggaat cgccgggatg      60
accgggtcct ttcttggatt aacccgctca atgcccggaa atttgggcgt gcccccgcaa     120
gactgctagc cgagtagtgt tgggtcgcga aaggccttgt ggtactgcct gatagggtgc     180
ttgcgagtgc                                                            190
```

<210> SEQ ID NO 86
<211> LENGTH: 200
<212> TYPE: DNA
<213> ORGANISM: Hepatitis c virus

<400> SEQUENCE: 86

| atgagcacga atcctaaacc tcaaagaaaa accaaacgta acaccaaccg tcgcccacag | 60 |
| gacgtcaagt tcccgggtgg cggtcagatc gttggtggag tttacttgtt gccgcgcagg | 120 |
| ggccctagat tgggtgtgcg cgcgacgagg aagacttccg agcggtcgca acctcgaggt | 180 |
| agacgtcagc ctatccccaa | 200 |

<210> SEQ ID NO 87
<211> LENGTH: 200
<212> TYPE: DNA
<213> ORGANISM: Hepatitis c virus

<400> SEQUENCE: 87

| atgagcacga atcctaaacc tcaaagaaaa accaaacgta acaccaaccg ccgcccacag | 60 |
| gacgtcaagt tcccgggcgg tggtcagatc gttggtggag tttacctgtt gccgcgcagg | 120 |
| ggccccaggt tgggtgtgcg cgcgactagg aagacttccg agcggtcgca acctcgtgga | 180 |
| aggcgacaac ctatccccaa | 200 |

<210> SEQ ID NO 88
<211> LENGTH: 231
<212> TYPE: DNA
<213> ORGANISM: Hepatitis c virus

<400> SEQUENCE: 88

| gtctagccat ggcgttagta tgagtgtcgt gcagcctcca ggaccccccc tcccgggaga | 60 |
| gccatagtgg tctgcggaac cggtgagtac accggaattg ccaggacgac cgggtccttt | 120 |
| cttggataaa cccgctcaat gcctggagat ttgggcgtgc ccccgcaaga ctgctagccg | 180 |
| agtagtgttg ggtcgcgaaa ggccttgtgg tactgcctga tagggtgctt g | 231 |

<210> SEQ ID NO 89
<211> LENGTH: 231
<212> TYPE: DNA
<213> ORGANISM: Hepatitis c virus

<400> SEQUENCE: 89

| gtctagccat ggcgttagta tgagtgtcgt gcagcctcca ggaccccccc tcccgggaga | 60 |
| gccatagtgg tctgcggaac cggtgagtac accggaattg ccaggacgac cgggtccttt | 120 |
| cttggatcaa cccgctcaat gcctggagat ttgggcgtgc ccccgcgaga ctgctagccg | 180 |
| agtagtgttg ggtcgcgaaa ggccttgtgg tactgcctga tagggtgctt g | 231 |

<210> SEQ ID NO 90
<211> LENGTH: 231
<212> TYPE: DNA
<213> ORGANISM: Hepatitis c virus

<400> SEQUENCE: 90

| gtctagccat ggcgttagta tgagtgtcgt acagcctcca ggccccccc tcccgggaga | 60 |
| gccatagtgg tctgcggaac cggtgagtac accggaattg ccgggaagac tgggtccttt | 120 |
| cttggataaa cccactctat gcccggccat ttgggcgtgc ccccgcaaga ctgctagccg | 180 | agtagcgttg ggttgcgaaa ggccttgtgg tactgcctga tagggtgctt g        231

<210> SEQ ID NO 91
<211> LENGTH: 231
<212> TYPE: DNA
<213> ORGANISM: Hepatitis c virus

<400> SEQUENCE: 91
gtctagccat ggcgttagta tgagtgtcgt acagcctcca ggccccccc tcccgggaga        60 gccatagtgg tctgcggaac cggtgagtac accggaatta ccggaaagac tgggtccttt      120
cttggataaa cccactctat gtccggtcat ttgggcgtgc cccgcaaga ctgctagccg       180 agtagcgttg ggttgcgaaa ggccttgtgg tactgcctga tagggtgctt g               231

<210> SEQ ID NO 92
<211> LENGTH: 231
<212> TYPE: DNA
<213> ORGANISM: Hepatitis c virus

<400> SEQUENCE: 92
gcctagccat ggcgttagta cgagtgtcgt gcagcctcca ggacccccc tcccgggaga        60 gccatagtgg tctgcggaac cggtgagtac accggaatcg ctggggtgac cgggtccttt      120
cttggaacaa cccgctcaat acccagaaat ttgggcgtgc cccgcgaga tcactagccg       180 agtagtgttg ggtcgcgaaa ggccttgtgg tactgcctga tagggtgctt g               231

<210> SEQ ID NO 93
<211> LENGTH: 232
<212> TYPE: DNA
<213> ORGANISM: Hepatitis c virus

<400> SEQUENCE: 93
gtctagccat ggcgttagta tgagtgttgt acagcctcca ggacccccc tcccgggaga        60 gccatagtgg tctgcggaac cggtgagtac accggaatcg ccaggacgac cgggtccttt      120
cttggattaa acccgctcaa tgcctggaaa tttgggcgtg ccccccgcaag actgctagcc    180 gagtagtgtt gggttgcgaa aggccttgtg gtactgcctg atagggtgct tg             232

<210> SEQ ID NO 94
<211> LENGTH: 95
<212> TYPE: DNA
<213> ORGANISM: Hepatitis c virus

<400> SEQUENCE: 94
tttgggcgtg ccccccgcaag actgctagcc gagtagtgtt gggtcgcgaa aggccttgtg     60
gtactgcctg atagggtgct tgcttgcgag tgccc                                 95

<210> SEQ ID NO 95
<211> LENGTH: 95
<212> TYPE: DNA
<213> ORGANISM: Hepatitis c virus

<400> SEQUENCE: 95
gggcactcgc aagcaagcac cctatcaggc agtaccacaa ggcctttcgc gacccaacac      60
tactcggcta gcagtcttgc ggggcacgc ccaaa                                  95

<210> SEQ ID NO 96
<211> LENGTH: 11
<212> TYPE: PRT
<213> ORGANISM: Hepatitis c virus

```
<400> SEQUENCE: 96

Phe Gly Arg Ala Pro Ala Arg Leu Leu Ala Glu
1               5                   10

<210> SEQ ID NO 97
<211> LENGTH: 19
<212> TYPE: PRT
<213> ORGANISM: Hepatitis c virus

<400> SEQUENCE: 97

Cys Trp Val Ala Lys Gly Leu Val Val Leu Pro Asp Arg Val Leu Ala
1               5                   10                  15

Ser Ala Pro

<210> SEQ ID NO 98
<211> LENGTH: 104
<212> TYPE: DNA
<213> ORGANISM: Hepatitis c virus

<400> SEQUENCE: 98
gcagcctcca ggaccccccc tcccgggaga gccatagtgg tctgcggaac cggtgagtac      60
accggaattg ccaggacgac cgggtccttt cttggataaa cccg                     104

<210> SEQ ID NO 99
<211> LENGTH: 104
<212> TYPE: DNA
<213> ORGANISM: Hepatitis c virus

<400> SEQUENCE: 99
cgggtttatc caagaaagga cccggtcgtc ctggcaattc cggtgtactc accggttccg      60
cagaccacta tggctctccc gggagggggg gtcctggagg ctgc                     104

<210> SEQ ID NO 100
<211> LENGTH: 17
<212> TYPE: PRT
<213> ORGANISM: Hepatitis c virus

<400> SEQUENCE: 100

Ser Leu Gln Asp Pro Pro Ser Arg Glu Ser His Ser Gly Leu Arg Asn
1               5                   10                  15

Arg

<210> SEQ ID NO 101
<211> LENGTH: 16
<212> TYPE: PRT
<213> ORGANISM: Hepatitis c virus

<400> SEQUENCE: 101

Val His Arg Asn Cys Gln Asp Asp Arg Val Leu Ser Trp Ile Asn Pro
1               5                   10                  15
```

ENHANCED NUCLEIC ACID IDENTIFICATION AND DETECTION

CROSS-REFERENCE

This application is a continuation of U.S. application Ser. No. 15/030,202, filed Apr. 18, 2016, which is a U.S. National Phase patent application of PCT/US2014/060977, filed Oct. 16, 2014, which claims the benefit of U.S. Provisional Application No. 61/893,051, filed Oct. 18, 2013, U.S. Provisional Application No. 61/943,784, filed Feb. 24, 2014, U.S. Provisional Application No. 61/968,191, filed Mar. 20, 2014, U.S. Provisional Application No. 61/993,183, filed May 14, 2014, and U.S. Provisional Application No. 62/063,293, filed Oct. 13, 2014, all of which are incorporated herein by reference.

STATEMENT AS TO FEDERALLY SPONSORED RESEARCH

This invention was made with government support under Grant No. OD003584, Grant No. EB012946, and Grant No. GM007616 awarded by the National Institutes of Health and under Grant No. HR0011-11-2-0006 awarded by DARPA. The government has certain rights in the invention.

SEQUENCE LISTING

The instant application contains a Sequence Listing which has been submitted electronically in ASCII format and is hereby incorporated by reference in its entirety. Said ASCII copy, created on Dec. 18, 2018, is named 42436_US_Sequence_Listing.txt and is 29,414 bytes in size.

BACKGROUND

Modern biological techniques, including nucleic acid analysis, offer powerful tools for the analysis of samples. Samples from subjects and environmental sources can be analyzed for the presence of various compounds and organisms. Patients can be diagnosed for diseases, including infectious diseases and genetic diseases. Samples can be genotyped.

However, many analysis techniques require centralized laboratory facilities, trained technicians, sample preparation, refrigeration, and other resources. Such requirements can limit the utility of these techniques in point-of-care settings, limited resource settings, and other environments with difficult or no access to necessary resources.

SUMMARY

In some aspects, this disclosure provides a method comprising: (a) providing a first solution comprising a first nucleic acid and a modulator, wherein said modulator is capable of acting on said first nucleic acid in a region amplified by an isothermal nucleic acid amplification reaction, thereby modulating said isothermal nucleic acid amplification reaction; (b) preparing a second solution comprising a second nucleic acid and optionally comprising said modulator; and (c) conducting said isothermal nucleic acid amplification reaction in said first solution and in said second solution.

In some aspects, this disclosure provides a method comprising: (a) providing a volume suspected of containing a target nucleic acid molecule; and (b) conducting an isothermal nucleic acid amplification reaction in said volume in the presence of a modulator, wherein said modulator modulates said nucleic acid amplification reaction in the presence of said target nucleic acid molecule and wherein said modulator acts on said target nucleic acid molecule within a region amplified by said isothermal nucleic acid amplification reaction.

In some aspects, this disclosure provides a method comprising: (a) providing a first volume comprising first nucleic acid and a second volume comprising second nucleic acid; (b) dispersing said first volume among a plurality of first areas such that said plurality of first areas each comprise at most one copy of said first nucleic acid and dispersing said second volume among a plurality of second areas such that said plurality of second areas each comprise at most one copy of said second nucleic acid; (c) providing a modulator to said plurality of first areas or to said plurality of second areas, wherein said modulator modulates a nucleic acid amplification reaction when in the presence of said first nucleic acid; and (d) conducting said nucleic acid amplification reaction in said plurality of first areas and said plurality of second areas.

In some aspects, this disclosure provides a method comprising: (a) providing a volume suspected of containing target nucleic acid molecules; (b) dispersing said volume among a plurality of areas, such that said plurality of areas each comprise at most one of said target nucleic acid molecules; (c) providing a modulator to said plurality of areas, wherein said modulator modulates a nucleic acid amplification reaction in the presence of said target nucleic acid molecule; (d) conducting said nucleic acid amplification reaction in said plurality of areas.

In some aspects, this disclosure provides a method comprising: (a) providing a first volume comprising first nucleic acid and a second volume comprising second nucleic acid; (b) dispersing said first volume among a plurality of first areas and dispersing said second volume among a plurality of second areas; (c) providing a modulator to said plurality of first areas or to said plurality of second areas, wherein said modulator modulates a nucleic acid amplification reaction when in the presence of said first nucleic acid; and (d) conducting said nucleic acid amplification reaction in said plurality of first areas and in said plurality of second areas, thereby producing positive amplification signal in a subset of said plurality of first areas.

In some aspects, this disclosure provides a method comprising: (a) providing a volume suspected of containing target nucleic acid molecules; (b) dispersing said volume among a plurality of areas; (c) providing a modulator to said plurality of areas, wherein said modulator modulates a nucleic acid amplification reaction in the presence of said target nucleic acid molecule; (d) conducting said nucleic acid amplification reaction in said plurality of areas, thereby producing positive amplification signal in a subset of said plurality of areas.

In some embodiments of aspects provided herein, the method further comprises detecting a difference in amplification between said first nucleic acid and said second nucleic acid. In some embodiments of aspects provided herein, said difference in amplification comprises a difference in amplification rate. In some embodiments of aspects provided herein, said difference in amplification comprises a difference in amplification efficiency. In some embodiments of aspects provided herein, said difference in amplification comprises a difference in amplification rate and a difference in amplification efficiency. In some embodiments of aspects provided herein, said detecting comprises performing sequencing. In some embodiments of aspects provided herein, said detecting does not comprise performing sequencing. In some embodiments of aspects provided herein, said detecting comprises mass spectrometry. In some embodiments of aspects provided herein, said detecting does not comprise mass spectrometry. In some embodiments of aspects provided herein, said detecting comprises performing electrophoresis. In some embodiments of aspects provided herein, said detecting does not comprise performing electrophoresis. In some embodiments of aspects provided herein, said providing a modulator of step (c) occurs before said dispersing of step (b). In some embodiments of aspects provided herein, said providing a modulator of step (c) occurs during said dispersing of step (b). In some embodiments of aspects provided herein, said providing a modulator of step (c) occurs after said dispersing of step (b). In some embodiments of aspects provided herein, the method further comprises dispersing said first volume among a plurality of third areas such that said plurality of third areas each comprise more than one copy of said first nucleic acid and dispersing said second volume among a plurality of fourth areas such that said plurality of fourth areas each comprise more than one copy of said second nucleic acid. In some embodiments of aspects provided herein, the method further comprises dispersing said volume among a second plurality of areas, such that said second plurality of areas each comprise more than one of said target nucleic acid molecules. In some embodiments of aspects provided herein, said modulator acts during said nucleic acid amplification reaction. In some embodiments of aspects provided herein, said modulator acts before said nucleic acid amplification reaction. In some embodiments of aspects provided herein, said modulator acts after said nucleic acid amplification reaction. In some embodiments of aspects provided herein, said modulator acts by inhibiting said nucleic acid amplification reaction. In some embodiments of aspects provided herein, said modulator acts by promoting said nucleic acid amplification reaction. In some embodiments of aspects provided herein, said modulator acts by promoting said nucleic acid amplification reaction by inhibiting off-target reactions. In some embodiments of aspects provided herein, said nucleic acid amplification reaction comprises an isothermal amplification reaction. In some embodiments of aspects provided herein, said isothermal nucleic acid amplification reaction is performed in a digital format. In some embodiments of aspects provided herein, said modulator acts on a nucleic acid outside of a priming region of said nucleic acid amplification reaction. In some embodiments of aspects provided herein, said modulator acts on a nucleic acid inside a priming region of said nucleic acid amplification reaction. In some embodiments of aspects provided herein, said modulator comprises an enzyme. In some embodiments of aspects provided herein, said modulator comprises an enzyme that acts on nucleic acids in a sequence-targeted manner. In some embodiments of aspects provided herein, said modulator binds a nucleic acid molecule in a sequence-targeted manner. In some embodiments of aspects provided herein, said modulator acts on nucleic acids in a methylation-targeted manner. In some embodiments of aspects provided herein, said modulator acts on nucleic acids in a glycosylation-targeted manner. In some embodiments of aspects provided herein, said modulator comprises a restriction enzyme. In some embodiments of aspects provided herein, said modulator comprises a nucleic acid modifying enzyme. In some embodiments of aspects provided herein, said modulator comprises a ligase. In some embodiments of aspects provided herein, said modulator comprises an engineered or non-natural nuclease. In some embodiments of aspects provided herein, said modulator comprises a modulator selected from the group consisting of zinc-finger nuclease, transcription activator-like effector nuclease, meganuclease, and RNA-guided Cas9 nuclease. In some embodiments of aspects provided herein, said modulator comprises an oligonucleotide. In some embodiments of aspects provided herein, said modulator comprises an artificial nucleic acid or a nucleic acid analog. In some embodiments of aspects provided herein, said modulator comprises peptide nucleic acid (PNA), locked nucleic acid (LNA), inosine, or dideoxynucleotide (ddNTP). In some embodiments of aspects provided herein, said modulator comprises an oligonucleotide comprising modified bases or unnatural bases. In some embodiments of aspects provided herein, said modulator comprises a repair protein. In some embodiments of aspects provided herein, said modulator comprises a repair protein selected from the group consisting of MutH, MutL, and MutS. In some embodiments of aspects provided herein, said modulator promotes said nucleic acid amplification reaction by affecting secondary structures. In some embodiments of aspects provided herein, said modulator competes with primers for said nucleic acid amplification reaction. In some embodiments of aspects provided herein, said modulator is inactive until activation by an enzymatic activity. In some embodiments of aspects provided herein, said conducting occurs on a microfluidic device. In some embodiments of aspects provided herein, said conducting occurs on a microwell plate. In some embodiments of aspects provided herein, said conducting occurs on a solid support. In some embodiments of aspects provided herein, said conducting occurs not on a solid support. In some embodiments of aspects provided herein, said conducting occurs in microfluidic droplets. In some embodiments of aspects provided herein, said conducting occurs in an emulsion.

In some aspects, this disclosure provides a method comprising: (a) providing a volume suspected of containing a first target nucleic acid molecule; (b) conducting a first nucleic acid amplification reaction on a first part of said volume in the presence of a first modulator, wherein said first modulator modulates said first nucleic acid amplification reaction in the presence of said first target nucleic acid molecule; (c) conducting a second nucleic acid amplification reaction on a second part of said volume, optionally in the presence of a second modulator, wherein said second modulator, if present, modulates said second nucleic acid amplification reaction in the presence of a second target nucleic acid molecule; (d) generating a modulated amplification pattern based on results from said first nucleic acid amplification reaction and said second nucleic acid amplification reaction; and (e) comparing said modulated amplification pattern to a reference pattern.

In some embodiments of aspects provided herein, said results comprise amplification rate results. In some embodiments of aspects provided herein, said results comprise amplification efficiency results. In some embodiments of aspects provided herein, said results comprise amplification rate results and amplification efficiency results. In some embodiments of aspects provided herein, said generating does not comprise gel electrophoresis. In some embodiments of aspects provided herein, said first modulator or said second modulator acts during said nucleic acid amplification reaction. In some embodiments of aspects provided herein, said first modulator or said second modulator acts before said nucleic acid amplification reaction. In some embodiments of aspects provided herein, said first modulator or said second modulator acts after said nucleic acid amplification reaction. In some embodiments of aspects provided herein, said first modulator or said second modulator acts by inhibiting said nucleic acid amplification reaction. In some embodiments of aspects provided herein, said first modulator or said second modulator acts by promoting said nucleic acid amplification reaction. In some embodiments of aspects provided herein, said first modulator or said second modulator acts by promoting said nucleic acid amplification reaction by inhibiting off-target reactions. In some embodiments of aspects provided herein, said first nucleic acid amplification reaction or said second nucleic acid amplification reaction comprises an isothermal amplification reaction. In some embodiments of aspects provided herein, said first nucleic acid amplification reaction or said second nucleic acid amplification is performed in a digital format. In some embodiments of aspects provided herein, said first modulator or said second modulator acts on a nucleic acid outside of a priming region of said nucleic acid amplification reaction. In some embodiments of aspects provided herein, said first modulator or said second modulator comprises an enzyme. In some embodiments of aspects provided herein, said first modulator or said second modulator comprises an enzyme that acts on nucleic acids in a sequence-targeted manner. In some embodiments of aspects provided herein, said first modulator or said second modulator binds a nucleic acid molecule in a sequence-targeted manner. In some embodiments of aspects provided herein, said first modulator or said second modulator acts on nucleic acids in a methylation-targeted manner. In some embodiments of aspects provided herein, said first modulator or said second modulator acts on nucleic acids in a glycosylation-targeted manner. In some embodiments of aspects provided herein, said first modulator or said second modulator comprises a restriction enzyme. In some embodiments of aspects provided herein, said first modulator or said second modulator comprises a nucleic acid modifying enzyme. In some embodiments of aspects provided herein, said first modulator or said second modulator comprises a ligase. In some embodiments of aspects provided herein, said first modulator or said second modulator comprises an engineered or non-natural nuclease. In some embodiments of aspects provided herein, said first modulator or said second modulator comprises a modulator selected from the group consisting of zinc-finger nuclease, transcription activator-like effector nuclease, meganuclease, and RNA-guided Cas9 nuclease. In some embodiments of aspects provided herein, said first modulator or said second modulator comprises an oligonucleotide. In some embodiments of aspects provided herein, said first modulator or said second modulator comprises an artificial nucleic acid or a nucleic acid analog. In some embodiments of aspects provided herein, said first modulator or said second modulator comprises peptide nucleic acid (PNA), locked nucleic acid (LNA), inosine, or dideoxynucleotide (ddNTP). In some embodiments of aspects provided herein, said first modulator or said second modulator comprises an oligonucleotide comprising modified bases or unnatural bases. In some embodiments of aspects provided herein, said first modulator or said second modulator comprises a repair protein. In some embodiments of aspects provided herein, said first modulator or said second modulator comprises a repair protein selected from the group consisting of MutH, MutL, and MutS. In some embodiments of aspects provided herein, said first modulator or said second modulator promotes said nucleic acid amplification reaction by affecting secondary structures. In some embodiments of aspects provided herein, said first modulator or said second modulator competes with primers for said nucleic acid amplification reaction. In some embodiments of aspects provided herein, said first modulator or said second modulator is inactive until activation by an enzymatic activity. In some embodiments of aspects provided herein, said conducting a first nucleic acid amplification reaction or said conducting a second nucleic acid amplification reaction occurs on a microfluidic device. In some embodiments of aspects provided herein, said conducting a first nucleic acid amplification reaction or said conducting a second nucleic acid amplification reaction occurs on a microwell plate. In some embodiments of aspects provided herein, said conducting a first nucleic acid amplification reaction or said conducting a second nucleic acid amplification reaction occurs on a solid support. In some embodiments of aspects provided herein, said conducting a first nucleic acid amplification reaction or said conducting a second nucleic acid amplification reaction occurs not on a solid support. In some embodiments of aspects provided herein, said conducting a first nucleic acid amplification reaction or said conducting a second nucleic acid amplification reaction occurs in microfluidic droplets. In some embodiments of aspects provided herein, said conducting a first nucleic acid amplification reaction or said conducting a second nucleic acid amplification reaction occurs in an emulsion.

In some aspects, this disclosure provides a method comprising: (a) providing a first volume comprising a first nucleic acid and a second volume comprising a second nucleic acid; (b) dispersing said first volume among a plurality of first areas; (c) dispersing said second volume among a plurality of second areas; (d) providing a modulator to said plurality of first areas or to said plurality of second areas; and (e) conducting said nucleic acid amplification reaction, thereby producing a positive signal in a subset of said plurality of first areas, wherein said modulator modulates said producing when in the presence of said first nucleic acid.

In some aspects, this disclosure provides a method comprising: (a) providing a volume suspected of containing a target nucleic acid molecule; (b) dispersing said volume among a plurality of areas; (c) dispersing a modulator among said plurality of areas; (c) conducting said nucleic acid amplification reaction in said plurality of areas, thereby producing a positive amplification signal in a subset of said plurality of areas, wherein said modulator modulates said producing when in the presence of said target nucleic acid molecule.

In some embodiments of aspects provided herein, said producing comprises producing fluorescence. In some embodiments of aspects provided herein, said producing comprises producing a precipitate. In some embodiments of aspects provided herein, said producing comprises producing a gas bubble. In some embodiments of aspects provided herein, said producing comprises conducting nucleic acid sequencing. In some embodiments of aspects provided herein, said producing comprises conducting mass spectrometry. In some embodiments of aspects provided herein, said producing comprises quenching. In some embodiments of aspects provided herein, said modulator comprises an enzyme. In some embodiments of aspects provided herein, said modulator comprises an enzyme that acts on nucleic acids in a sequence-targeted manner. In some embodiments of aspects provided herein, said modulator binds a nucleic acid molecule in a sequence-targeted manner. In some embodiments of aspects provided herein, said modulator acts on nucleic acids in a methylation-targeted manner. In some embodiments of aspects provided herein, said modulator acts on nucleic acids in a glycosylation-targeted manner. In some embodiments of aspects provided herein, said modulator comprises a restriction enzyme. In some embodiments of aspects provided herein, said modulator comprises a nucleic acid modifying enzyme. In some embodiments of aspects provided herein, said modulator comprises a ligase. In some embodiments of aspects provided herein, said modulator comprises an engineered or non-natural nuclease. In some embodiments of aspects provided herein, said modulator comprises a modulator selected from the group consisting of zinc-finger nuclease, transcription activator-like effector nuclease, meganuclease, and RNA-guided Cas9 nuclease. In some embodiments of aspects provided herein, said modulator comprises an oligonucleotide. In some embodiments of aspects provided herein, said modulator comprises an artificial nucleic acid or a nucleic acid analog. In some embodiments of aspects provided herein, said modulator comprises peptide nucleic acid (PNA), locked nucleic acid (LNA), inosine, or dideoxynucleotide (ddNTP). In some embodiments of aspects provided herein, said modulator comprises an oligonucleotide comprising modified bases or unnatural bases. In some embodiments of aspects provided herein, said modulator comprises a repair protein. In some embodiments of aspects provided herein, said modulator comprises a repair protein selected from the group consisting of MutH, MutL, and MutS. In some embodiments of aspects provided herein, said modulator promotes said nucleic acid amplification reaction by affecting secondary structures. In some embodiments of aspects provided herein, said modulator competes with primers for said nucleic acid amplification reaction. In some embodiments of aspects provided herein, said modulator is inactive until activation by an enzymatic activity. In some embodiments of aspects provided herein, said conducting occurs on a microfluidic device. In some embodiments of aspects provided herein, said conducting occurs on a microwell plate. In some embodiments of aspects provided herein, said conducting occurs on a solid support. In some embodiments of aspects provided herein, said conducting occurs not on a solid support. In some embodiments of aspects provided herein, said conducting occurs in microfluidic droplets. In some embodiments of aspects provided herein, said conducting occurs in an emulsion. In some embodiments of aspects provided herein, said nucleic acid amplification reaction is conducted in a digital format. In some embodiments of aspects provided herein, said nucleic acid amplification reaction comprises an isothermal nucleic acid amplification reaction.

In some aspects, this disclosure provides a method comprising: (a) providing a volume comprising first reagents for a first reaction and second reagents for a second reaction; (b) conducting said first reaction and said second reaction; and (c) observing results from said first reaction, thereby determining the relative rate or relative efficiency of said first reaction and said second reaction.

In some aspects, this disclosure provides a method comprising: (a) providing a volume comprising first reagents for a first reaction second reagents for a second reaction; (b) dispersing said volume among a plurality of areas; and (c) conducting said first reaction and said second reaction in said plurality of areas, thereby producing positive signal in a subset of said plurality of first areas.

In some embodiments of aspects provided herein, said conducting occurs on a microfluidic device. In some embodiments of aspects provided herein, said conducting occurs on a microwell plate. In some embodiments of aspects provided herein, said conducting occurs on a solid support. In some embodiments of aspects provided herein, said conducting occurs not on a solid support. In some embodiments of aspects provided herein, said conducting occurs in microfluidic droplets. In some embodiments of aspects provided herein, said conducting occurs in an emulsion. In some embodiments of aspects provided herein, said conducting occurs in a digital format. In some embodiments of aspects provided herein, said reaction, said first reaction, or said second reaction comprise an isothermal reaction.

In some aspects, this disclosure provides a device comprising: (a) a sample inlet; (b) a reaction chamber; (c) a first modulator; and (d) a fluid handling component, wherein said fluid handling component is positioned to combine said first modulator with a portion of a sample comprising an analyte loaded in said sample inlet.

In some embodiments of aspects provided herein, the device further comprises a second modulator. In some embodiments of aspects provided herein, the device further comprises amplification reaction reagents. In some embodiments of aspects provided herein, said amplification reaction reagents comprise isothermal amplification reaction reagents. In some embodiments of aspects provided herein, the device further comprises a sample preparation module. In some embodiments of aspects provided herein, the device further comprises a detector. In some embodiments of aspects provided herein, said first modulator or said second modulator comprises an enzyme. In some embodiments of aspects provided herein, said first modulator or said second modulator comprises an enzyme that acts on nucleic acids in a sequence-targeted manner. In some embodiments of aspects provided herein, said first modulator or said second modulator binds a nucleic acid molecule in a sequence-targeted manner. In some embodiments of aspects provided herein, said first modulator or said second modulator acts on nucleic acids in a methylation-targeted manner. In some embodiments of aspects provided herein, said first modulator or said second modulator acts on nucleic acids in a glycosylation-targeted manner. In some embodiments of aspects provided herein, said first modulator or said second modulator comprises a restriction enzyme. In some embodiments of aspects provided herein, said first modulator or said second modulator comprises a nucleic acid modifying enzyme. In some embodiments of aspects provided herein, said first modulator or said second modulator comprises a ligase. In some embodiments of aspects provided herein, said first modulator or said second modulator comprises an engineered or non-natural nuclease. In some embodiments of aspects provided herein, said first modulator or said second modulator comprises a first modulator or said second modulator selected from the group consisting of zinc-finger nuclease, transcription activator-like effector nuclease, meganuclease, and RNA-guided Cas9 nuclease. In some embodiments of aspects provided herein, said first modulator or said second modulator comprises an oligonucleotide. In some embodiments of aspects provided herein, said first modulator or said second modulator comprises an artificial nucleic acid or a nucleic acid analog. In some embodiments of aspects provided herein, said first modulator or said second modulator comprises peptide nucleic acid (PNA), locked nucleic acid (LNA), inosine, or dideoxynucleotide (ddNTP). In some embodiments of aspects provided herein, said first modulator or said second modulator comprises an oligonucleotide comprising modified bases or unnatural bases. In some embodiments of aspects provided herein, said first modulator or said second modulator comprises a repair protein. In some embodiments of aspects provided herein, said first modulator or said second modulator comprises a repair protein selected from the group consisting of MutH, MutL, and MutS. In some embodiments of aspects provided herein, said first modulator or said second modulator promotes said nucleic acid amplification reaction by affecting secondary structures. In some embodiments of aspects provided herein, said first modulator or said second modulator competes with primers for said nucleic acid amplification reaction. In some embodiments of aspects provided herein, said first modulator or said second modulator is inactive until activation by an enzymatic activity. In some embodiments of aspects provided herein, said device comprises a microfluidic device. In some embodiments of aspects provided herein, said device comprises a microwell plate. In some embodiments of aspects provided herein, said device comprises a solid support. In some embodiments of aspects provided herein, said device does not comprise a solid support. In some embodiments of aspects provided herein, said device comprises a microfluidic droplet generator. In some embodiments of aspects provided herein, said device comprises an emulsion generator. In some embodiments of aspects provided herein, said fluid handling component is configured to provide said portion of said sample to said reaction chamber such that said reaction chamber comprises at most one copy of said analyte. In some embodiments of aspects provided herein, said analyte comprises a nucleic acid. In some embodiments of aspects provided herein, said analyte comprises DNA. In some embodiments of aspects provided herein, said analyte comprises RNA.

INCORPORATION BY REFERENCE

All publications, patents, and patent applications mentioned in this specification are herein incorporated by reference in their entireties for all purposes to the same extent as if each individual publication, patent, or patent application was specifically and individually indicated to be incorporated by reference in its entirety for all purposes.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 5A shows an exemplary alignment of RNA sequence, priming region and digestion site for NheI, BstNI, BsrBI, BsrI, and BcoDI.

FIG. 17 shows an exemplary illustration of B side primer and primer part sequence variants (Seq ID Nos: 70-72 and 51) aligned to a typical HCV sequence (Seq ID No: 94, Seq ID No: 95) shown together with amino acid sequences encoded thereby (Seq ID No: 96, and Seq ID No: 97).

FIG. 24A shows an exemplary schematic of a SlipChip device top and bottom.

FIG. 24B shows an exemplary schematic of a SlipChip device aligned for loading.

FIG. 24C shows an exemplary schematic of a SlipChip device aligned for compartmentalization.

FIG. 32A shows exemplary results from performance of a NASBA reaction using a DNA molecular beacon (dashed line) and RNA molecular beacon (solid line) with standard concentration of RNase H.

FIG. 32B shows exemplary results from performance of a NASBA reaction using a DNA molecular beacon (dashed line) and RNA molecular beacon (solid line) with increased concentration of RNase H.

FIG. 33A shows exemplary results for mean time to positive from a modified NASBA reaction.

FIG. 33B shows exemplary results for mean final fluorescent intensity from a modified NASBA reaction.

FIG. 34A shows a graph of exemplary results from experiments on the effect of preincubation on the time to positive of restriction enzyme (ApoI) enhanced RNA NASBA compared to regular NASBA.

FIG. 34B shows exemplary results in an electrophoresis gel from experiments on the effect of preincubation on the time to positive of restriction enzyme (ApoI) enhanced RNA NASBA compared to regular NASBA

DETAILED DESCRIPTION

Overview

Herein described are approaches, devices and methods that can be used to control a process, such as a detection or an amplification reaction, by adding a modulator. A modulator can be an external substance that can produce a modulating (positive or negative) effect to the process (e.g., amplification) and can change (increase or decrease) one or more from the following: the rate of the process, the efficiency of the process, the amount of product, the identity of the product, or changes in the detection outcome. A modulator can be an inhibitor, producing a negative modulating effect. A modulator can be a promoter, producing a positive modulating effect. Detection can include detection by amplification, sequencing, mass spectrometry, electrophoresis, and others, as well as processes used as part of detection, such as reverse transcription; methods described herein can be used to impact these processes.

In some cases, processes (e.g. detection and/or amplification reactions) can be inhibited by the action of the modulator, such as restriction enzyme or restriction endonuclease (RE) or other nucleic acid modifying enzymes. For example, restriction enzymes can cleave templates or products of amplification or reverse transcription reactions. In some cases, a modulator can comprise a modified oligonucleotide ("oligo"). Isothermal amplification processes can provide advantages in these and other cases to broaden the range of inhibitors available for use to inhibit the process. In some examples, RNA-guided Cas9 nucleases from CRISPR system or peptide nucleic acid (PNA) can be used. In some examples, restriction enzymes (RE) can be used to control the process of RT-LAMP amplification to perform genotyping (e.g. HCV genotyping).

Figure 1:
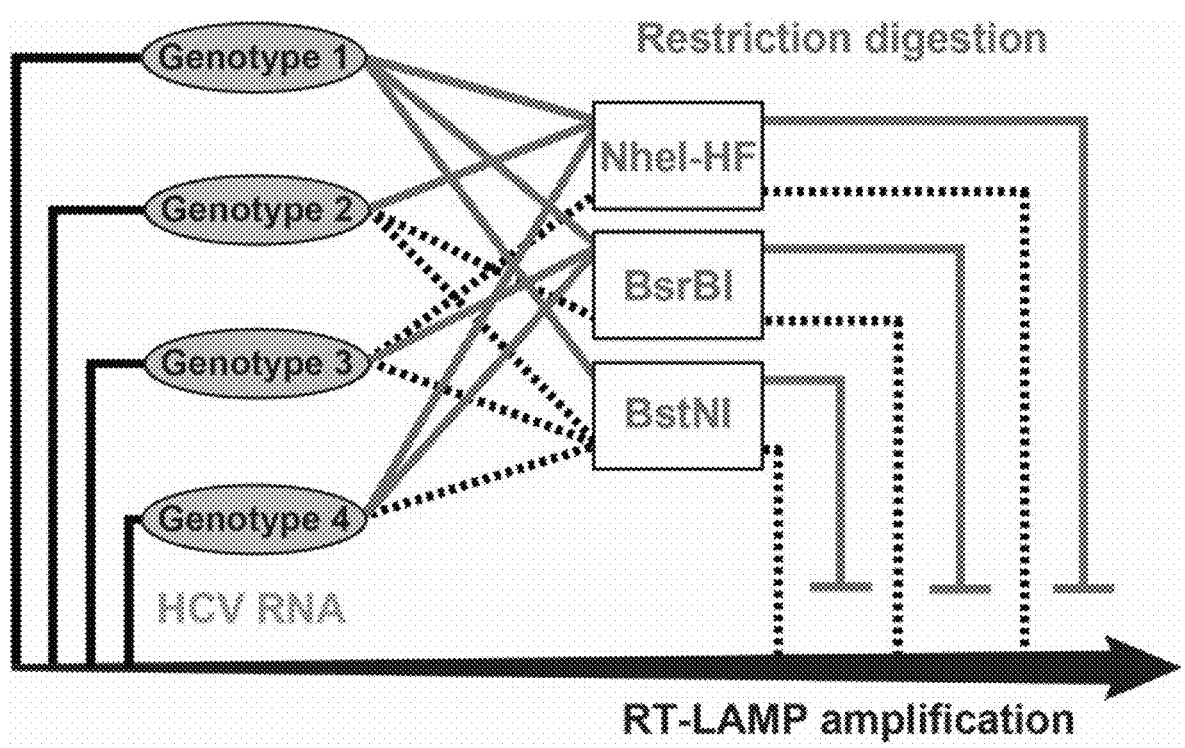
FIG. 1 shows an exemplary schematic of an assay design.

FIG. 1 shows an exemplary schematic of an assay design using amplification in the presence of restriction enzymes to genotype hepatitis C virus (HCV) RNA. Solid lines between genotypes (ovals, left side) and restriction enzymes (rectangles, right side) represent inhibition feedback and dashed lines represent lack of inhibition feedback. By conducting amplification reactions on a sample in the presence or absence of different restriction enzymes, the sample's genotype can be determined based on which inhibitors recognize the sample nucleic acid and therefore inhibit its amplification.

Figures 2A, 2B:
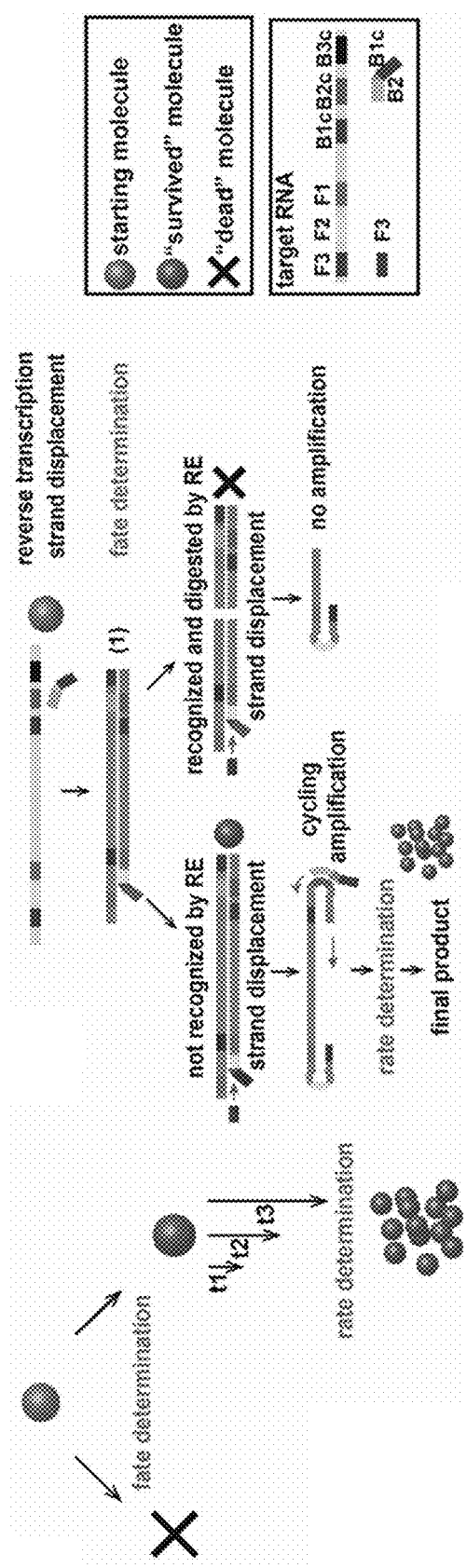
FIG. 2A shows an exemplary schematic illustrating the possible outcome and rate of an amplification reaction.
FIG. 2B shows an exemplary schematic illustrating the possible outcome and rate of a nucleic acid amplification reaction in the presence of a restriction enzyme.

FIG. 2 shows a schematic illustrating the possible outcome ("fate") and rate of an amplification reaction. FIG. 2A shows a starting molecule (top) with two possible outcomes or fates—no amplification (left path) and amplification (right path). If the molecule undergoes amplification, the rate of amplification can also be measured. FIG. 2B shows a starting nucleic acid molecule (top) with two possible outcomes or fates in the presence of a restriction enzyme—amplification (left path) or no amplification (right path). If the molecule undergoes amplification, the rate of amplification can also be measured.

In some cases, a ligation reaction (e.g., using a ligase) can be performed in combination with an amplification reaction, leading, for example, to the detection of the ligated product. In some cases, a modulator can modulate a ligation reaction. For example, a restriction enzyme can digest template or product of a ligation reaction.

The approaches, methods, and devices disclosed herein can provide different advantages. In some cases, methods can be used that do not require post-amplification digestion. In some cases, methods can be used that do not require electrophoresis, such as gel electrophoresis or capillary electrophoresis. In some cases, modulators (e.g., restriction enzymes, oligonucleotides) can provide specificity, such as by recognizing specific nucleotide sequences. In some cases, the method can provide high sensitivity, including single molecule sensitivity. Approaches, devices and methods disclosed herein can be used to produce nucleic acids for subsequent uses. Methods disclosed herein can comprise the detection, quantification, production, or degradation of one or more nucleic acids, including in a sequence-targeted or sequence-specific manner Methods disclosed herein can comprise detection or quantification of a single nucleotide polymorphism (SNP), a genotype of an allele, modifications of nucleic acid bases, molecules that interact with nucleic acids (including in a sequence-targeted or sequence specific manner), transcription factors, DNA-binding proteins, histones, oligonucleotides, or enzymes that interact with nucleic acids (including in a sequence-targeted or sequence specific manner). Methods disclosed herein can comprise homogeneous reactions. Methods disclosed herein can comprise one-step reactions or one-pot reactions. Methods disclosed herein can comprise providing a direct read-out.

The present application incorporates the following applications by reference in their entireties for any and all purposes: U.S. Application 61/516,628, "Digital Isothermal Quantification of Nucleic Acids Via Simultaneous Chemical Initiation of Recombinase Polymerase Amplification (RPA) Reactions on Slip Chip," filed on Apr. 5, 2011; U.S. Application 61/518,601, "Quantification of Nucleic Acids With Large Dynamic Range Using Multivolume Digital Reverse Transcription PCR (RT-PCR) On A Rotational Slip Chip Tested With Viral Load," filed on May 9, 2011; U.S. application Ser. No. 13/257,811, "Slip Chip Device and Methods," filed on Sep. 20, 2011; international application PCT/US2010/028361, "Slip Chip Device and Methods," filed on Mar. 23, 2010; U.S. Application 61/262,375, "Slip Chip Device and Methods," filed on Nov. 18, 2009; U.S. Application 61/162,922, "Sip Chip Device and Methods," filed on Mar. 24, 2009; U.S. Application 61/340,872, "Slip Chip Device and Methods," filed on Mar. 22, 2010; U.S. application Ser. No. 13/440,371, "Analysis Devices, Kits, And Related Methods For Digital Quantification Of Nucleic Acids And Other Analytes," filed on Apr. 5, 2012; and U.S. application Ser. No. 13/467,482, "Multivolume Devices, Kits, Related Methods for Quantification and Detection of Nucleic Acids and Other Analytes," filed on May 9, 2012; U.S. application Ser. No. 13/868,028, "Fluidic Devices and Systems for Sample Preparation or Autonomous Analysis," filed on Apr. 22, 2013; U.S. application Ser. No. 13/868,009, "Fluidic Devices for Biospecimen Preservation," filed on Apr. 22, 2013; and international application PCT/US13/63594, "Methods and Systems for Microfluidics Imaging and Analysis," filed on Oct. 4, 2013.

The term "or" as used herein is generally meant inclusively.

The term "about" as used herein means+/−10% of the recited value.

Reaction Chemistries

The process to be modulated can comprise one or more reactions, including but not limited to nucleic acid amplification, reverse transcription, digestion, cloning, ligation, hybridization, phosphorylation, dephosphorylation, glycosylation, deglycosylation, ubiquitination, deubiquitination, S-nitrosylation, denistrosylation, methylation, demethylation, N-acetylation, deacetylation, lipidation, proteolysis, sequencing, or signal generation.

Nucleic Acid Amplification

The process to be modulated can comprise nucleic acid amplification. Various nucleic acid amplification methods can be used. Modulation methods using restriction enzymes can use nucleic acid amplification methods wherein the amplification conditions allow the activity of the restriction enzyme to be preserved or partially preserved. The nucleic acid amplification method can comprise polymerase chain reaction (PCR), reverse transcription PCR (RT-PCR), quantitative PCR (qPCR), reverse transcription qPCR (RT-qPCR), nested PCR, multiplex PCR, asymmetric PCR, touchdown PCR, random primer PCR, hemi-nested PCR, polymerase cycling assembly (PCA), colony PCR, ligase chain reaction (LCR), digital PCR, methylation specific-PCR (MSP), co-amplification at lower denaturation temperature-PCR (COLD-PCR), allele-specific PCR, intersequence-specific PCR (ISS-PCR), whole genome amplification (WGA), inverse PCR, thermal asymmetric interlaced PCR (TAIL-PCR), or other methods including isothermal amplification methods. Isothermal amplification is a form of nucleic acid amplification which does not rely on the thermal denaturation of the target nucleic acid during the amplification reaction and hence may not require multiple rapid changes in temperature. Isothermal nucleic acid amplification methods can therefore be carried out inside or outside of a laboratory environment. A number of isothermal nucleic acid amplification methods have been developed, including but not limited to Strand Displacement Amplification (SDA), Transcription Mediated Amplification (TMA), Nucleic Acid Sequence Based Amplification (NASBA), Recombinase Polymerase Amplification (RPA), Rolling Circle Amplification (RCA), Ramification Amplification (RAM), Helicase-Dependent Isothermal DNA Amplification (HDA), Circular Helicase-Dependent Amplification (cHDA), Loop-Mediated Isothermal Amplification (LAMP), Single Primer Isothermal Amplification (SPIA), Signal Mediated Amplification of RNA Technology (SMART), Self-Sustained Sequence Replication (3 SR), Genome Exponential Amplification Reaction (GEAR) and Isothermal Multiple Displacement Amplification (IMDA). Further examples of such amplification chemistries are described in, for example, ("Isothermal nucleic acid amplification technologies for point-of-care diagnostics: a critical review, Pascal Craw and Wamadeva Balachandrana Lab Chip, 2012, 12, 2469-2486, DOI: 10.1039/C2LC40100B,") incorporated here in its entirety by reference. Isothermal amplification methods that operate at temperatures lower than PCR operating temperatures can be used, e.g., to improve compatibility of restriction enzymes with the amplification process if the restriction enzyme is not sufficiently stable under typical PCR operating temperatures. Furthermore, detection methods based on both signal amplification and target amplification, such as branched-DNA-based detection methodologies, can be used in this approach. For example, for branched-DNA-based detection methodologies, using an enzyme that can cleave the target in a position located between two positions used for binding of the capture extender and the label extender (e.g., as described in Tsongalis, Branched DNA Technology in Molecular Diagnostics, Am J Clin Pathol 2006; 126: 448-453), can reduce the signal obtained in the assay when a restriction enzyme recognizes and cleaves the target.

Reverse-transcription loop mediated isothermal amplification (RT-LAMP) can be used for nucleic acid amplification. RT-LAMP can be used in an assay, including qualitative and quantitative assays for nucleic acid detection, for example as shown in Examples 1-5, Example 8, or Example 9. An RT-LAMP assay can comprise detection of nucleic acids (such as HCV RNA) in at least one step, the test comprising at least one nucleic acid primer set capable of detecting nucleic acids (such as HCV RNA) in a RT LAMP based molecular test. An RT-LAMP assay use a primer set comprising, for instance, one pair of forward (FIP) and reverse (BIP) inner primers, and forward (F3) primer. An RT-LAMP assay can comprise using loop forward (LF) and/or loop back (LB) primers. An RT-LAMP assay can comprise using reverse (B3) outer primer. An RT-LAMP assay can comprise using LF primers that do not anneal or anneal weakly to a template, such as an HCV RNA template, at a temperature range applicable for reverse transcription, such as but not limited to 37-60° C. The temperature range can be optimized for the selected reverse transcription. This can be done, in some cases, by selecting the LF primers annealing place in a secondary structure rich fragment of HCV 5-UTR RNA template, so that the template self-complimentary duplex Tm for this annealing spot is in a range appropriate for RT-LAMP temperatures, (such as 58-67° C.). It may also be done, in some cases, by pre-annealing LF primers (before adding them to one-step RT-LAMP reaction mixture) with their complementary template-annealing inhibiting oligonucleotides (inhibitors), which, in turn, are 3' end modified to prevent their elongation by DNA polymerase. Such 3' end modifications of inhibitors may include but are not limited to Dideoxycytidine (ddC) or Inverted dT. Such an inhibitor may also contain some modified bases, which help to increase the Tm of the complex with LoopF primers up to temperatures appropriate for RT-LAMP, such as 58-67° C. An RT-LAMP assay can comprise loop forming primers where the 5' ends and/or 3' ends (both FIP and BIP) are complementary (or matching) to the target HCV secondary structure small and/or large loops in the 5' UTR of the HCV genome, such as, for example, to the domains II-IV loops in the 5' UTR HCV structures sequences. An RT-LAMP assay can comprise primers wherein Tm of the B2 annealing is higher than the Tm of its complementary template fragment secondary structures, including all the base pairing, hairpin and internal loops, budges and stuck pairs communicated in (but not limited to) the published HCV 5'UTR structure (see, e.g., "Christopher S. Fraser and Jennifer A. Doudna, Structural and mechanistic insights into hepatitis C viral translation initiation, Nature Reviews Microbiology 2007, 5: 29-38"). In some cases the net Tm (the temperature at which half of a template is bound by B2) is in a range applicable for reverse transcription with the used enzyme, including but not limited to 37-63° C. An RT-LAMP assay can comprise primers wherein the Tm of the B3 annealing is higher than the Tm of its complementary template fragment secondary structures for self-assembly, including all the base pairing, hairpin and internal loops, bulges and stuck pairs communicated in (but not limited to) the published HCV 5'UTR structure (see, e.g., "Christopher S. Fraser and Jennifer A. Doudna, Structural and mechanistic insights into hepatitis C viral translation initiation, Nature Reviews Microbiology 2007, 5: 29-38"). The net Tm (the temperature at which half of a template is bound by B3) is in a range applicable for reverse transcription with the used enzyme, including but not limited to 37-63° C. In some cases, an RT-LAMP assay can maximally decrease the probability of loopF primers annealing to RNA template and their subsequent participation as the primers in reverse transcription. In some cases, the RT primers (B2 part of BIP, B3 if used) and melting temperatures (TmB2 and TmB3) can be balanced to be higher than the melting temperature (Tm2) of the innate secondary structures of the corresponding parts of the HCV template, and the temperature of the reverse transcription step can be raised to be higher than Tm2 as well. The net Tm of B2 and B3 (if used) heteroduplexes with the template can be in a range applicable for reverse transcription with the used reverse transcriptase active enzyme. A reverse transcriptase which is still active at the temperature higher than Tm2 (including but not limited to 50-65° C.) can be used. In a one-step format, to ensure a detection of the majority of RNA templates present in reaction solution, the enzyme used for reverse transcription can have an RNase H activity, or a strong displacement activity. In some cases, the elongating ends of the priming sequences of BIP and FIP (which are 5' ends of B1c and F1c elongating as 3' ends of B1, F1; and 3' ends of B2 and F2) can be complementary to the secondary structures free fragments of the template at a chosen temperature applicable for LAMP, such as including but not limited to 57° C.-72° C.; as an example: the elongating ends of the loop's forming primers (both FIP and BIP in a LAMP reaction) can be placed to be complementary to the published HCV secondary structures' small or large loops in the 5' UTR of the HCV genome, such as, for example, to the domains II-IV loops in the 5' UTR HCV structures sequences.

Nucleic acid sequence based amplification (NASBA) can be used for nucleic acid amplification. If NASBA is used in combination with restriction enzymes, the restriction site can be between the forward and reverse primer, including the priming region. This approach is not necessarily limited to targeting a single restriction site. Multiple restriction sites on the same target nucleic acid can be targeted, either with one enzyme or with a mixture of several enzymes. Such multiple targeting can be used to enhance degradation of the target molecules. Such multiple targeting can be used to target multiple variants of the target molecule that might be present in the mixture being analyzed, when, for example, these multiple variants do not need to be differentiated in that analysis. In some cases, reactions can be performed on the 5' untranslated region (UTR) of the Hepatitis C Virus (HCV). This region is known to be highly conserved among genotypes of the virus, allowing the development of a single amplification reaction that amplifies, for example, a sequence of 230 basepairs in this region. In some examples, the sequences used for these reactions include, e.g., the universal forward primer (P1)

(Seq ID No: 1)
5'-_AATTCTAATACGACTCACTATAGGG_CAAGCACCCTATCAGGCAG

TA-3', the universal reverse primer (P2):5'-GTCTAGC-CATGGCGTTAGTA-3' (Seq ID No: 2), or the universal molecular beacon: 5'-/FAM/CGATCGAGCCAT-AGTGGTCTGCGGAACCGGTCGATCG/BHQ1/-3' (Seq ID No: 3) (DNA or RNA). In some cases, the oligonucleotide modulator specific for HCV Genotype 1 is GT1_antisense: 5'-AATCTCCAGGCAGTGtcgcc-3' (Seq ID No: 4), while the modulator specific for HCV Genotype 2 is GT2_antisense: 5'-GACCGGACATAGAGTaaatt-3' (Seq ID No: 5). The modulators can act to reduce and or inhibit amplification of the target. In this example, the T7 promoter sequence that is part of primer P1 is shown in italics and underlined and the stem sequence of the molecular beacon is indicated in bold. A universal set of primers can be designed to detect multiple or all HCV genotypes. A pre-incubation step (e.g., 2-5 min at 65° C. and cooling 10 min at 41° C.) can be included in NASBA protocols. The assay can lack pre-incubation. A NASBA enzyme mix can be made with thermostable enzymes, for example thermostable reverse transcriptase (e.g. RocketScript which may be purchased from Bioneer or MonsterScript from Epicentre), thermostable RNAse H (e.g. Hybridase Thermostable Rnase H which may be purchased from Epicentre or thermostable RNase H2 from IDT) and thermostable T7 RNA polymerase (e.g. Thermo T7 RNA polymerase which may be purchased from Toyobo). The optimum reaction temperature of these enzymes is around 50° C.—in some cases the reaction can be run at about 50° C. to improve the selectivity of annealing of primers (P1 and P2), molecular beacon (DNA or RNA) and specific oligonucleotide modulators (sense and antisense), and to decrease the free energy of secondary structures (kcal/mol).

Nucleic acid-based logic gates and DNA circuits can be used for nucleic acid amplification. The use of restriction enzymes with nucleic acid-based logic gates and DNA circuits can reduce or stop the intrinsic leakage problem for DNA networks. Combining the molecular recognition ability of both restriction enzymes and DNA networks, restriction enzyme logic gates can be highly active components for the design and construction of biocomputational devices (e.g., Qian and Winfree, Scaling Up Digital Circuit Computation with DNA Strand Displacement Cascades, Science 2011; 6034: 1196-1201).

Modulators

Modulators (e.g. inhibitors or promoters) can be used in conjunction with the methods disclosed herein. Modulators can comprise, for example, restriction enzymes, oligonucleotides, ligase enzymes, engineered or non-natural nucleases, nucleic acid modifying enzymes, artificial nucleic acids or nucleic acid analogs, modified bases, unnatural bases, or repair proteins. Modulators can be used to recognize specific sequences and slow or stop amplification reactions from occurring. In some examples, a restriction enzyme can be selected to cleave a sequence located between amplification primers, inhibiting amplification. In some cases, an oligonucleotide can be selected to interfere with or block primer binding, inhibiting amplification. Modulators can require activation; for example, a modulator can be inactive until activated by an enzyme. In one example, an oligonucleotide modulator is incapable or less capable of binding to the target nucleic acid until it is activated, such as by restriction enzyme digestion or ligase assembly.

Modulators can affect processes in different ways. A modulator can decrease or increase the rate of a reaction. In one example, a restriction enzyme can digest template or amplified nucleic acid molecules, slowing down an amplification reaction (e.g., reducing the rate of production of amplicons). In another example, a restriction enzyme can affect the structure of a nucleic acid molecule, allowing easier access to the amplicon and speeding up an amplification reaction (e.g., increasing the rate of production of amplicons). A modulator can decrease or increase the probability or chance that a given molecule will react, or will react sufficiently to be detected. For example, a restriction enzyme can digest a template nucleic acid molecule, preventing it from being amplified. A modulator can affect the efficiency of a reaction. Modulators can act by competing with the reaction or other process which they modulate. In one example, a restriction enzyme modulator can compete with an amplification reaction for the template nucleic acid molecule. In another example, an oligonucleotide can compete with nucleic acid amplification primers to bind to the nucleic acid molecule. Modulators can act prior to the process which they modulate. Modulators can act during the process which they modulate. Modulators can act after the process which they modulate.

Modulators can act on a nucleic acid molecule inside the priming region of a nucleic acid amplification (within, for example, a margin of one base). Modulators can act on a nucleic acid molecule outside the priming region of a nucleic acid amplification (within, for example, a margin of one base). Modulators can act on a nucleic acid molecule inside the amplicon region of a nucleic acid amplification (within, for example, a margin of one base). Modulators can act on a nucleic acid molecule outside the amplicon region of a nucleic acid amplification (within, for example, a margin of one base). Modulators can act by inhibiting off-target reactions, thereby promoting the primary reaction. Modulators can act on a nucleic acid molecule in a sequence-specific manner or in a sequence-targeted manner. For example, a restriction enzyme can recognize or target a specific sequence or range of sequences, or an oligonucleotide can selectively bind to a target sequence or range of sequences. Modulators can act on a nucleic acid in a modification-specific or modification-targeted manner. For example, an enzyme can affect nucleic acids in certain states of modification such as methylation or glycosylation.

Restriction enzymes can be used as modulators. A restriction enzyme can be type I, type II, type III, type IV, type V or an artificial restriction enzyme. A restriction enzyme can have digestion activity for double stranded DNA, single stranded DNA, or DNA:RNA hybrid molecules. A restriction enzyme can be thermally stable or not thermally stable. Restriction enzymes compatible with higher-temperature amplification and detection processes can be selected from those present in thermophilic organisms, or restriction enzymes with improved stability can be selected from those developed using in vitro selection and in vitro evolution processes. As of October 2013, the Restriction Enzyme Database (REBASE, New England BioLabs) contained over 3800 biochemically characterized restriction enzymes. Of over 3600 Type II REs, over 580 are commercially available, including over 220 distinct specificities from a total of over 250 total specificities known. The availability of restriction enzymes allows a wide range of sequences to be targeted as a restriction site.

In some cases, the restriction site can be selected to be located between the primer sequences used for amplification. It can be selected to exert an improved or optimized inhibitory effect on the amplification reaction. For example, when LAMP is used for amplification, the restriction site can be between the B3 primer and the F3 primer (e.g., see Example 1). In another example, when RPA is used, the restriction site can be between the forward primer and the reverse primer, including the priming region. In another example, when NASBA is used, the restriction site can be between the forward and reverse primer, including the priming region. This approach is not limited to targeting a single restriction site. Multiple restriction sites on the same target nucleic acid can be targeted, either with one enzyme or with a mixture of several enzymes. Such multiple targeting can be used to enhance degradation of the target molecules, or to target multiple variants of the target molecule that might be present in the mixture being analyzed, if, for example, these multiple variants do not need to be differentiated in that analysis.

In some cases, the restriction enzyme can also be used outside the priming region. For example, a restriction enzyme can be used to dissociate the secondary structure of RNA and promote the amplification process. In such cases, restriction enzyme activity can be used to promote amplification and detection reactions. Methods, devices, and approaches discussed herein are not limited to inhibiting or stopping reactions, but can also be used to promote amplification and detection reactions. For example, a restriction enzyme digestion can be incorporated into a NASBA reaction to digest out of the amplicon (off-target) regions or products, decreasing the amount of non-specific product and enhancing the reaction. Restriction enzymes with a target sequence not included in the amplified product can be used to omit the recommended pre-incubation step for NASBA.

Artificial restriction enzymes such as zinc-finger nucleases (ZFNs) (see, e.g., "F. D. Urnov, J. C. Miller, Y. L. Lee, C. M. Beausejour, J. M. Rock, S. Augustus, A. C. Jamieson, M. H. Porteus, P. D. Gregory and M. C. Holmes, Highly efficient endogenous human gene correction suing designed zinc-finger nucleases, Nature, 2005, 435, 646-51"), transcription activator-like effector nucleases (TALENs) (see, e.g., "M. Christian, T. Cermak, E. L. Doyle, C. Schmidt, F. Zhang, A. Hummel, A. J. Bogdanove and D. F. Voytas, Targeting DNA double-strand breaks with TAL effector nucleases, Genetics, 2010, 186, 757-61"), meganucleases (see, e.g., "G. Silva, L. Poirot, R. Galetto, J. Smith, G. Montoya, P. Duchateau and F. Paques, Meganucleases and other tools for targeted genome engineering: perspectives and challenges for gene therapy, Curr Gene Ther, 2011, 11: 11-27"), or RNA-guided engineered nucleases via Cas9 (RGENs) (see, e.g., P. Mali, L. Yang, K. M. Esvelt, J. Aach, M. Guell, J. E. DiCarlo, J. E. Norville and G. M. Church, RNA-guided human genome engineering via Cas9, Science, 2013, 339: 823-6 and J. M. Kim, D. Kim, S. Kim" and "J. S. Kim, Genotyping with CRISPR-Cas-derived RNA-guided endonucleases, Nat Commun, 2014, 5, 3157") can be used to target identified genetic markers.

At least three types (I-III) of clustered short palindromic repeats (CRISPR) systems have been identified across a wide range of bacterial hosts and can be used as modulators. Type I and III systems use a specialized CRISPR-associated nuclease (Cas) that processes the precursor CRISPR RNA (pre-crRNA), and once mature, each crRNA assembles into a large multi-Cas protein complex capable of recognizing and cleaving nucleic acids complementary to the crRNA. In contrast, type II CRISPR process pre-crRNAs by a different mechanism in which a trans-activating crRNA (tracrRNA) complementary to the repeat sequences in pre-crRNA triggers processing by the double double-stranded (ds) RNA-specific ribonuclease RNase II in the presence of Cas9 protein. Following the hybridization between the two non-coding RNAs, Cas9 is targeted to the genomic loci matching a 20 nucleotide guide within the crRNA, immediately upstream of a 5'NGG protospacer adjacent motif (PAM). crRNA and tracrRNA can be fused to generate a chimeric single-guide RNA (sgRNA) that mimics the natural crRNA-tracrRNA hybrid. Both crRNA-tracrRNA duplexes and sgRNA can be used to target Cas9 for multiplexed genome editing. The methodologies described herein can include the use of the CRISPR system to affect the processes of detection or amplification. Methodologies can include the use of Cas9 or its homologues or functional analogues, such as crRNA and tracrRNA or sgRNA (origin of RNA includes the one made in situ or ex situ by in vitro transcription) to control nucleic acid amplification processes in a sequence specific manner, where the activity of Cas9 can be preserved or partially preserved under the conditions of amplification or detection. In some examples, the specificity of the Cas9-crRNA-tracrRNA or Cas9-sgRNA complexes can be modified by matching the sequence of the crRNA with the target of interest. In some examples, these elements could be combined with a detection or an amplification scheme to identify, detect or differentiate nucleic acid sequences. In some examples, by mixing these three elements in a PCR reaction, together with the DNA or RNA template, the PCR product can be cleaved while amplification is occurring, changing the outcome of the reaction (e.g., including but not limited to: from positive to negative, delayed time to positive or less number of counts in digital format) and avoiding additional steps which other methods, such as RFLP, can entail. This cleavage can occur, for example, based on a specific single nucleotide polymorphism (SNP) and the sequence surrounding it. Isothermal amplification methods (e.g., NASBA, LAMP, RPA, RCA) can have high compatibility with Cas9 systems during the process of amplification and can be used. In some examples, the use of engineered Cas9-crRNA-tracrRNA can overcome the limited availability of restriction endonuclease sites.

Ligase enzymes can be used as modulators, including as inhibitors or promoters. For example, a ligase enzyme can ligate two nucleic acid molecules, allowing subsequent amplification of the ligated product. A ligase enzyme can ligate two nucleic acid molecules, promoting a folding of the ligated product with inhibits, prevents, promotes, or enables subsequent amplification.

Oligonucleotides can be used as modulators, including as inhibitors ("oligos" or "oligo inhibitors"). Recognition, hybridization and blocking of a specific sequence by an oligonucleotide can be used to stop or delay a reaction of interest. The use of oligonucleotides is not limited to inhibition of reactions, and can also be used to enhance certain reactions, for example by affecting the secondary structure of a nucleotide target, or by inhibiting off-target reactions. Oligonucleotides can comprise synthetic or naturally produced nucleic acid molecules. Modified nucleic acids or nucleic-acid-like structures (e.g., peptide nucleic acids or PNAs) can also be used, which can also be referred to as "oligos" or "oligo inhibitors." In some examples, an oligonucleotide inhibitor binds more tightly or faster to the target template or intermediate product than, for example, the primers in the amplification reaction. These oligonucleotides can be longer than primers used for amplification. These oligonucleotides can contain bases with or without modifications that bind more tightly to the target. These oligonucleotides can be designed with special structures (e.g., toe-hold structures), such as those used to facilitate, accelerate or improve the specificity of DNA origami, DNA self-assembly, or DNA circuits. The specificity of inhibitors can be controlled or altered, in some examples, by the sequence of the oligonucleotides, which can be tuned by a number of methods, including by altering the percentage of matches between inhibitors and template, or primers and template. The oligonucleotides can, in some cases, include some modifications (e.g., locked nucleic acid (LNA) or dideoxynucleotides (ddNTPs)), to increase the specificity, change the annealing temperature, or produce a stronger inhibition effect. If the priming region is targeted, the oligonucleotide inhibitor can be chosen to bind more tightly or faster to the target template or intermediate product (for example, it be longer than primers used for amplification, or contain bases with or without modifications that bind more tightly to the target) than the primers in the competition. The specificity of the inhibitors can be controlled by the sequence of the oligonucleotide, which can be tuned by a number of methods, including by altering the percentage of matches between inhibitors and template, or primers and template. The oligonucleotides could include some modifications (e.g., LNA, ddNTPs) to increase the specificity, change the annealing temperature, or produce a stronger inhibition effect.

Oligonucleotides can comprise peptide nucleic acid (PNA). Peptide nucleic acid is a type of nucleic acid analogue that replaces the sugar phosphate backbone with N-(2-amino-ethyl)-glycine units. Due to the fact that the backbone is uncharged, unlike DNA, the thermal stability of a PNA:DNA duplex is higher than that of dsDNA. It is also resistant to hydrolytic (enzymatic) cleavage and typically cannot be recognized by polymerase as a primer from which to extend. PNA-directed PCR clamping and selective inhibition by PNA in an isothermal amplification system can be used with the methodologies described herein. The following publications are incorporated here by reference in their entireties for all purposes: "Drum, H., P. E. Nielsen, M. Egholm, R. H. Berg, O. Buchardt, and C. Stanley, Single base pair mutation analysis by PNA directed PCR clamping, Nucleic Acids Res 1993, 21(23): 5332-5336," "K Tatsumi, Y Mitani, J Watanabe, H Takakura, K Hoshi, Y Kawai, T Kikuchi, Y Kogo, A Oguchi-Katayama, Y Tomaru, H Kanamori, M Baba, T I shadao, K Usui, M Itoh, P E Cizdziel, A Lezhava, M Ueda, Y Ichikawa, I Endo, S Togo, H Shimada, and Y Hayashizaki, Rapid screening assay for KRAS mutations by the modified smart amplification process, J Mol Diagn 2008, 10(6): 520-526," "Jae-jin Choi, Chunhee Kim, and Heekyung Park, Peptide nucleic acid-based array for detecting and genotyping human papillomaviruses. J Clin Microbiol 2009, 47(6): 1785-1790," and "Lizardi, P. M. (1993) Rolling circle replication reporter systems, Yale University, U.S. Pat. No. 7,618,776 B2." Together with some nucleases (e.g., 51 nuclease), PNA can function as an artificial restriction enzyme by the invasion mechanism to dsDNA of PNA and degradation by nuclease of the generated ssDNA part, (see, e.g., "A. Ray and B. Norden, Peptide nucleic acid (PNA): its medical and biotechnical applications and promise for the future, FASEB J 2000, 14: 1041-1060"). In some examples, this approach can be used in combination with one or more isothermal amplification chemistry. This approach can be used with a variety of target nucleic acids (ssDNA, RNA, dsRNA or dsDNA). Using PNA as a diagnostic tool for genotyping and subtyping (e.g., of influenza) can be conducted qualitatively or quantitatively. The materials and methods described in ("K Kaihatsu, S Sawada, and N Kato, Rapid Identification of Swine-Origin Influenza A Virus by Peptide Nucleic Acid Chromatography, Antivirals & Antiretrovirals 2013, 5(4): 077-079") can be used in combination with the methodologies described herein.

Oligonucleotides (e.g., unmodified oligonucleotides such as RNA and DNA, and modified oligonucleotides such as PNA and LNA) can be used alone or in combination with certain enzymes (e.g., genome editing engineered nucleases or methylase) as modulators, to tune the process of amplification in a sequence-specific manner. This can allow targeting new emerging targets while retaining the assay setup, and the high throughput in screening different sequences, which could facilitate pandemic disease monitoring and epidemiological surveillance, for example in the case of influenza A genotyping/subtyping.

Oligonucleotide modulators can be used in combination with RNase H to modulate a nucleic acid amplification reaction. For example, a sequence-specific DNA oligonucleotide modulator (e.g., an inhibitor) complementary to an RNA template or product RNA (e.g., antisense RNA produced by NASBA reaction), can anneal to a target nucleic acid and generate a DNA/RNA hybrid recognizable by RNase H. RNase H can be used to cleave the RNA strand from a heteroduplex. This oligonucleotide modulator-guided cleavage can prevent further amplification of the RNA strand, changing rate of the reaction or final number of amplified molecules ("fate"). The guide-RNase H can be used to target specific sequences within a sequence targeted by a variety amplification reactions, including but not limited to Recombinase Polymerase Amplification (RPA), Loop-mediated isothermal amplification (LAMP), Helicase-dependent amplification (HAD), Strand displacement amplification (SDA), and Nicking enzyme amplification reaction (NEAR).

RNA molecular beacons can be used as modulators. For example, an RNA molecular beacon and an increased concentration of RNase H can be used to increase the efficiency of a NASBA reaction. NASBA makes use of RNase H to degrade the RNA/DNA heteroduplex created by reverse transcription, enabling the hybridization of additional primers and the generation of double-stranded DNA. Therefore, higher RNase H concentration can benefit the performance of NASBA reaction because the described steps will proceed more rapidly. The amount of RNase H can be limited because of the presence of sequence specific DNA molecular beacons, which can hybridize to a NASBA product (e.g. antisense RNA) generating a DNA/RNA heteroduplex that can be recognized and cleaved by the RNase H. At high concentration this cleavage of the NASBA product decreases the efficiency of the reaction. In order to increase efficiency of NASBA reaction while avoiding undesired cleavage an RNA molecular beacon can be used, allowing an increased amount of RNase H. A thermostable RNase H can be used, e.g, to avoid losing activity during steps with elevated temperature (e.g. pre-incubation of NASBA reaction). The binding of primers to RNA templates can produce a DNA/RNA heteroduplex detectable by RNase H. In some examples, this modified NASBA reaction can make use of RNA-containing primers P1 or P2 to prevent the RNase H mediated degradation of template due to primer annealing. A modulator can be a non-specific nuclease that cleaves RNA.

Figure 4:
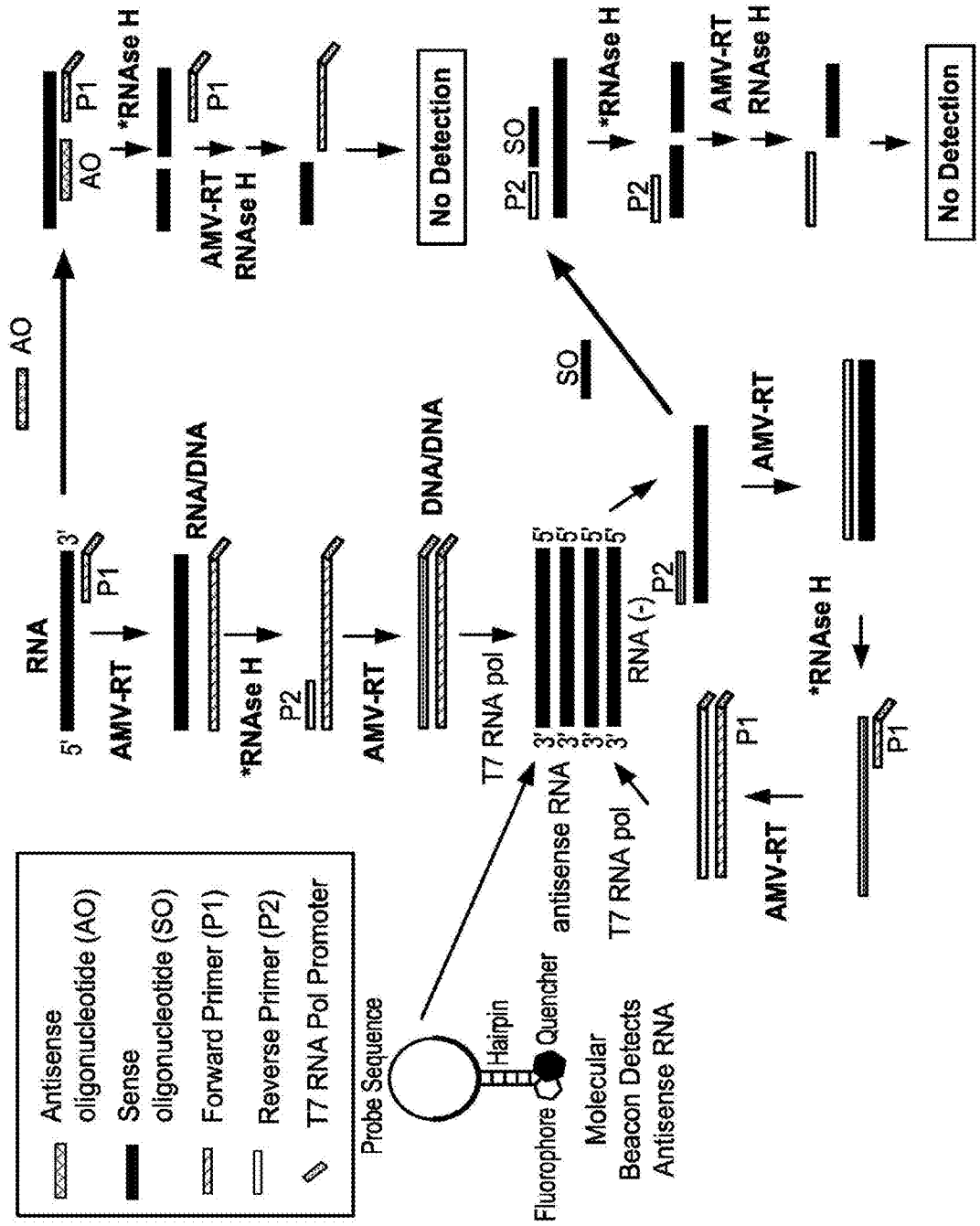
FIG. 4 shows an exemplary schematic of a NASBA amplification reaction.

The enzyme RNase H is a non-specific nuclease that cleaves RNA. RNase H's ribonuclease activity cleaves the 3'-O—P bond of RNA in a DNA/RNA duplex to produce 3'-hydroxyl and 5-phosphate terminated products. Therefore, RNAse H can be used as a modulator of an amplification reaction by cleaving the RNA template or by cleaving the generated RNA product (e.g., in a NASBA reaction). Other RNA- and DNA-cleaving enzymes can be used as well. FIG. 4 shows an exemplary schematic of a NASBA amplification reaction with the P1 (antisense)-P2 (sense) primer set. The overhang on the P1 encodes the promoter sequence for the T7 RNA polymerase. A molecular beacon with a fluorophore and a quencher with the NASBA amplification reaction can generate a real-time detection system. Antisense oligonucleotide (AO) modulator guides RNase H to specifically cleave RNA template while sense oligonucleotide (SO) modulator guides RNase H to specifically cleave generated antisense RNA. Antisense oligonucleotide (AO) modulator and sense oligonucleotide (SO) modulator can be used individually or in combination. DNA or RNA molecular beacons target antisense RNA In some cases, in order to modulate the reaction in a sequence specific manner, the amplification system can be modified by the incorporation of RNAse H and an oligonucleotide modulator complementary to the targeted RNA. In some examples, this oligonucleotide can anneal to the target RNA strand, and in some examples it can generate a DNA/RNA hybrid that will be recognized by the RNAse H, cleaving the RNA template and consequently reducing the initial amount of template that would proceed to a successful amplification (Antisense Oligonucleotide (AO), FIG. 4). In some cases, the oligonucleotide modulator can target the produced RNA (e.g., antisense RNA) and can slow down the reaction (Sense Oligonucleotide (SO), FIG. 4). In some examples, the combination of a specific oligonucleotide modulator together with a non-specific nuclease can generate a guide-RNase H that can be used to specifically target a sequence of interest. In order to cleave the RNA, RNAse H needs a DNA/RNA hybrid with 4 or more nucleotides perfectly matched (see, e.g., "Donis-Keller H. Site specific enzymatic cleavage of RNA. Nucleic Acids Res. 1979 Sep. 11; 7(1):179-92"). This property can be used to identify single nucleotide point mutations. For example, in some cases an oligonucleotide modulator of 7 bases can be designed to target a sequence where a SNP (single nucleotide polymorphism) could be present in the 4th position; the oligonucleotide can hybridize under correct reaction conditions in the presence or absence of the SNP, but RNAse H activity can be limited due to the absence of the SNP. A perfectly matching RNA/DNA hybrid can be cleaved, preventing amplification of the template, while the presence of a SNP can prevent RNAse H activity, allowing amplification as normal. Other enzymes that are sensitive to matched or mismatched hybridization products can be used similarly, including enzymes that detect one or more modifications of one or more of nucleic acid bases. The units of RNase H typical NASBA reactions can be limited because readout can be tied to the presence of specific DNA molecular beacons (oligonucleotide hybridization probes that can report the presence of specific nucleic acid) which hybridize to the major NASBA product, antisense RNA, generating a DNA/RNA heteroduplex. In such cases, at high concentrations, RNase H can cleave the RNA and the efficiency of the reaction can be reduced. Increasing the amount of RNase H can benefit the performance of the reaction because steps in which RNAse H is involved (indicated with an asterisk, FIG. 4) will proceed more rapidly; however this can be balanced with the cleavage induced by the presence of DNA molecular beacon. In some examples, in order to increase RNAseH concentration and positively affect efficiency of guided-RNAse H, the NASBA reaction can be modified in one or more of the following ways: (i) increase the amount of RNase H; (ii) select a thermostable RNAseH to avoid losing activity during pre-incubation of NASBA reaction; (iii) incorporate an RNA molecular beacon to avoid undesired cleavage promoted by the DNA probe/RNA antisense hybrid. As a result of this change to an RNA beacon, in modified NASBA, reaction efficiency can be improved. In addition, the competition between the concentrations of molecular beacons in the system with the RNAse H activity can be reduced or eliminated. As a result, greater quantities of the RNA based molecular beacon can be added to increase the fluorescent intensity of the product. In another example, the Guide-RNase H system can be used to increase the specificity or accuracy of amplification reactions. By incorporating oligonucleotides that cannot hybridize to the target sequence for amplification, but rather to off-target NASBA products, these side-reactions can be selectively inhibited. In addition, it is possible to generate oligonucleotides that differ from conserved template regions by enough bases to prevent annealing at reaction temperatures. The activity of RNase H can then prevent the accumulation of errors in these regions. For example: NASBA is known to suffer from the amplification of off-target sequences due to its use of error-prone T7 polymerase and AMV reverse transcriptase. As a result, off-target oligonucleotides can be targeted this way to the region of a molecular beacon thus preventing the amplification of products undetectable by the beacon. In another example, this inhibition of non-specific product can be caused not by the use of the Guide-RNase H system but rather by the use of restriction enzymes. In one example, the restriction enzyme ApoI was shown to recover the specificity of a NASBA reaction performed without a pre-incubation step.

Repair proteins (e.g., MutH, MutL, and MutS) can be used to produce a sequence specific interference or inhibition of a nucleic acid amplification system: For example, the *Escherichia coli* methyl-directed DNA mismatch repair system (see, e.g., "Smith, J. and P. Modrich, Mutation detection with MutH, MutL, and MutS mismatch repair proteins. Proc Natl Acad Sci USA 1996, 93(9): 4374-4379") can identify and repair base-base mispairs and up to three nucleotide insertion/deletion mismatches. Repair is initiated by binding of MutS to the mispair. Binding of MutL to this complex results in activation of MutH (ATP-dependent activation of endonuclease activity), which incises the heteroduplex at d(GATC) sequences in the vicinity of the mispair. In some examples, combining the complex MutHLS or using one of these three proteins together with a nucleic acid amplification system can produce sequence-specific interference of the system. MutS is able to suppress a nucleic acid extension reaction by binding specifically to a mismatched base pair (see, e.g., Hayashizaki, Y; Itoh, M.; Usui K.; Kazuhito M.; and Kanamori H., Novel MutS protein and method of using same to determine mutations, 2011, Patent number EP 2 371 951 A1). This approach is not limited to these specific proteins; rather, other proteins with related functional activities can be used instead or in addition to these proteins.

Chemical modification of nucleic acids can be used to modulate nucleic acid amplification. For example, a DNA intercalator modified with an azide group (e.g., propidium monoazide (PMA)) or other cross-linking group can be used as a modulator, inducing modification of DNA that can interfere with amplification or detection reactions. Providing both a chemical modifier and reagents for amplification or detection reactions can allow competition between the modification reaction and the amplification or detection reaction. Chemically modified probes (e.g., oligonucleotides, PMA, or other probes described herein), similarly modified with azide or other cross-linking groups, can provide specificity in associating with a target nucleic acid and modulating (e.g., inhibiting) amplification or detection reactions. Similarly, these approaches can be used to enhance association between a primer and a target nucleic acid, promoting amplification.

Assays

The devices and methods described herein can be applied for assays to detect genetic variation, including differences in genotypes, ranging in size from a single nucleotide site to large nucleotide sequences visible at a chromosomal level. Such genotype or polymorphism analysis can be used for applications including but not limited to early diagnosis, prevention and treatment of human diseases; systematics and taxonomy; population, quantitative, and evolutionary genetics; plant and animal breeding; identifying individuals and populations (paternity and forensic analysis), infectious disease diagnostics and monitoring and surveillance, epidemiology. Examples of some applications of inventions described herein are provided herein. These applications are not limited to the use of any of the methods described herein may be used for these applications, including those using different modulators (e.g., restriction enzymes or oligonucleotides), including inhibitors or promoters.

An assay can comprise conducting a reaction (e.g., amplification) on a reagent (e.g., nucleic acid) in the presence of a modulator (e.g., restriction enzyme) and comparing the results of the reaction (e.g., reaction rate, reaction efficiency, reaction outcome, positive or negative signal generation) to a reaction conducted without a modulator. This can reveal a difference in reaction outcome, indicating the presence or identity of a reagent which is affected by the chosen modulator. An assay can comprise conducting a reaction (e.g., amplification) on a reagent (e.g., nucleic acid) in the presence of a modulator (e.g., restriction enzyme) and comparing the results of the reaction (e.g., reaction rate, reaction efficiency, reaction outcome, positive or negative signal generation) to a reaction conducted on a different reagent. This can reveal a difference in the effect of the modulator on the two different reagents, indicating the identity of the reagents or of the modulator. An assay can comprise conducting multiple reactions (e.g., amplification) on a reagent (e.g., nucleic acid) in the presence or absence of a modulator (e.g., restriction enzyme) or multiple modulators; the pattern of reaction outcomes in the presence or absence of each modulator can be used to generate a pattern or "fingerprint." This pattern can be compared to one or more reference patterns indicating a particular reagent (e.g., a nucleic acid with a particular genotype), allowing identification of the reagent. Modulators can be provided before, during, or after various sample handling steps, sample preparation steps, or reaction steps. The above assays can be extended to 2, 3, 4, 5, 6, 7, 8, 9, 10, 15, 20, 25, 30, 35, 40, 45, 50, 55, 60, 65, 70, 75, 80, 85, 90, 95, 100, or more different reagents, modulators, or both.

Figures 3A, 3B, 3C, 3D:
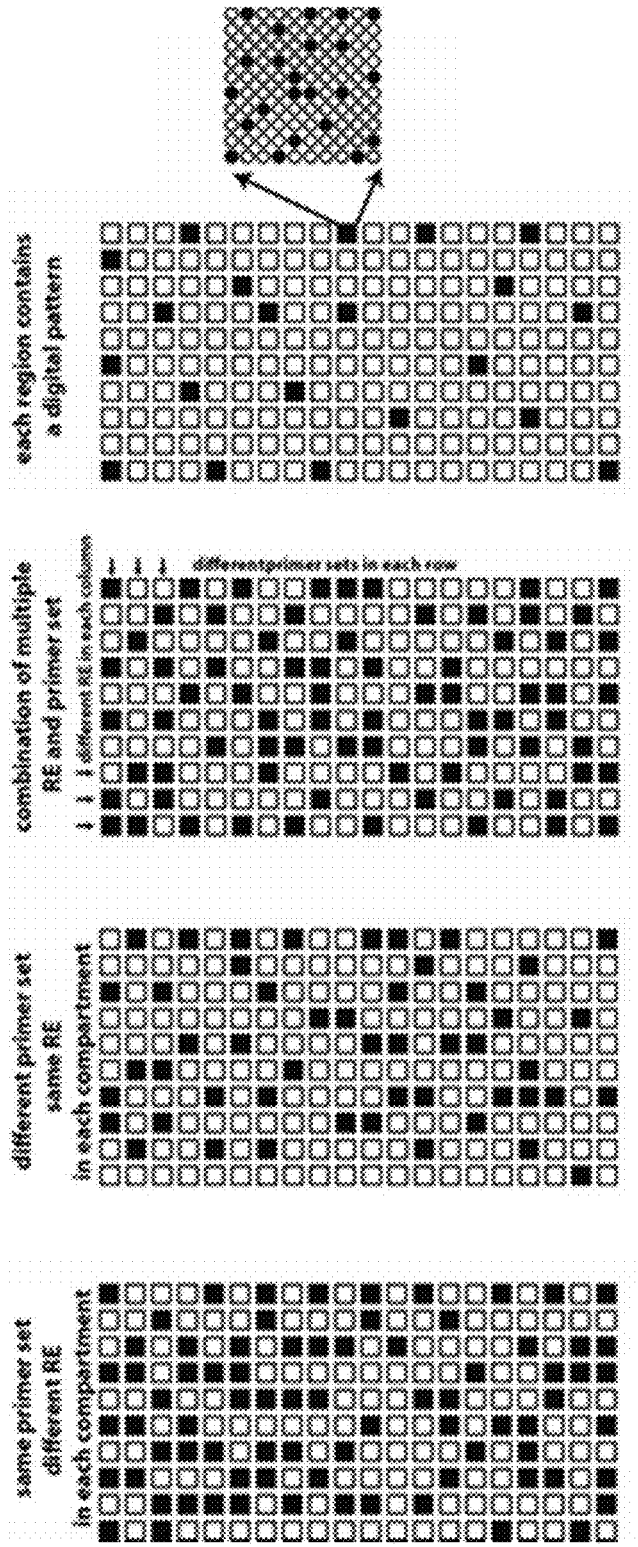
FIG. 3A shows an exemplary schematic of an assay comprising the same primer set and a different restriction enzyme in each compartment.
FIG. 3B shows an exemplary schematic of an assay comprising a different primer set and the same restriction enzyme in each compartment.
FIG. 3C shows an exemplary schematic of an assay comprising a different restriction enzyme in each column of compartments and a different primer set in each row of compartments.
FIG. 3D shows an exemplary schematic of each compartment further divided into smaller compartments to perform digital amplification or detection.

Modulators (e.g., restriction enzymes or oligonucleotides), either promoters or inhibitors, can be used in conducting multiplexed measurements. For example, when multiple variants (e.g., genotypes of the HCV virus) need to be differentiated, multiple restriction enzymes can be chosen to selectively target amplicons arising from these genotypes. These reactions can be, for example, performed in separate compartments for each enzyme or enzyme mixture, as described elsewhere in this application for multiplexed measurements. A sufficient number of restriction enzymes of sufficiently different selectivity can be chosen such that each variant can be uniquely identified. For example, the number of enzymes used can be equal to or larger than the number of variants to be differentiated and identified, although this is not always required. In some examples, a cascade that processes samples sequentially through several conditions can be applied to provide higher throughput. One reaction can run through multiple steps for short amount of time, and then the reaction result can be read out only at the last step of the cascade, or the result for all steps can be read out at once at the end of the cascade. The restriction enzyme can be deactivated at the end of each step of the cascade. The system can be designed in a way (e.g., by using different primers for each condition) that only when the target is specific to a certain combination of enzymes is a positive readout generated in the last step. Thus the spatial multiplexing of restriction enzymes, such as in FIG. 3, can be transferred to temporal multiplexing. FIG. 3 shows exemplary nucleic acid profiling panels. FIG. 3A shows one set of universal primers or amplification chemistry with different restriction enzymes in each compartment. FIG. 3B shows one type of restriction enzyme with different sets of primers or amplification chemistries in each compartment. FIG. 3C shows multiple sets of primers or amplification chemistries with multiple restriction enzymes. FIG. 3D shows each compartment further divided into smaller compartments to perform digital amplification or detection, where one smaller compartment only contains one molecule or no molecule. White spots represent positive reactions (e.g., the restriction enzyme does not substantially recognize any target sequence and does not significantly influence the reaction rate), while the black spots represent negative reactions (e.g., the restriction enzyme recognizes a target sequence in the amplicon and so the reaction is delayed or stopped). Each species or genotype assayed can generate a specific nucleic profile or "fingerprint" corresponding to its identity. This exemplary assay can also be implemented using other modulators, such as oligonucleotides. This highly multiplexed panel can be performed in any format comprising confined volumes, for example, on a well plate, in a SlipChip device (e.g., Feng Shen, Wenbin Du, Elena K. Davydova, Mikhail A. Karymov, Janmaj ay Pandey, and Rustem F. Ismagilov, Nanoliter Multiplex PCR Arrays on a SlipChip, Analytical Chemistry 2010; 82:4606-4612), in an emulsion droplet system (e.g., RainDance or Quantalife systems), or functionalized bead (e.g., BeadArray or Luminex systems).

Assays can comprise genetic fingerprinting (e.g., DNA testing, DNA typing or DNA profiling). This methodology can use the individuality of DNA molecules to distinguish between organisms or to show the relationships between them. For example, restriction fragment length polymorphism (RFLP) analysis can be used for genetic fingerprinting. Detecting RFLPs involves fragmenting a sample of DNA by a restriction enzyme, which can recognize and cut DNA wherever a specific short sequence occurs. The resulting DNA fragments can then be separated by length, for example through an agarose gel electrophoresis, and analyzed, for example by transfer to a membrane via the Southern blot procedure followed by hybridization of the membrane to a labeled DNA probe to determine the length of the fragments which are complementary to the probe. An RFLP occurs when the length of a detected fragment varies between individuals and can be used in genetic analysis. Assays disclosed herein can produce a distinct pattern based on the generation of a specific amplicon and the combination of different restriction enzymes during the amplification method, for example as shown in FIG. 3. This methodology does not require post-amplification treatment for the readout and can generate a specific identity or fingerprint for each analyzed target. Using a panel comprising one or more preloaded restriction enzymes can be used to generate a DNA profile for a specific amplicon or amplicons. Exemplary applications of this assay include epidemiological surveillance (for example, microbiological typing systems for *Salmonella* spp., *Escherichia* spp., *Staphylococcus* spp., *Campylobacter* spp., *Listeria* spp. and others); bacterial species are grouped showing maximal similarity phenotypic and genotypic characters, however species may often be subdivided ("typed") on the basis of characters of a single class (e.g., biotyping, serotyping, phage typing, bacteriocin typing) and practical use of this can be made to obtain information about sources and routes of infection (epidemiological surveillance). Other applications include characterization of genetic patterns associated to health or diseases status (e.g., cancer), detection of drug resistance mutations (e.g., HIV and HCV), and identification of antibiotic resistance (e.g., Methicillin-resistant *Staphylococcus aureus* (MRSA)) can be accomplished using the methodologies described herein.

An assay can comprise conducting one or more reactions on a target and observing reaction results. For example, an assay can comprise combining reagents for two different reactions with a target shared by both reactions, and observing the outcome of the competing reactions. The outcome can be observed and used to determine information about one or more of the conducted reactions, such as reaction rate or reaction efficiency.

Assays can be conducted in a digital format, that is, assays can be conducted on a sample divided into partitions containing one or zero target molecules (e.g., nucleic acid molecules). In some cases, some partitions can contain more than one target molecule; in some cases, the majority of partitions contain one or zero target molecules. This digital or single molecule format can be used in conjunction with assays described herein, including identification, detection, genotyping, SNP detection, rare allele detection, and quantification of nucleic acids. Modulation, including inhibition, of a reaction at single molecule level can be different from that at bulk level. For example, in the case of inhibition by restriction enzyme, in bulk reaction, a molecule that is not inhibited or is less inhibited can cause amplification or detection, thus lead to a positive of the entire mixture. In a digital single molecule format, such a molecule will be confined, for example, to a single partition or compartment, leading to a positive in that single compartment. Results can be presented in a binary format (e.g., yes/no, on/off), with each partition either giving rise to a signal or not giving rise to a signal (e.g., an indicator or readout reaches or does not reach a chosen threshold value). By performing the reaction in digital format, it is possible to translate a kinetic difference in amplification between into probability difference (e.g., an increased or decreased probability that a single sample molecule present in a partition will be amplified), as shown for example in FIG. 10, allowing the binary results from the partitions to be read or collected with an end-point measurement. Quantitative results can also be obtained from digital assays, allowing both genotyping and quantification of viral load, for example. Quantitative results can also be obtained from a sample with more than type of one target nucleic acid present, allowing analysis of a population distribution between targets. Real-time monitoring during the reaction can be used, alone or in combination with digital or binary format results, to observe a kinetic difference in amplification between samples. Real-time digital analysis can provide information on the rate of individual amplification reactions, on the distribution and the heterogeneity of the rate of the amplification reactions, and on the number of successful amplification reactions. This information, in combination with the methods and reagents described herein, can be used to enhance the quality of nucleic acid analysis or detection. For example, real time digital analysis can be used to analyze HCV genotyping RT-LAMP reactions. Real-time digital analysis is not required for all cases, and end-point digital analysis can be sufficient. In end-point digital analysis, as described above, a single measurement of the extent of reaction is obtained for the partitions or compartments of interest, and used for analysis. Assays can also be performed in a quasi-digital format, which is similar to the digital format described above except that more than one copy of a target (e.g., 2, 3, 4, 5, 6, 7, 8, 9, 10, 15, 20, 25, 30, 35, 40, 45, 50, or more copies of a target) can be present in a single partition. In some cases, more than one copy of a target can be present in the majority of partitions. Nonetheless, each partition either generates a positive or a negative signal, and results can be analyzed similarly to a digital assay.

Examples of digital amplification and examples of genotyping applications are described in the following patents and papers incorporated here by reference in their entirety: U.S. Application 61/516,628, "Digital Isothermal Quantification of Nucleic Acids Via Simultaneous Chemical Initiation of Recombinase Polymerase Amplification (RPA) Reactions on Slip Chip," filed on Apr. 5, 2011; U.S. Application 61/518,601, "Quantification of Nucleic Acids With Large Dynamic Range Using Multivolume Digital Reverse Transcription PCR (RT-PCR) On A Rotational Slip Chip Tested With Viral Load," filed on May 9, 2011; U.S. application Ser. No. 13/257,811, "Slip Chip Device and Methods," filed on Sep. 20, 2011; international application PCT/US2010/028361, "Slip Chip Device and Methods," filed on Mar. 23, 2010; U.S. Application 61/262,375, "Slip Chip Device and Methods," filed on Nov. 18, 2009; U.S. Application 61/162,922, "Sip Chip Device and Methods," filed on Mar. 24, 2009; U.S. Application 61/340,872, "Slip Chip Device and Methods," filed on Mar. 22, 2010; U.S. application Ser. No. 13/440,371, "Analysis Devices, Kits, And Related Methods For Digital Quantification Of Nucleic Acids And Other Analytes," filed on Apr. 5, 2012; and U.S. application Ser. No. 13/467,482, "Multivolume Devices, Kits, Related Methods for Quantification and Detection of Nucleic Acids and Other Analytes," filed on May 9, 2012; U.S. application Ser. No. 13/868,028, "Fluidic Devices and Systems for Sample Preparation or Autonomous Analysis," filed on Apr. 22, 2013; U.S. application Ser. No. 13/868,009, "Fluidic Devices for Biospecimen Preservation," filed on Apr. 22, 2013; and international application PCT/US13/63594, "Methods and Systems for Microfluidics Imaging and Analysis," filed on Oct. 4, 2013; Feng Shen, Wenbin Du, Jason E. Kreutz, Alice Fok, and Rustem F. Ismagilov, "Digital PCR on a SlipChip," Lab Chip 2010 10: 2666-2672; Feng Shen, Elena K. Davydova, Wenbin Du, Jason E. Kreutz, Olaf Piepenburg, and Rustem F. Ismagilov, "Digital Isothermal Quantification of Nucleic Acids via Simultaneous Chemical Initiation of Recombinase Polymerase Amplification Reactions on SlipChip," Analytical Chemistry 2011 83:3533-3540; Feng Shen, Bing Sun, Jason E. Kreutz, Elena K. Davydova, Wenbin Du, Poluru L. Reddy, Loren J. Joseph, and Rustem F. Ismagilov, "Multiplexed Quantification of Nucleic Acids with Large Dynamic Range Using Multivolume Digital RT-PCR on a Rotational SlipChip Tested with HIV and Hepatitis C Viral Load," JACS 2011 133: 17705-17712; Christina Fan, H., Gu, W., Wang, J., Blumenfeld, Y. J., El-Sayed, Y. Y. & Quake, S. R. Non-invasive prenatal measurement of the fetal genome. Nature 487, 320-324, (2012); Gansen, A., Herrick, A. M., Dimov, I. K., Lee, L. P. & Chiu, D. T. Digital LAMP in a sample self-digitization (SD) chip. Lab Chip 12, 2247-2254, (2012); Thorsen, T., Maerkl, S. J. & Quake, S. R. Microfluidic large-scale integration. Science 298, 580-584, (2002); Ottesen, E. A., Hong, J. W., Quake, S. R. & Leadbetter, J. R. Microfluidic digital PCR enables multigene analysis of individual environmental bacteria. Science 314, 1464-1467, (2006); Fan, H. C., Blumenfeld, Y. J., Chitkara, U., Hudgins, L. & Quake, S. R. Noninvasive diagnosis of fetal aneuploidy by shotgun sequencing DNA from maternal blood. Proc. Natl. Acad. Sci., U.S.A. 105, 16266-16271, (2008); Du, W. B., Li, L., Nichols, K. P. & Ismagilov, R. F. SlipChip. Lab Chip 9, 2286-2292, (2009); Fan, H. C., Blumenfeld, Y. J., El-Sayed, Y. Y., Chueh, J. & Quake, S. R. Microfluidic digital PCR enables rapid prenatal diagnosis of fetal aneuploidy. Am. J. Ob. Gynecol. 200, 543.e541-543.e547, (2009); Liu, W. S., Chen, D. L., Du, W. B., Nichols, K. P. & Ismagilov, R. F. Slip Chip for Immunoassays in Nanoliter Volumes. Anal. Chem. 82, 3276-3282, (2010); Shen, F., Du, W. B., Davydova, E. K., Karymov, M. A., Pandey, J. & Ismagilov, R. F. Nanoliter Multiplex PCR Arrays on a SlipChip. Anal. Chem. 82, 4606-4612, (2010); Heyries, K. A., Tropini, C., VanInsberghe, M., Doolin, C., Petriv, O. I., Singhal, A., Leung, K., Hughesman, C. B. & Hansen, C. L. Megapixel digital PCR. Nat. Methods 8, 649-U664, (2011).

Readouts

Assay results can comprise a readout or detection mechanism chosen from a range of readouts used to detect progress or results of reactions. Examples include but are not limited to electrochemical readouts, optical readouts, including for example fluorescence readouts, colorimetric readouts, chemiluminescence, electrical signals, quenching, probe binding, probe hybridization, metal labeling, contrast agent labeling, absorbance, mass spectrometry, sequencing, lateral flow strips, and the generation of a heterogeneous substance (e.g., precipitation, gas bubble).

A readout mechanism can comprise fluorescence. For example fluorescent dye can be used to label nucleic acids; reactions with more nucleic acid product can yield more fluorescence signal. Fluorescent dyes can include but are not limited to ethidium bromide, berberine, proflavine, daunomycin, doxorubicin, thalidomide, YOYO-1, SYBR Green I, SYBR Green II, oxazole yellow (YO), thiazole orange (TO), PicoGreen (PG), TOTO, TO-PRO, SYTOX, SYTO, other cyanine dyes, and calcein. The fluorescence intensity can be measured at an end-point or in real-time, allowing measurement of the reaction progress. For example, a given level of fluorescence can be set as the threshold for a positive signal from a digital or quasi-digital compartment. Alternatively, a readout mechanism can operate without fluorescence.

A readout mechanism can comprise mass spectrometry. For example, nucleic acids of different sizes (e.g. from restriction digestion or ligation) can be distinguished and/or counted by mass spectrometry. Alternatively, a readout mechanism can operate without mass spectrometry.

A readout mechanism can comprise electrophoresis, including gel electrophoresis. For example, nucleic acids of different sizes (e.g. from restriction digestion or ligation) can be identified or distinguished by electrophoresis. Alternatively, a readout mechanism can operate without electrophoresis.

A readout mechanism can comprise sequencing. Sequencing, or sequence determination techniques, can be performed by methods including but not limited to Sanger sequencing, Illumina (Solexa) sequencing, pyrosequencing, next generation sequencing, Maxam-Gilbert sequencing, chain termination methods, shotgun sequencing, or bridge PCR; next generation sequencing methodologies can comprise massively parallel signature sequencing, polony sequencing, SOLiD sequencing, Ion Torrent semiconductor sequencing, DNA nanoball sequencing, Heliscope single molecule sequencing, single molecule real time (SMRT) sequencing, nanopore DNA sequencing, tunnelling currents DNA sequencing, sequencing by hybridization, sequencing with mass spectrometry, microfluidic Sanger sequencing, microscopy-based techniques, RNA polymerase sequencing or in vitro virus high-throughput sequencing. Sequencing reads can be used to identify reaction products, and the number of sequencing reads generated for a given nucleic acid product can be used to evaluate the reaction. For example, a given number of sequencing reads can be set as the threshold for a positive signal from a digital or quasi-digital compartment. Alternatively, a readout mechanism can operate without sequencing.

Signal can be detected by a variety of techniques, including but not limited to optical techniques, electrical techniques or magnetic techniques. The signal can be optically detectable, for example fluorescent signal, phosphorescent signal, colorimetric signal, absorption signal, or scattering signal.

In some cases, a modulator can act on the read-out or detection mechanism. For example, a modulator can affect the generation of a fluorescent signal, the conducting of a sequencing reaction, the formation of precipitate, the formation of a gas bubble, or other read-out or detection mechanisms. For example, a modulator can ligate a nucleic acid molecule to prepare it for subsequent detection (e.g., sequencing or probe hybridization), or a modulator can digest a nucleic acid molecule to prevent subsequent detection (e.g., sequencing or probe hybridization). In another example, a modulator can be added to an amplification reaction where a fluorescent probe (e.g., molecular beacon, TaqMan, or Fluorescence Resonance Energy Transfer (FRET) probe) is employed to generate a specific fluorescent signal. Fluorescent probes can be designed to hybridize within the amplification product. In some cases, the addition of a modulator (e.g., an oligonucleotide) that hybridizes on the same target as the probe, or a target similar to the target on the probe, can prevent the interaction (e.g., by acting as a block) between the probe and the amplification product and thus can affect the readout. Specificity of modulators and probes can be different. In some cases, the modulator can bond to a specific region of a nucleic acid, such as for example to a SNP, and the modulator can confer to the probe the ability to discriminate between sequences. In some cases, probes can be sensitive to the presence of a SNP without targeting the specific area where the SNP is located.

In some examples, the methods described here can be used to select genomic regions of interest and enrich regions of interest (e.g., regions of eukaryotic genomes) before sequencing. In some cases, modulators can be used to inhibit the capture or pre-amplification of a predominant population of nucleic acids, enabling enrichment of the target of interest. In some cases, a modulator may be used for sequencing purposes. For example, a modulator can comprise two regions of specificity—one side of the modulator can recognize a specific conserved region within a targeted genome and the other side of the modulator can be designed to link to a particular element (e.g., an immobilized primer present in the sequencing platform). In some cases, as a result of the modulator interacting simultaneously with both the molecule of interest and the platform, a single nucleic acid molecule can be isolated and independently analyzed from the pool of nucleic acids.

Platforms

The assays, reactions, and techniques described herein can be performed on any suitable platform, including but not limited to tubes, capillary tubes, droplets, microfluidic devices (e.g., SlipChip devices), wells, well plates, microplates, microfluidic wells, microfluidic droplets, emulsions, solid supports (e.g., beads or microarrays), microchips, or gels (e.g., 2D gels, 3D gels) and reactions inside gels including "polonies" as in polony PCR on surfaces and in gels.

Platforms can comprise fluid handling mechanisms enabling loading, unloading, mixing, and other handling of sample volumes, reagent volumes, and other fluids. For example, a microfluidic device can be used comprising channels for loading fluids into wells or droplets, for mixing contents of wells or droplets, or for off-loading of contents of wells or droplets.

Some platforms are useful for conducting assays in a digital or quasi-digital format, as described herein. For example, wells, well plates, microwells, microfluidic droplets, emulsions, beads, and microarrays can provide a useful platform for conducting a digital or quasi-digital assay. In such an assay, the compartments can comprise individual wells, droplets, beads, or microarray spots.

Platforms can be compatible with one or more readout or detection mechanisms. For example, a platform can be transparent or translucent in part or in total, allowing fluorescent measurement, detection of precipitate or gas bubble, or other visual observation. A platform can comprise visual detectors, such as CCDs, CMOS sensors, cameras, photon detectors, and other sensors. In another example, a platform can comprise electrical sensors, such as electrodes positioned within microwells. Platforms can be compatible with off-loading of samples for analysis. For example, a platform can permit unloading of droplets or contents of wells for mass spectrometry, sequencing, or electrophoresis.

Applications

An assay can be conducted in less than or equal to about 600 minutes, 540 minutes, 480 minutes, 420 minutes, 360 minutes, 300 minutes, 240 minutes, 180 minutes, 120 minutes, 110 minutes, 100 minutes, 90 minutes, 80 minutes, 70 minutes, 60 minutes, 50 minutes, 40 minutes, 30 minutes, 20 minutes, 15 minutes, 10 minutes, 9 minutes, 8 minutes, 7 minutes, 6 minutes, 5 minutes, 4 minutes, 3 minutes, 2 minutes, or 1 minute. An assay can have an accuracy of at least about 50%, 60%, 70%, 80%, 90%, 95%, 96%, 97%, 98%, 99%, 99.9%, or 99.99%. The rates of false positives can be below 10%, below 1%, below 0.1%, below 0.01%, below 0.001%, or below 0.0001%. The rates of false negatives can be below 10%, below 1%, below 0.1%, below 0.01%, below 0.001%, or below 0.0001%.

Assays can be used for single-nucleotide polymorphism (SNP) detection or discovery. DNA sequence variations can occur when a single nucleotide in a genome or other shared sequence differs between members of a biological species, or between paired chromosomes in a human. When a specific restriction enzyme pattern or genetic fingerprint has been established (e.g., as described herein), any change to it (e.g., new negative reactions) can indicate a modification in the sequence of the produced amplicons, from a SNP to a chromosome level change.

Assays can be used for detecting copy number variations (CNVs). CNVs are a form of structural variation, alterations of the DNA of a genome that changes the number of copies of one or more sections of the DNA. CNVs can correspond to relatively large regions of the genome that have been deleted or duplicated on certain chromosomes. Like other types of genetic variation, some CNVs have been associated with susceptibility or resistance to disease. Gene copy number can be elevated in cancer cells. The methodology described herein also allows identifying genetic changes at chromosome level.

An assay can be used for quantitative detection of nucleic acids, such as Hepatitis C RNA. For example, a method can be used comprising the steps of taking a sample from the patient, accessing RNA in the sample or extracting RNA from the sample, using at least one RT-LAMP primer set as set out in Table 10 to reverse transcribe and amplify the RNA in a qualitative and/or in a quantitative format, and testing for amplification to confirm presence of nucleic acids including but not limited to Hepatitis C RNA.

Figure 5A:
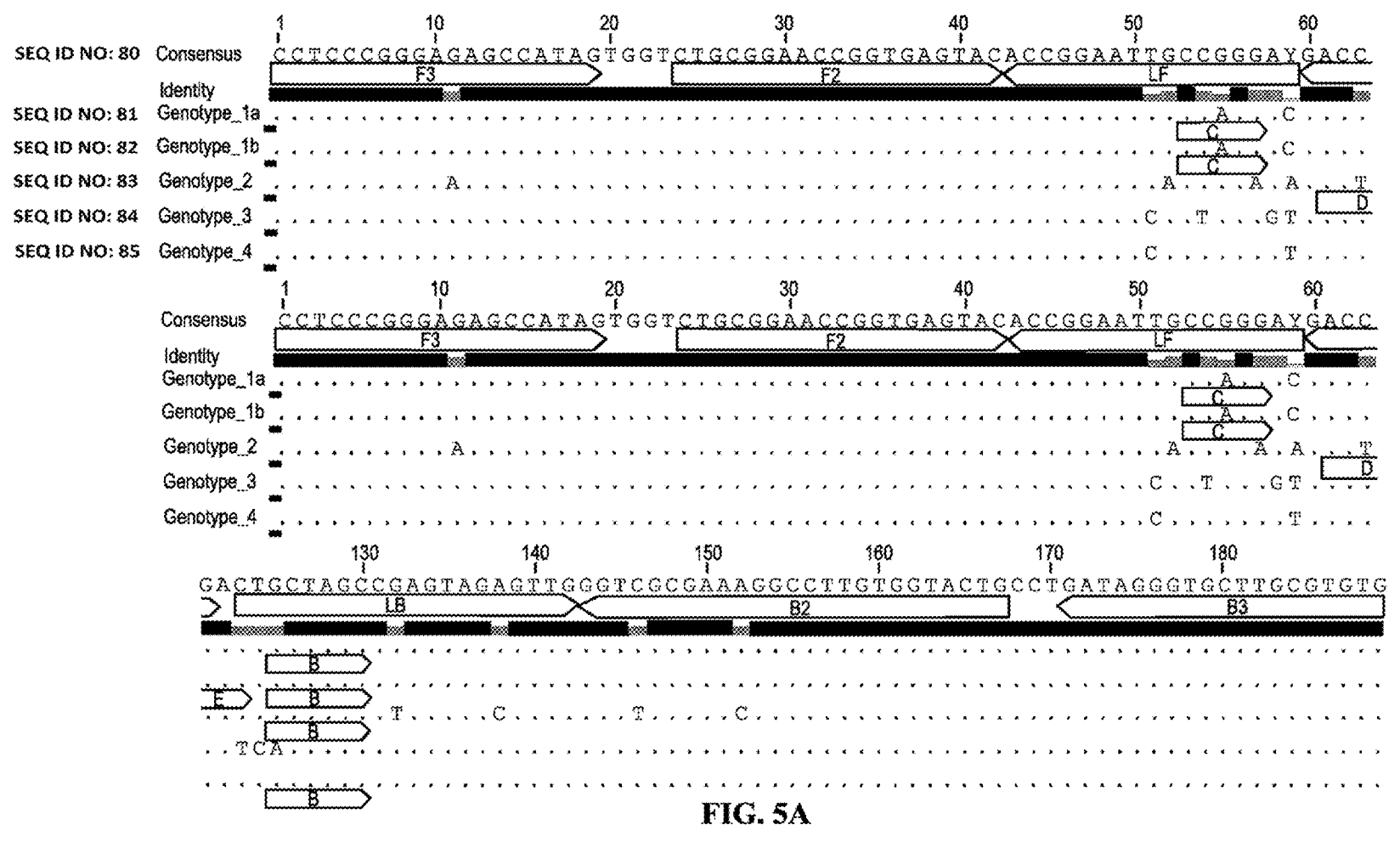
Figure 5B:
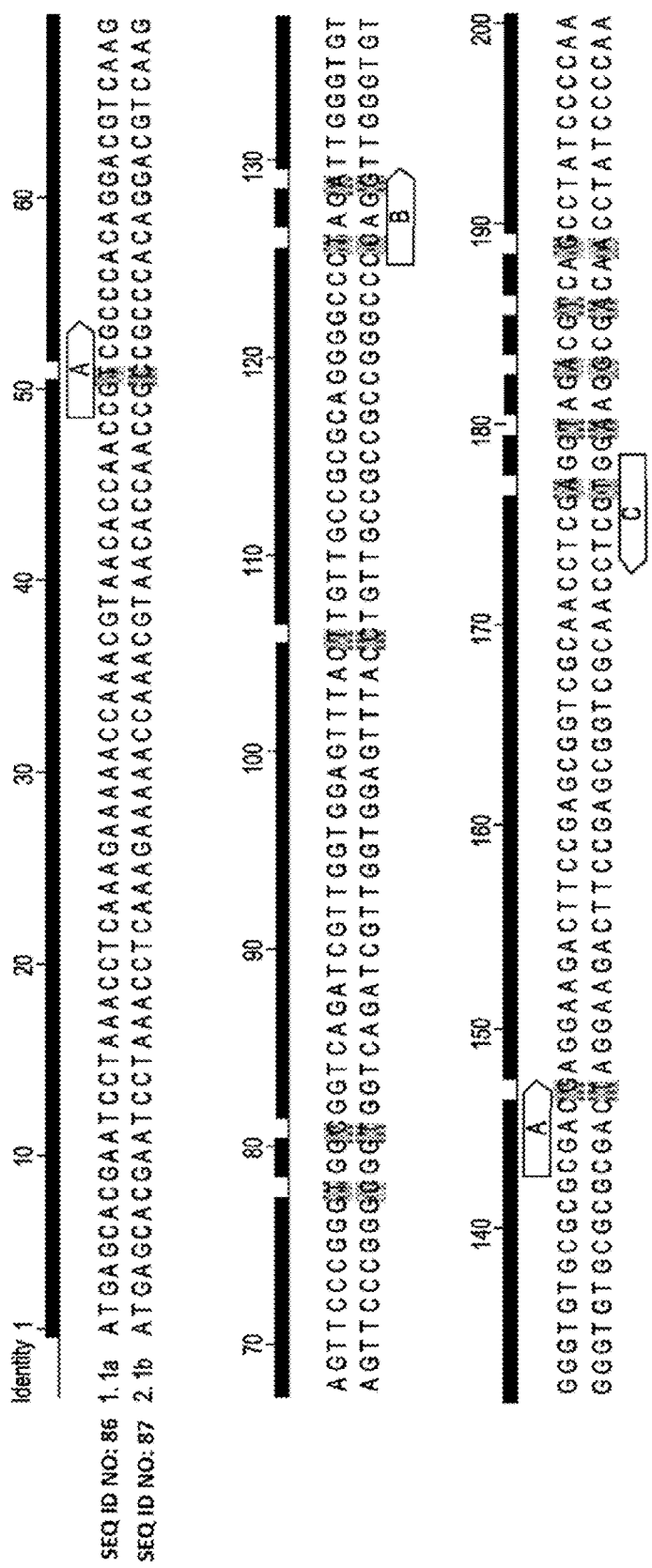
FIG. 5B shows an exemplary alignment of RNA sequence and potential digestion site for 1a 1b subtyping in core region of HCV.

Assays can be used for genotyping, i.e. determining differences in the genetic make-up (genotype) of an organism or group of organisms by examining the DNA or RNA sequence and comparing it to a reference sequence. This can be used to define biological populations by use of molecular tools. For example, Example 1 shows three different restriction enzymes (BsrBI, BstNI and NheI) used to classify different hepatitis C virus (HCV) samples into the genotype level, from genotype 1 to genotype 4. Subtyping of HCV can also be achieved using this methodology. HCV subtype 1a and 1b are reported to have different response to therapy (see, e.g., "A M Pellicelli, M Romano, T Stroffolini, E Mazzoni, F Mecenate, R Monarca, A Picardi, M E Bonaventura, C Mastropietro, P Vignally, A Andreoli, M Marignani, C D'Ambrosio, L Miglioresi, L Nosotti, O Mitidieri, U V Gentilucci, C Puoti, G Barbaro, A Barlattani, C Furlan, G Barbarini, BMC Gastroenterol. 2012 Nov. 16; 12:162"), and for the CLEO Group, HCV Genotype 1a shows a better virological response to antiviral therapy than HCV Genotype 1b. As a result, differentiating Genotype 1a from Genotype 1b can be clinically important. Using the same priming region described in Example 1, subtyping can be achieved with restriction enzyme BcoDI, as shown in FIG. 5A. Other restriction enzyme candidates are available for subtyping to target other regions of the HCV genome, such as NS5b or CORE. For example, Hpy99I, BstNI and BssSI, among others, are good candidates for 1a/1b subtyping in the HCV CORE region as shown in FIG. 5B.

Assays can be used for detecting epigenetic marks or modifications (e.g., methylation, glycosylation, hydroxymethylation): Epigenetic modifications can comprise functionally relevant modifications to the genome that do not involve a change in the nucleotide sequence. Methylation of DNA is a common epigenetic signaling tool and is an important component in numerous cellular processes (e.g., embryonic development, genomic imprinting, X-chromosome inactivation). Errors in methylation are linked to a variety of devastating consequences, including several human diseases. Furthermore, adenine or cytosine methylation is part of the restriction modification system of many bacteria, in which specific DNA sequences are methylated periodically. Foreign DNAs, which are not methylated in this manner, that are introduced into the cell are degraded by sequence-specific restriction enzymes and cleaved (while bacterial genomic DNA is not recognized by these restriction enzymes). The methylation of native DNA can act as a sort of primitive immune system, allowing the bacteria to protect themselves from infection by bacteriophage. As an example of this application, when restriction enzyme recognition sites are methylated, DNA cleavage can be blocked, depending on the restriction enzyme; the methodologies presented herein can detect and identify such methylation. In another example, some restriction enzymes depend on methylation and hydroxymethylation for cleavage to occur (e.g., EpiMark®); methylation-dependent restriction enzyme activity (both positive and negative) can be used to map epigenetic modifications and study DNA methylations. Epigenetic analysis can be accomplished using the methodologies described herein.

Assays can be used for identification of mutations, such as drug resistance mutations (DRM). Drug resistance can be achieved by multiple mechanisms, including horizontal acquisition of resistance genes (carried by plasmids or transposons), by recombination of foreign DNA into the chromosome, or by mutations in different chromosomal loci. The methodologies described herein can be used for the identification of a characteristic restriction enzyme pattern or fingerprint, or the activity of specific restriction enzymes, associated with mutations that confer drug resistance. For example, an assay can be used for diagnosis of Methicillin-resistant *Staphylococcus aureus* (MRSA): MRSA is a pathogen responsible for a wide spectrum of healthcare-associated and community-acquired infections. Infections with MRSA strains that are resistant to different types of antibiotics are a serious therapeutic problem, because only a limited spectrum of antibiotics can be used, and treatment can require prolonged hospitalization and result in economic losses. In order to limit the overspread of pathogens, the development of diagnostic tools enabling rapid identification of carriers and infected patients, also enabling livestock and food supply screening and testing, may be accomplished using the methodologies described herein.

Assays can be used to screen for transgene integration. A transgenic organism has in its cells a foreign gene that has been inserted by laboratory techniques or inherited from a transgenic parent organism. Transgenic organisms can be produced by introducing cloned genes, composed of DNA from microbes, animals, or plants, into plant and animal cells. Transgenic technology affords methods that allow the transfer of genes between different species. Identification of a genetically modified organism (e.g., food or laboratory animals) may be accomplished using the methodologies described herein.

Assays can be used for detection of restriction enzyme activity, identifying new restriction enzymes, or evaluating restriction enzyme activity. As explained in "Julie K. A. Kasarjian, Yoshiaki Kodama, Masatake Iida, Katsura Matsuda, and Junichi Ryu, Four new type I restriction enzymes identified in *Escherichia coli* clinical isolates, Nucleic Acids Res. 2005; 33(13): e114," the recognition sequences for type II enzymes are relatively easy to identify using crude extracts to digest fixed DNA sequences to produce distinct DNA bands; sequences can then be predicted using a computer program, such as REBpredictor (New England Biolabs). However, no simple method has been identified for finding type I recognition sequences, in part because the enzymes produce DNA fragments with random sequences (TA Bickle and DH Kruger, Biology of DNA Restriction, Microbiol. Rev. 1993; 57:434-450). Identification of new restriction enzymes or analysis of restriction enzyme target sequences can be accomplished using the methodologies described herein. For example, amplification reactions can be conducted on different template nucleic acid sequences in the presence of a restriction enzyme modulator, and the effect (e.g., reduced efficiency or rate) of the modulator can be observed and correlated to particular sequences.

Assays can be used to subtype or characterize strains of viruses. For example, there are three types of influenza viruses: A, B and C. Human influenza A and B viruses cause seasonal epidemics. Influenza A viruses are hosted by numerous avian and mammalian (humans, pigs, horses, dogs, marine mammals and others) species, with a viral genome consisting of eight RNA segments that are frequently exchanged between different viruses via a process known as genetic reassortment. Influenza type A viruses are categorized into subtypes based on the type of two proteins on the surface of the viral envelope, H (hemagglutinin, a protein that causes red blood cells to agglutinate) and N (neuraminidase, an enzyme that cleaves the glycosidic bonds of the monosaccharide, neuraminic acid). Different influenza viruses encode for different hemagglutinin and neuraminidase proteins. For example, the H5N1 virus designates an influenza A subtype that has a type 5 hemagglutinin (H) protein and a type 1 neuraminidase (N) protein. Influenza A subtypes found in humans include H1N1, H2N2, H3N2, H5N1, H7N7, H1N2, H9N2, H7N2, H7N3, H10N7 and H7N9. The methodologies described herein can be used for rapid and accurate identification and screening of targets (e.g., influenza virus). An assay can be conducted in less than or equal to about 600 minutes, 540 minutes, 480 minutes, 420 minutes, 360 minutes, 300 minutes, 240 minutes, 180 minutes, 120 minutes, 110 minutes, 100 minutes, 90 minutes, 80 minutes, 70 minutes, 60 minutes, 50 minutes, 40 minutes, 30 minutes, 20 minutes, 15 minutes, 10 minutes, 9 minutes, 8 minutes, 7 minutes, 6 minutes, 5 minutes, 4 minutes, 3 minutes, 2 minutes, or 1 minute. An assay can have an accuracy of at least about 50%, 60%, 70%, 80%, 90%, 95%, 96%, 97%, 98%, 99%, 99.9%, or 99.99%. The rates of false positives can be below 10%, below 1%, below 0.1%, below 0.01%, below 0.001%, or below 0.0001%. The rates of false negatives can be below 10%, below 1%, below 0.1%, below 0.01%, below 0.001%, or below 0.0001%. Methodologies can have applications in pandemic influenza risk management. The methodologies described herein can also be used to detect the emergence of new virus strains, such as new strains of influenza. Current systems for typing and subtyping influenza viruses include virus replication in egg or cell culture followed by either immunofluorescence assays with strain-specific monoclonal antibodies or hemagglutination inhibition assays using a panel of reference antisera, which can be tedious and requires several days or even weeks (see M. L. Landry, Diagnostic tests for influenza infection, Curr Opin Pediatr, 2011, 23: 91-97). Assays described herein can be used for routine point-of-care tests, including subtyping capability useful for surveillance of diseases.

Assays can comprise amplification of the haemagglutinin (HA) and/or neuraminidase (NA) genes for subtyping, which genes comprise highly variable genomic regions that hinder the standardization of molecular methods. In some cases, HA and NA genes of influenza can be targeted while circumventing the need for repeated re-design of primers and probes. Influenza viruses can be identified detected and monitored by using the methodologies described herein by targeting sequences surrounding SNPs that are located in the matrix (M) gene segment, a highly conserved gene in the influenza genome. The M gene has enough genetic diversity for influenza subtyping purposes and sufficient genetic stability to for detection and typing. To reduce the number of sequences being targeted in this approach, one can, for example, establish phylogenetic groups based on the M segment that correlate with a group of subtypes, reducing the number of variables to target and potentially simplifying the analysis of HA and NA segments in the platform. Sequences for the M gene segment of influenza A and B can be compiled using the Influenza Virus Resource database at the National Center for Biotechnology, the Influenza Research Database, and The Influenza Sequence Database at Los Alamos National Laboratory. If needed, sequences for HA and NA gene segments for influenza A can, for example, be also compiled from the same source. This approach can be used to find genetic markers that are unique to a particular subtype or group of subtypes of influenza based on host species. These databases can in some examples be separated by subtype and host. Phylogenetic reconstruction can be conducted according to the following bioinformatics pipeline. (i) Alignment: In the alignment step of phylogenetic reconstruction, the homology of the whole sequences can be refined to identify homologous sites by, for example, placing gaps at sites where insertions or deletions have occurred since the last common ancestor. To perform this step the Prank algorithm as implemented in SATé II (Simultaneous Alignment and Tree Estimation) can be used (see K. Liu, T. J. Warnow, M. T. Holder, S. M. Nelesen, J. Yu, A. P. Stamatakis and C. R. Linder, SATe-II: very fast and accurate simultaneous estimation of multiple sequence alignments and phylogenetic trees, Syst Biol, 2012, 61: 90-106). The resulting alignment can, in some cases, be manually curated to eliminate regions that could have been misaligned (due to, e.g., high variability). (ii) Model selection: Some phylogenetic methods (e.g., maximum likelihood and Bayesian analysis) may benefit from specification of an evolutionary model. In some cases the model of evolution can be selected using the Akaike information criterion and/or Bayesian cross-validation using, for example, jModelTest and PhyloBayes, respectively (see D. Posada, jModelTest: phylogenetic model averaging, Mol Biol Evol, 2008, 25: 1253-1256; and N. Lartillot, T. Lepage and S. Blanquart, PhyloBayes 3: A Bayesian software package for phylogenetic reconstruction and molecular dating, Bioinformatics, 2009, 25, 2286: 2288). (iii) Phylogeny Reconstruction: In some cases phylogenetic reconstruction can be performed under maximum likelihood and Bayesian frameworks. Maximum likelihood can be carried out using RAxML and reliability of nodes can be evaluated using bootstrapping (see A. Stamatakis, RAxML version 8: a tool for phylogenetic analysis and post-analysis of large phylogenies, Bioinformatics, 2014, doi: 10.1093/bioinformatics/btu033). In some examples Bayesian analysis can be performed using PhyloBayes. Potential sources of systematic error can be evaluated using Bayesian posterior predictive analysis as implemented in PhyloBayes in order to assess the reliability of the resulting topology, in some examples (See N. Lartillot, T. Lepage and S. Blanquart, PhyloBayes 3: A Bayesian software package for phylogenetic reconstruction and molecular dating, Bioinformatics, 2009, 25, 2286: 2288). (iv) Genetic marker prediction: Single nucleotide polymorphism detection can involve looking across multiple sequence alignments and identifying base discrepancies. The higher the sequence coverage and quality score at a given site, the more confident the SNP prediction. In some cases, existing tools (e.g., Phrap or PineSAP) can be used to make confident identifications when visual confirmation is not an option (See M. Machado, W. C. Magalhaes, A. Sene, B. Araujo, A. C. Faria-Campos, S. J. Chanock, L. Scott, G. Oliveira, E. Tarazona-Santos and M. R. Rodrigues, Phred-Phrap package to analyses tools: a pipeline to facilitate population genetics re-sequencing studies, Investig Genet, 2011, 2, 3 and J. L. Wegrzyn, J. M. Lee, J. Liechty, and D. B. Neale, PineSAP-sequence alignment and identification pipeline, Bioinformatics, 2009, 25, 2609-2610). Strategies for ensuring low rates of false positives in subtyping can also be used in some examples; a test or assay can report not only the subtype but also provide some information on, for example, the confidence of the subtype designation. These approaches can be used to create tests with low rates of false positives, which would be advantageous when millions of people are screened. The rates of false positives can be below 10%, below 1%, below 0.1%, below 0.01%, below 0.001%, or below 0.0001%.

While a number of details are provided herein for relating to analysis of influenza, analysis of other viruses (including detection, typing, subtyping, SNP detection, and other analysis) can be performed analogously. Analysis of Hepatitis viruses, including HCV, HBV, HAV, HIV, HPV, and other viruses of relevance to human health, agriculture, agricultural biotechnology, and other practical applications, can be performed. Analysis and detection of viral, archaeal, bacterial, fungal, mammalian, human, and other nucleic acids can be performed. Analysis and detection includes comparative analysis and detection, where a target nucleic acid is compared with another nucleic acid.

The methodologies described herein can be used to detect other activities in conjunction with detection and or amplification such as reactions that make or break chemical bonds, reactions that lead to formation of complexes between molecules, or reactions that lead to formation of complexed between molecules and objects such as beads and surfaces. The methodologies can be used to detect activation of detection or amplification. For example, a protease can be used to degrade at least one peptide bond in a complex between a target nucleic acid and a molecule containing such a peptide bond (e.g., proteins, peptides, and their derivatives). This degradation can cause dissociation of the complex between the target nucleic acid and the molecule containing such a peptide bond, enhancing the amplification or detection of the target nucleic acid. Similarly, a glycosidase can be used to degrade a glycosidic bond, leading to the release of small sugars. If the release of the small sugar or the degradation of the glycosidic bond leads to the formation or degradation of some complex between molecules, it can change the rate of an amplification reaction or allow or prevent an amplification reaction. Glycoside hydrolase can also be used as synthetic catalysts to form glycosidic bonds through either reverse hydrolysis. Glycosyltransferases, on the other hand, can establish natural glycosidic linkages, including the biosynthesis of disaccharides, oligosaccharides and polysaccharides. Glycosyltransferases can catalyse the transfer of monosaccharide moieties from activated nucleotide sugar (also known as the "glycosyl donor") to a glycosyl acceptor molecule, such as an alcohol. The result of glycosyl transfer can be a carbohydrate, glycoside, oligosaccharide, or a polysaccharide. Similarly, kinase enzymes can be used to transfer phosphate groups from high-energy donor molecules, such as ATP to specific substrates, a process referred to as phosphorylation, while phosphorylases can be used to conduct phosphorolysis, the breaking of a bond using an inorganic phosphate group. Aptamers can be used to bind to specific proteins or nucleic acid targets.

Assays can be used to identify drug resistance mutations (DRMs). Drug resistance can be achieved by multiple mechanisms, including but not limited to horizontal acquisition of resistance genes (carried by plasmids or transposons), by recombination of foreign DNA into the chromosome, or by mutations in different chromosomal loci. The identification of a characteristic restriction enzyme pattern or the activity of specific restriction enzymes associated with mutations that confer drug resistance can, in some cases, be accomplished using the methodologies described herein. Drug resistance can be determined using the methodologies described herein in subjects including but not limited to viruses, bacteria, fungi, plants, prokaryotes, and eukaryotes. These mutations can also be determined in, e.g., cancer cells and cell-free DNA. For example, this can be applied to identify drug resistance mutations in HCV (see, e.g., "Clinically Relevant HCV Drug Resistance Mutations Figures and Tables, from HCV Phenotype Working Group, HCV Drug Development Adivosry Group, Ann Forum Collab HIV Res. Volume 14 (2): 2012; 1-10" or "Forum for Collaborative HIV Research, University of California Berkeley School of Public Health"), HIV (see, e.g., "Victoria A. Johnson, MD, Vincent Calvez, MD, PhD, Huldrych F. Günthard, MD, Roger Paredes, MD, PhD, Deenan Pillay, MD, PhD, Robert W. Shafer, MD, Annemarie M. Wensing, MD, PhD, and Douglas D. Richman, MD, Update of the Drug Resistance Mutations in HIV-1: March 2013, Topics in Antiviral Medicine, 2013; 21:6-14"), and influenza A virus (see, e.g., "Goran Orozovic, Kanita Orozovic, Johan Lennerstrand, Bjorn Olsen, Detection of Resistance Mutations to Antivirals Oseltamivir and Zanamivir in Avian Influenza A Viruses Isolated from Wild Birds. PLoS ONE 6(1): e16028. doi: 10.1371/journal.pone.0016028").

Assays can be used for genetic testing, including fetal genetic testing. For example, assays can be used for non-invasive pre-natal Trisomy 21 (Down syndrome) diagnostics. Assays can be used with a screening test which indicates the likelihood of trisomy. Assays can be used with or as a screening test for a subsequent diagnostic test which is a more accurate test provided only to people with a high score in the screening test. A screening test can comprise an ultrasound test. A screening test can comprise a maternal serum screening blood test measuring the level of human chorionic gonadotropin (β-hCG), pregnancy associated plasma protein-A (PAPP-A), alpha fetoprotein (AFP), or other protein biomarkers. A screening test can provide a probability instead of a finite answer. If the screening test gives a high score, an invasive diagnostic test, such as chorionic villus sampling (CVS) or amniocentesis, can be used. Cell-free fetal DNA (cffDNA) or RNA (cffRNA) exist in maternal plasma that can be isolated and subjected to molecular analysis (see, e.g., "Y M Dennis Lo, Noemi Corbetta, Paul F Chamberlain, Vik Rai, Ian L Sargent, Christopher W G Redman, James S Wainscoat, Presence of fetal DNA in maternal plasma and serum, Lancet 1997, 350, 485-487"). The cff DNA and cff RNA can be used in assays for non-invasive biomarker discovery and detection. For cff DNA, a biological and therefore technical constraint is that it only takes up 3-6% of the total amount of cell-free DNA. The proportion increases at a later stage of gestation, but is still a minor fraction of the total amount of cell-free DNA in plasma. Assays can directly target fetal-specific DNA or RNA. The placenta is an organ that can represent genetic information from the fetus. Placental-specific RNA, when expressed and released in a tissue-specific manner, qualifies as a fetal-specific RNA because it exists only in pregnant individuals and does not exist before or after pregnancy. Assays can comprise detection of trisomy 21 using placental specific RNA by direct dosage-related difference in the expression of chromosome 21 encoded genes (see, e.g., "Chi-Ming Li, Meirong Guol, Martha Salas, Nicole Schupf, Wayne Silverman, Warren B Zigman, Sameera Husain, Dorothy Warburton, Harshwardhan Thaker, and Benjamin Tycko, "Cell type-specific over-expression of chromosome 21 genes in fibroblasts and fetal hearts with trisomy 21" BMC Medical Genetics 2006, 7: 24"). Assays can comprise detection of trisomy 21 using placental specific RNA by relative RNA allelic ratio assessment using SNP analysis (see, e.g., "Y M Dennis Lo., Nancy B Y Tsui, Rossa W K Chiu, Tze K Lau, Tse N Leung, Macy M S Heung, Egeliki Gerovassili, Yongjie Jin, Kypros H Nicolaides, Charles R Cantor, and Chunming Ding, Plasma placental RNA allelic ratio permits noninvasive prenatal chromosomal aneuploidy detection, Nat. Med. 2007, 13, 218"). Relative RNA allelic ratio assessment using SNP analysis can quantify the relative abundance of each allele in expressed placental specific RNA when there is a heterozygous loci on chromosome 21 genes, with the assumption that the ratio of the two alleles for mothers carrying a trisomy 21 baby should be 2:1, and for a normal baby it should be 1:1. Since only a relative ratio is required, the number of wells or other partitions can be small if digital PCR is used in such an assay.

Figures 16A, 16B:
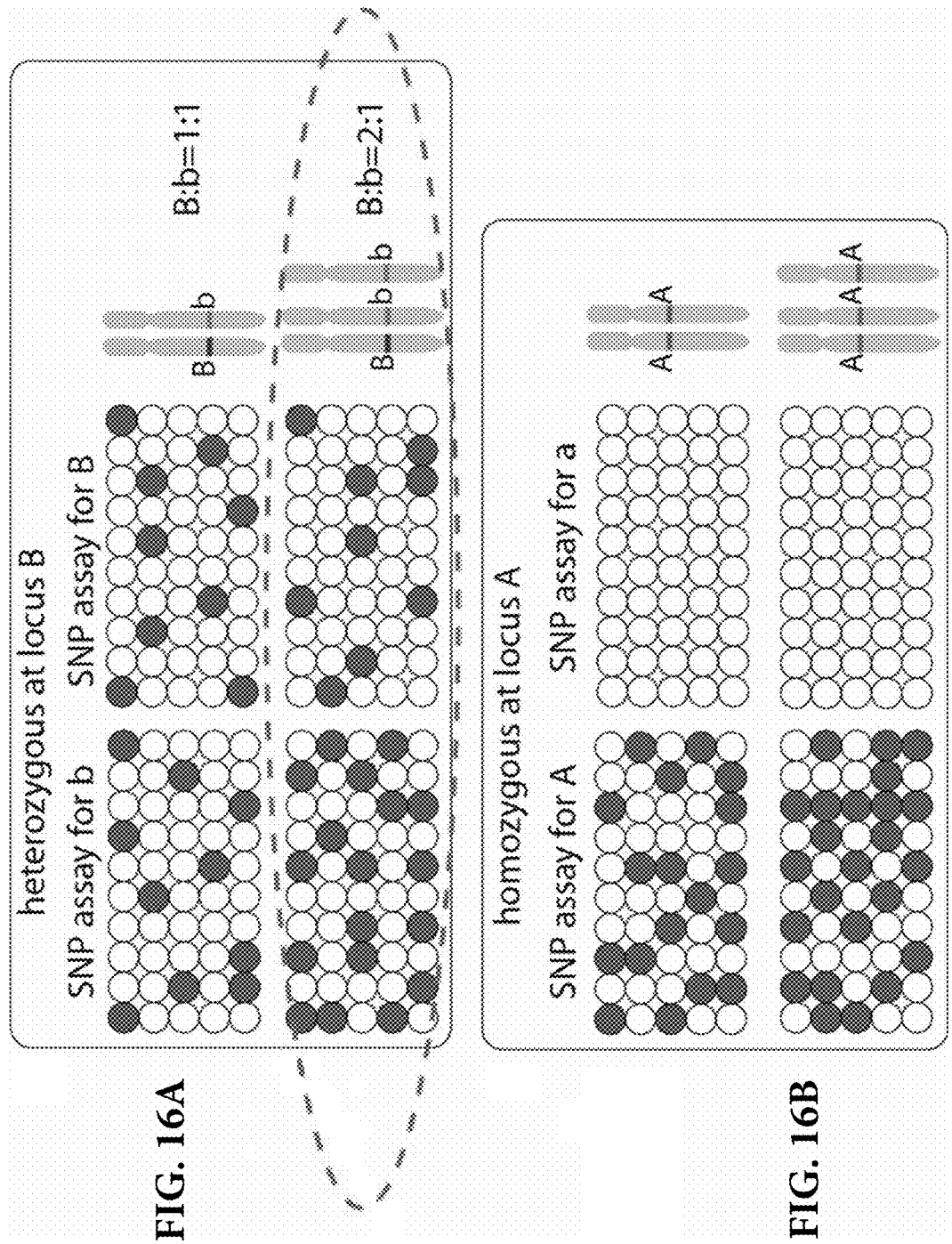
FIG. 16A shows an exemplary design and expected results for an assay for trisomy.
FIG. 16B shows an exemplary design and expected results for an assay for trisomy.

Described herein is an exemplary a rapid assay not requiring CVS or amniocentesis that can be used as a screening test or a diagnostic test with high sensitivity and specificity based on, in one example, RNA SNP quantification on chromosome 21. In some cases, this platform can have the capacity for collecting sample and purifying RNA out of the plasma sample, multiplexed SNP ratio quantification, and a relatively simple readout module, including but not limited to one that is cell-phone enabled. The results can be interpretable by, for example, the user or the physician, and in some cases can be offered together with consultation service at the clinic, to help parents make decisions and prepare. Assay coverage can be at least about 50%, 60%, 70%, 80%, 90%, 95%, 96%, 97%, 98%, 99%, 99.9%, 99.99%, or 100%. An assay can be used in combination with another screening test and can decrease the number of false-positives in the screening test. An assay can provide access to such tests to people who do not currently have access. The development of such a platform can fill the gaps between the large demand for trisomy 21 detection and limited access to diagnostics. In one example of this platform, a sample (such as, for example, human blood) can be collected and loaded onto the integrated device. In some cases, the sample can flow to merge with different reagents to complete the RNA extraction step driven by, for example, pressure. In some cases, the RNA can then be mixed with isothermal amplification reagents containing, for example, different inhibitors specific to different alleles. In some cases, after rapid sequence specific amplification, the digital counts for different reactions can be recorded (such as, for example, by a cell phone, which can have a built-in analysis application). In some cases, the assay can comprise a SNP assay for multiple loci, increasing the population coverage of the entire assay. In some cases, proper control and potentially other trisomy detection assays can be included as well. In some cases, for heterozygous loci, the ratio between the two alleles should be 1:1 for euploidy, while that for aneuploidy should be about 2:1. In some cases, for homozygous loci, only one allele will be detected. FIG. 16 shows a schematic of an exemplary prenatal diagnostic test. In FIG. 16A, results are shown for a sample, heterozygous at locus B, negative (upper) and positive (lower) for trisomy. Both show a similar number of positive signals for the 'B' SNP assay, and the sample positive for trisomy shows more positive signals for the 'b' SNP assay. In FIG. 16B, results are shown for a sample, homozygous at locus A, negative (upper) and positive (lower) for trisomy. Both show no positive signals for the 'a' SNP assay, and the sample positive for trisomy shows more positive signals for the 'A' SNP assay. Genetic testing (prenatal or postnatal) can be used to screen for other aneuploidy conditions including but not limited to Edwards syndrome (Trisomy 18) and Patau syndrome (Trisomy 13). Genetic testing can be used to screen for other genetic conditions including but not limited to phenylketonuria and congenital hypothyroidism. Genetic testing can also be used to study or predict drug metabolism (e.g., SNPs and other mutations in the liver P450 cytochrome system of enzymes including CYP2C9, CYP2C19, CYP3A4, and CYP1A2).

Assays can be used for epigenetic testing for diseases and other conditions, including but not limited to Angelman syndrome, Prader-Willi syndrome, Beckwith-Wiedemann syndrome, aberrant DNA methylation associated with cancer (hypermethylation, e.g. at CpG islands in the promoter region or hypomethylation, e.g. global hypomethylation), epigenetic changes (e.g., CpG island methylation) associated with reduced expression of DNA repair genes (e.g., BRCA1, WRN, FANCF, RAD51C, MGMT, MLH1, MSH2, ERCC1, Xpf, NEIL1, FANCB, MSH4, ATM), and variant histones.

Nucleic acid amplification based on universal set of primers targeting common sequences among bacteria or among fungi can be used, for example, to evaluate microbial colonization. Common sequences can include 16S ribosomal RNA or 23S ribosomal RNA in bacteria and 18S ribosomal RNA or 28S ribosomal rRNA genes in fungi. Addition of sequence-specific modulators into these universal PCR systems can be used for bacterial or fungal typing (ribotyping). Ribotyping mediated by modulators can be used, for example, for environmental testing (water, soil, waste, fuel and air) with bacteria including but not limited to *Escherichia coli, Bacillus subtilis, Clostridum perfringens, Clostridium difficile, Enterobacter aerogenes, Enterococcus faecalis, Legionella pneumophila, Legionella bozemanii, Listeria monocytogenes, Pseudomonas aeruginosa, Salmonella typhimurium, Staphylococcus aureus*, and others. Assays can be used for detection of multidrug-resistant organisms (such as *Staphylococcus aureus, Klebsiella pneumoniae, Acinetobacter* spp., *Enterococcus* spp. and *Enterobacter* spp). Assays can be used for detection or identification of sulfate reducing organisms or other organisms which can lead to pipeline corrosion. A sample can be taken from a pipeline, an gut of an organism, or another source.

Assays can be used to identify or characterize mobile genetic elements (e.g., transposons and bacteriophages) or foreign genes inserted by laboratory techniques (e.g., genes inserted into genetically modified organisms). For example, when an amplification reaction targeting a sequence surrounding an inserted gene, the reaction can be inhibited or promoted in the presence of a modulator that interacts with the foreign gene. If the foreign gene is not present, the modulator does not significantly act and the amplification reaction can proceed without substantial change to the rate or efficiency of amplification. Approaches described herein can be used for agricultural biotechnology, to detect genes transfected into plants, animals and microorganisms. In another example, virulence factors of pathogenic bacteria encoded by pathogenicity islands (PAI) can be assessed. PAI carry genes encoding one or more virulent factors, including but not limited to, adhesins, toxins, invasins, protein secretion systems, iron uptake systems, and others. PAI comprise genomic regions that are present on the genomes of pathogenic strains but absent or only rarely present in those non-pathogenic variants of the same related species. An amplification reaction can be triggered, for example, by the presence a specific PAI. For example, an amplification reaction can be blocked by a modulator, and in the presence of a specific sequence contained in the PAI the modulator can be removed and the amplification reaction can be initialized. The presence of transferred genes (or transferred geneomictic islands) can also be used in combination with a modulator, for example with pathogenic bacteria such as *Escherichia* spp., *Shigella* spp., *Yersinia* spp., *Vibrio* spp., *Clostridium* spp., *Haemophilus* spp., *Helicobacter* spp., *Neisseria* spp., *Pseudomonas* spp., *Mycobacterium* spp. and others.

Assays can be used identification of single point mutations, for example for viral genotyping. Genotyped viruses can include but are not limited to hepatitis C virus, hepatitis B virus, human immunodeficiency virus, human cytomegalovirus, norovirus and enterovirus. Assays can be used for viral typing and subtyping. Typed or subtyped viruses can include but are not limited to human papilloma virus, avian influenza virus, human influenza virus, swine influenza virus, herpes simplex virus, foot and mouth disease virus, dengue virus and rotavirus. Assays can be used for bacterial typing. Typed bacteria can include but are not limited to *Francisella* spp., *Escherichia* spp., *Salmonella* spp., *Mycobacterium* spp., *Bacillus* spp., *Staphylococcus* spp., *Streptococcus* spp., *Acinetobacter* spp., *Helicobacter* spp., *Bordetella* spp., *Bordetella* spp. and *Vibrio* spp. Assays can be used to assess for the presence or absence of drug resistance mutations, in subjects including but not limited to human immunodeficiency virus, hepatitis C virus, and cancer drug resistance.

Control Systems

Figure 6:
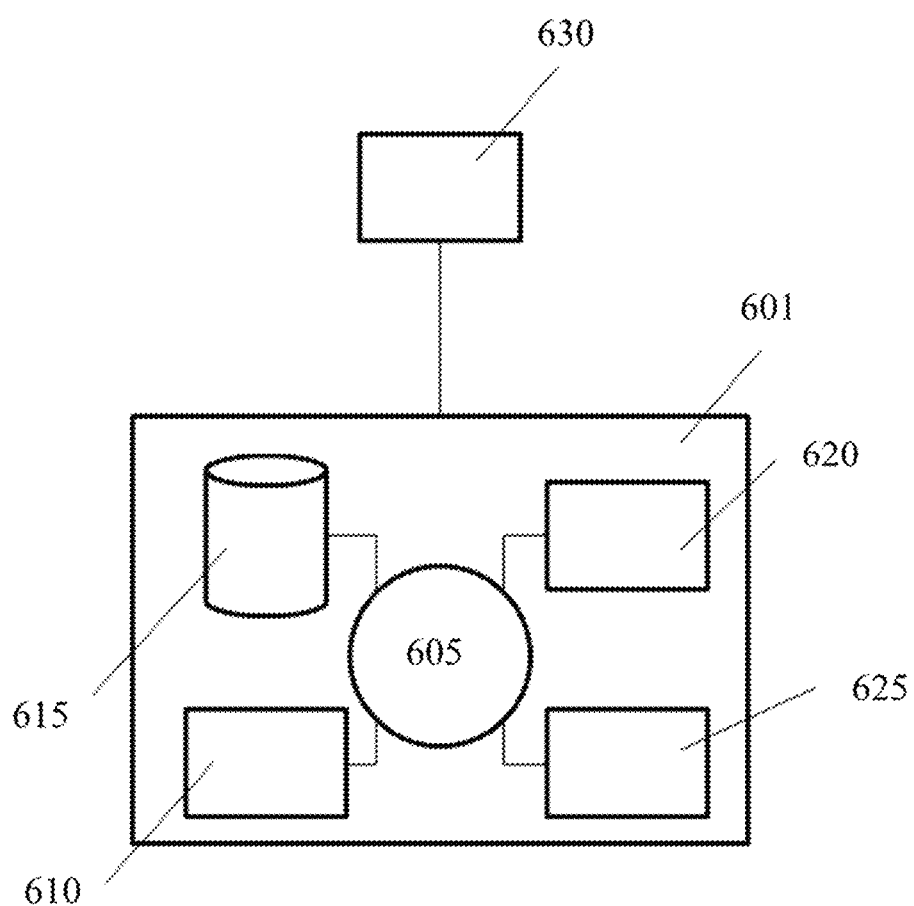
FIG. 6 shows a computer system 601 that is programmed or otherwise configured to regulate or analyze assays.

The present disclosure provides computer control systems that can be employed to conduct, regulate, analyze, communicate results from, or otherwise control assays and systems provided herein. FIG. 6 shows a computer system 601 that is programmed or otherwise configured to regulate or analyze assays. The computer system 601 can regulate, for example, fluid handling for conducting an assay, data collection of real-time reaction rates or end-point reaction outcomes, analysis of data, and transmission or display of data or results.

The computer system 601 includes a central processing unit (CPU, also "processor" and "computer processor"

herein) 605, which can be a single core or multi core processor, or a plurality of processors for parallel processing. The computer system 601 also includes memory or memory location 610 (e.g., random-access memory, read-only memory, flash memory), electronic storage unit 615 (e.g., hard disk), communication interface 620 (e.g., network adapter) for communicating with one or more other systems, and peripheral devices 625, such as cache, other memory, data storage and/or electronic display adapters. The memory 610, storage unit 615, interface 620 and peripheral devices 625 are in communication with the CPU 605 through a communication bus (solid lines), such as a motherboard. The storage unit 615 can be a data storage unit (or data repository) for storing data.

The CPU 605 can execute a sequence of machine-readable instructions, which can be embodied in a program or software. The instructions may be stored in a memory location, such as the memory 610. Examples of operations performed by the CPU 605 can include fetch, decode, execute, and writeback.

The storage unit 615 can store files, such as drivers, libraries and saved programs. The storage unit 615 can store programs generated by users and recorded sessions, as well as output(s) associated with the programs. The storage unit 615 can store user data, e.g., user preferences and user programs. The computer system 601 in some cases can include one or more additional data storage units that are external to the computer system 601, such as located on a remote server that is in communication with the computer system 601 through an intranet or the Internet.

The computer system 601 can be in communication with an assay system 630, including various elements of the assay system. Such elements can include sensors, fluid handling mechanisms (e.g., motors, valves, pumps), and actuators.

Methods as described herein can be implemented by way of machine (e.g., computer processor) executable code stored on an electronic storage location of the computer system 601, such as, for example, on the memory 610 or electronic storage unit 615. The machine executable or machine readable code can be provided in the form of software. During use, the code can be executed by the processor 605. In some cases, the code can be retrieved from the storage unit 615 and stored on the memory 610 for ready access by the processor 605. In some situations, the electronic storage unit 615 can be precluded, and machine-executable instructions are stored on memory 610.

The code can be pre-compiled and configured for use with a machine have a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 601, can be embodied in programming Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

EXAMPLES

Figure 7:
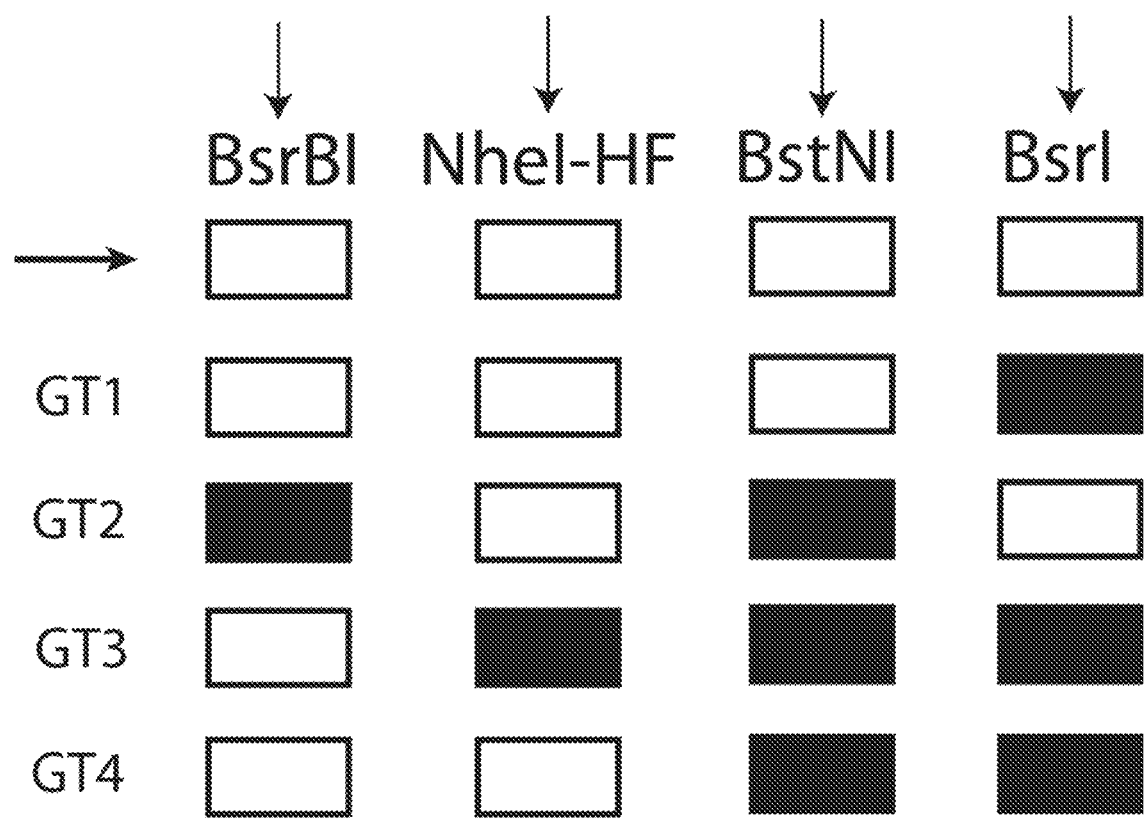
FIG. 7 shows an exemplary predicted amplification pattern.
Figure 8:
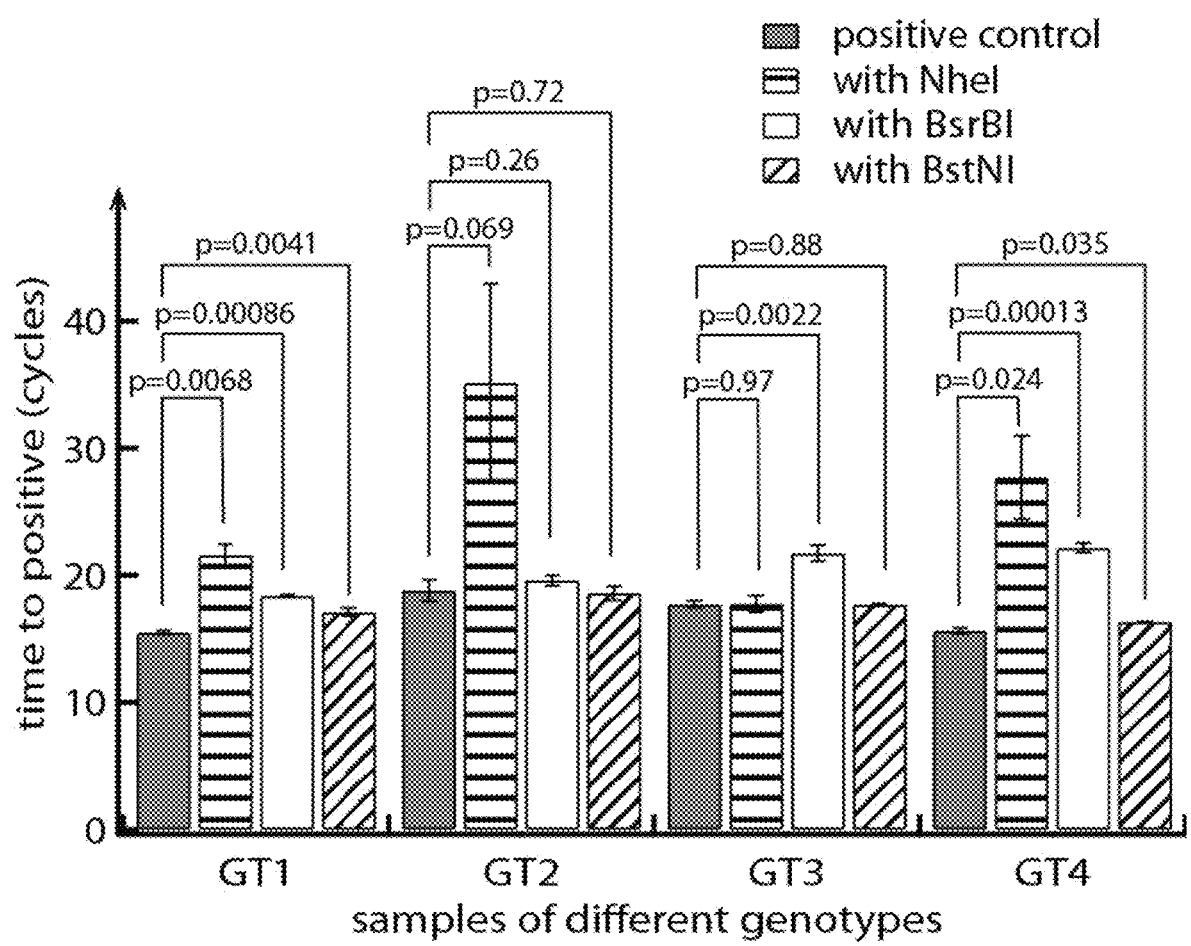
FIG. 8 shows exemplary results for time to positive from an assay.

Example 1—Real-Time Bulk HCV Genotyping Results Using RT-LAMP and Restriction Enzymes Three restriction enzymes (BsrBI, NehI, and BstNI) were selected based on hepatitis C virus (HCV) sequence and its variation in different genotypes. A set of customized LAMP primers targeting 5'UTR were designed. This set of primers was optimized to show high amplification efficiency for genotype 1, 2, 3 and 4. The cutting site of the restriction enzyme is inside the priming region (between B3 and F3; see Tsugunori Notomi, Hiroto Okayama, Harumi Masubuchi, Toshihiro Yonekawa, Keiko Watanabe, Nobuyuki Amino and Tetsu Hase, "Loop-mediated isothermal amplification of DNA", Nucleic Acids Res. 2000 Jun. 15; 28(12):E63), so that the enzyme cuts the product during amplification and leads to the inhibition or delay of the reaction. The alignment of RNA sequence, priming region and digestion site for NheI, BstNI, BsrBI, BsrI, and BcoDI is shown in FIG. 5A. The digestion site for the enzymes is specific to different genotypes so each enzyme specifically cuts certain genotypes. For example, the sequence which BsrBI cuts is CCGCTC, which with these RT-LAMP primers only exists in the amplicon of genotype 1, 3 and 4. As a result, the LAMP reaction with BsrBI is expected to be positive only for genotype 2. Based on the specificity of the enzymes, the predicted amplification pattern of LAMP-RE is shown in FIG. 7. For example, the digestion site for Hpy99I (A) only exists in the amplicon of subtype 1a, the digestion site for BstNI (B) only exists in subtype 1b, and BssSI (C) only digests the amplicon of subtype 1b; therefore, the combination of these enzymes enables the identification of subtype 1a and 1b. The expected pattern of positive and negative reaction results is shown in FIG. 7; each row stands for one HCV RNA genotype, each column stands for one restriction enzyme, black stands for "positive or not-delayed reaction," and white stands for "negative or delayed reaction." The time required for the LAMP reaction to change from negative (below intensity threshold) to positive (above intensity threshold) is shown in FIG. 8; positive controls are experiments in the absence of restriction enzyme, shown in solid grey as reference. Different restriction enzymes exhibit different capability for digestion, which results in different extent of delay. All experiments were performed in triplicates, with p-value shown above each bar in FIG. 8. In the real-time experiment, each cycle was set to be 1 minute and the fluorescence intensity was measured at the end of each cycle. Due to the time required for imaging (12 s per cycle), the cycle numbers did not reflect the absolute reaction time in the unit of minute. Real time RT-LAMP for HCV genotype 1 showed a significant delay (later time to positive than the positive control, last row) when it was combined with BsrBI, NehI, BstNI. For genotype 2, delayed reaction was observed with NehI. For Genotype 3 reaction with BsrBI was delayed and for genotype 4 with BsrBI and NehI.

To amplify HCV viral RNA using an RT-LAMP method on a real-time PCR machine without restriction enzymes, the RT-LAMP mix contained the following: 20 μL of RM, 2 μL of EM, 1 μL of FD, 4 μL of primer mixture (20 μM BIP/FIP, 10 μM LooP_B/Loop_F, and 2.5 μM B3/F3), various amounts of RNA template solution, and enough nuclease-free water to bring the volume to 40 μL. The solution was split into 10 μL each and loaded into 3 wells on the Eco real-time PCR (Illumina, CA) plate and heated at 63° C. for 50 min.

To amplify HCV viral RNA using RT-LAMP in the presence of restriction enzymes on a real-time PCR machine, the RT-LAMP mix contained the following: 20 μL of RM, 2 μL of EM, 1 μL of FD, 4 μL of primer mixture (20 μM BIP/FIP, 10 μM LooP_B/Loop_F, and 2.5 μM B3/F3), various amounts of RNA template solution, 4 μL diluted RE (20 fold diluted from purchased stock solution) and enough nuclease-free water to bring the volume to 40 μL. The solution was split into 10 μL each and loaded into 3 wells on the Eco real-time PCR plate and heated at 63° C. for 50 min.

Figure 9:
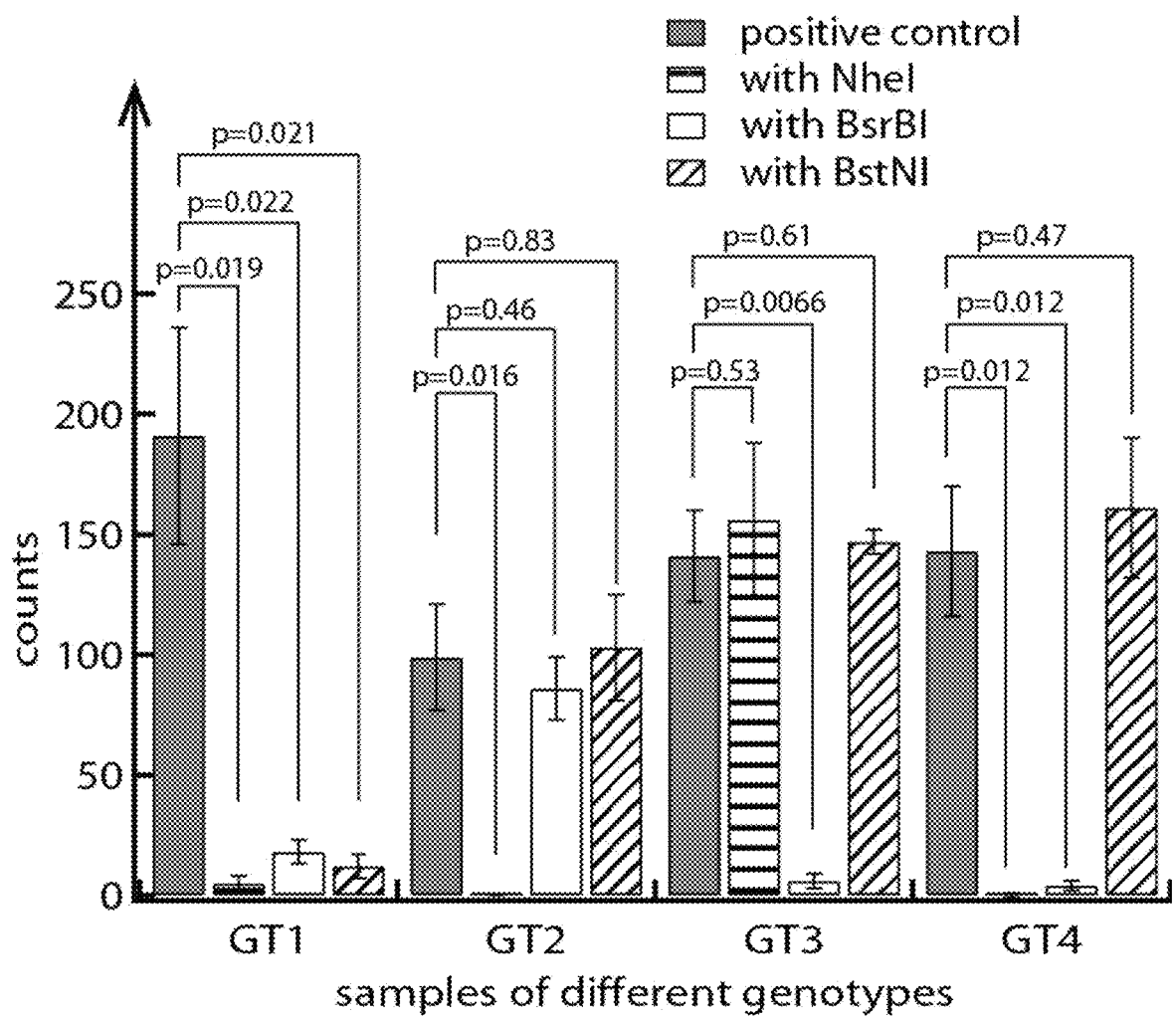
FIG. 9 shows exemplary results for number of counts from an assay.
Figure 10:
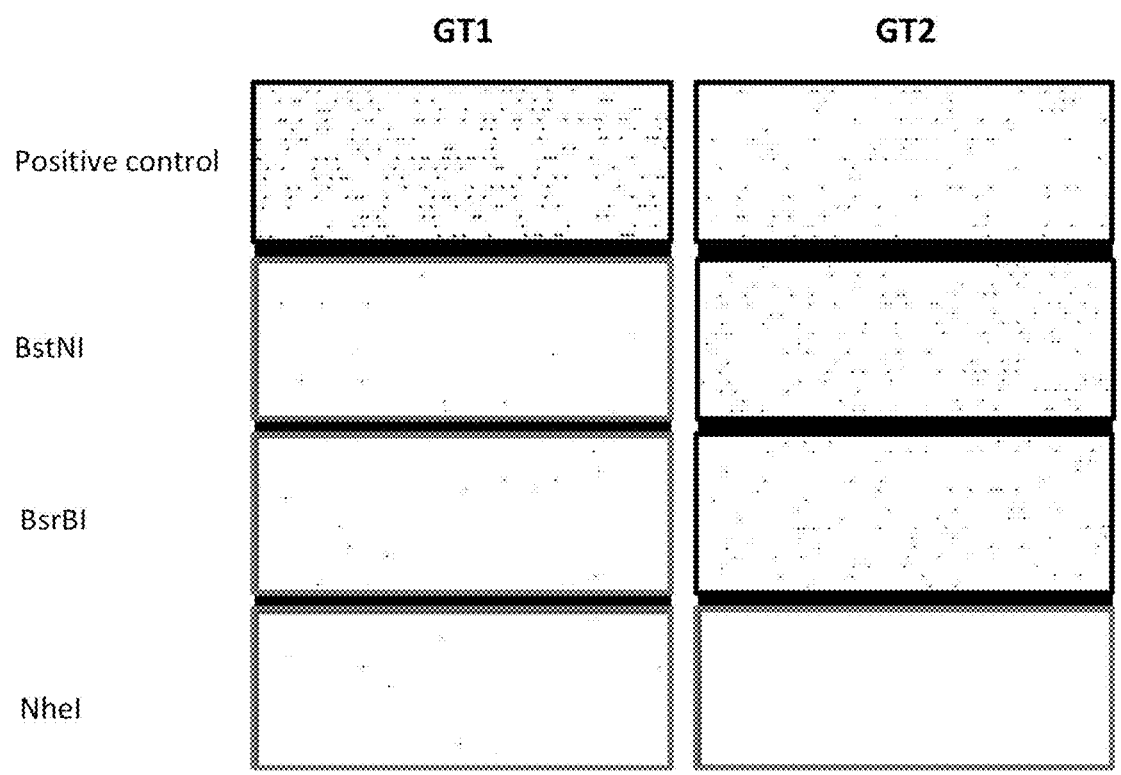
FIG. 10 shows exemplary digital RT-LAMP results on a SlipChip platform.
Figure 10:
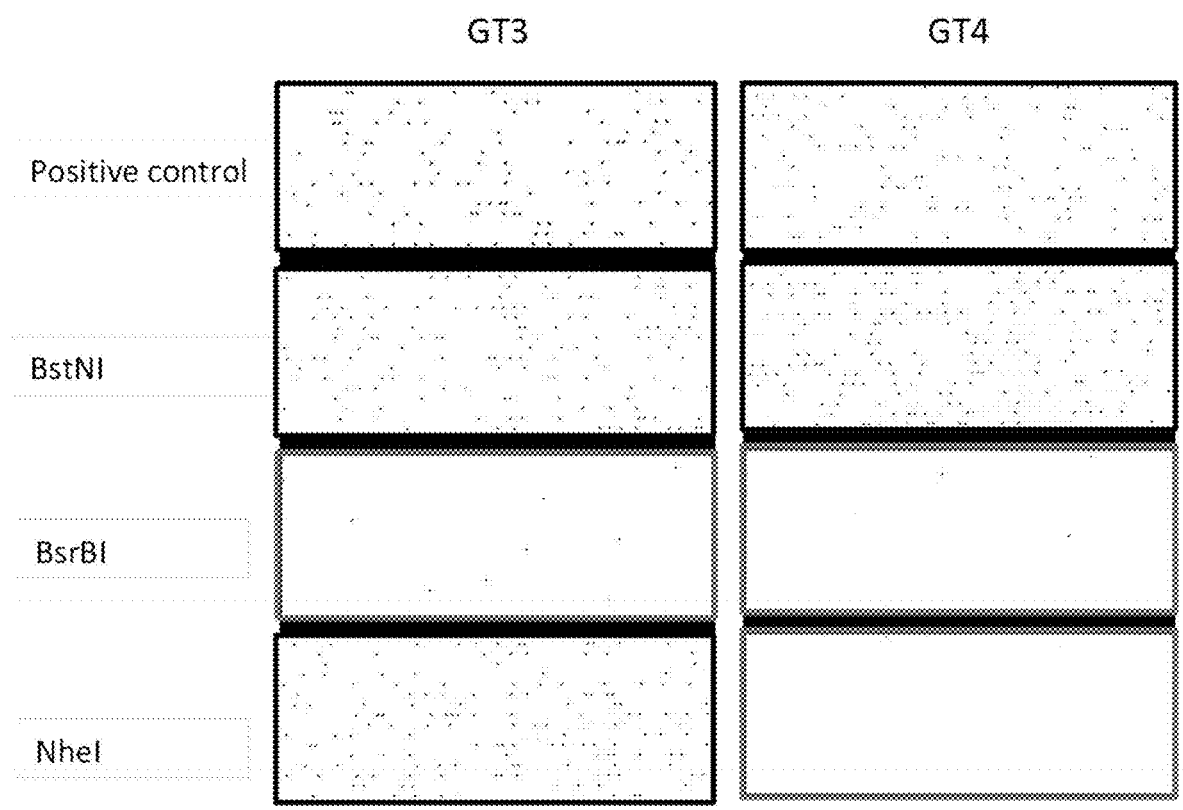

Example 2—End-Point Digital HCV Genotyping Results Using RT-LAMP and Restriction Enzymes Digestion was performed during amplification reaction for hepatitis C virus (HCV) RNA on a SlipChip platform. Digital RT-LAMP for HCV RNA was more thoroughly inhibited at the single RNA level compared to a bulk assay, as shown for example in FIG. 9 and FIG. 10. FIG. 9 shows digital RT-LAMP results with and without restriction enzymes for HCV genotyping. Positive controls are experiments in the absence of restriction enzyme, shown in solid grey as reference. Different restriction enzymes exhibit different capabilities for digestion, which results in different counts among genotypes. All experiments were performed in triplicates, with the p value shown above each bar. FIG. 10 shows digital RT-LAMP results (black dots are positive counts) on a SlipChip platform with genotype 1-4 HCV RNA and different restriction enzymes—NheI (fourth row), BsrBI (third row), and BstNI (second row)—as well as a positive control (first row). Digital RT-LAMP for HCV Genotype 1 RNA was inhibited by BsrBI, NheI, and BstNI at the single RNA level. Digital RT-LAMP for Genotype 2 RNA was only inhibited by NheI. Digital RT-LAMP for HCV Genotype 3 was only inhibited by BsrBI. Digital RT-LAMP for HCV Genotype 4 RNA was inhibited by both BsrBI and NheI. These results conform with the predicted pattern of inhibition based on genotype sequences and restriction enzyme targeting.

The SlipChip device used was single volume 1280-well device, designed and optimized based on "Bing Sun, Feng Shen, Stephanie E. McCalla, Jason E. Kreutz, Mikhail A. Karymov, and Rustem F. Ismagilov. Mechanistic evaluation of the pros and cons of digital RT-LAMP for HIV-1 viral load quantification on a microfluidic device and improved efficiency via a two-step digital protocol. Anal Chem 2013, 85(3): 1540-1546." The procedure of fabricating the SlipChip from soda-lime glass was based on the procedure described in "Feng Shen, Bing Sun, Jason E. Kreutz, Elena K. Davydova, Wenbin Du, Poluru L. Reddy, Loren J. Joseph, and Rustem F. Ismagilov, Multiplexed quantification of nucleic acids with large dynamic range using multivolume digital RT-PCR on a rotational SlipChip tested with HIV and hepatitis C viral load. J Am Chem Soc 133(44): 17705-17712" and "Wenbin Du, Liang Li, Kevin P. Nichols, and Rustem F Ismagilov, SlipChip, Lab Chip 2009, 9: 2286-2292." All features were etched to a depth of 55 um to make the volume of loading well equal to 3 nL.

To amplify HCV viral RNA using a RT-LAMP method on a real-time PCR machine, the RT-LAMP mix contained the following: 20 μL of RM, 2 μL of EM, 1 μL of FD, 4 μL of primer mixture (20 μM BIP/FIP, 10 μM LooP_B/Loop_F, and 2.5 μM B3/F3), 2 μL of BSA (20 mg/mL), various amounts of RNA template solution, 4 μL diluted restriction enzyme (except for positive control), and enough nuclease-free water to bring the volume to 40 μL. The solution was loaded onto a SlipChip and heated at 63° C. for 50 min on a house-built real-time instrument. Experiments were performed on a Bio-Rad PTC-200 thermocycler with a custom machined block. The block contains a flat 3"×3" portion onto which the devices are placed ensuring optimal thermal contact. The excitation light source used was a Philips Luxeon S (LXS8-PW30) 1315 lumen LED module with a Semrock filter (FF02-475). Image Acquisition was performed with a VX-29MG camera and a Zeiss Macro Planar T F2-100 mm lens. A Semrock filter (FF01-540) was used as an emission filter. The exposure time was set to be 500 ms and gain to be 1.

Figure 11A:
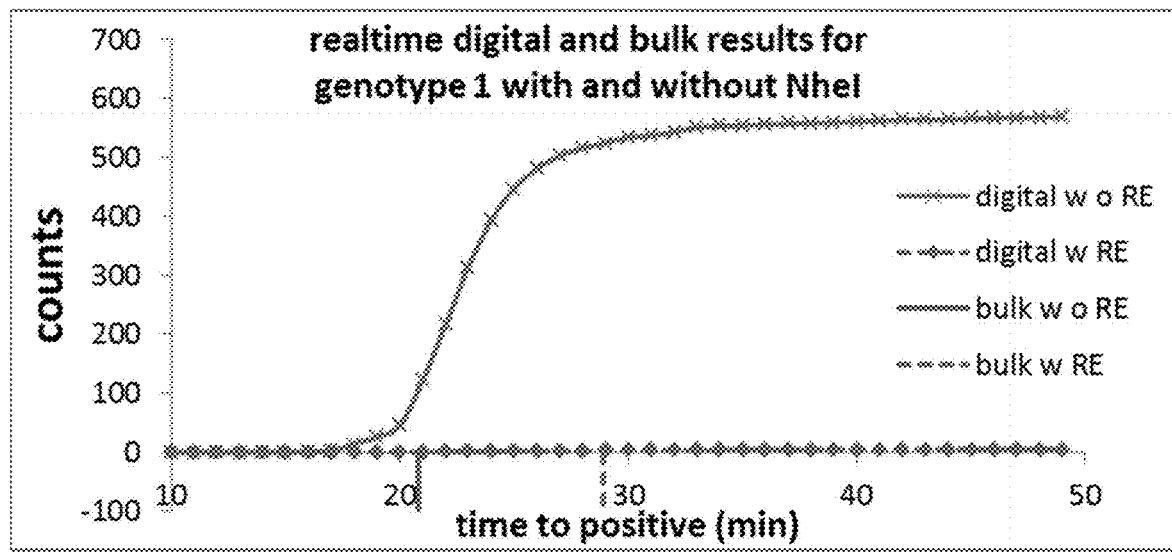
FIG. 11A shows exemplary results for real-time digital and bulk amplification of HCV genotype 1 with and without NheI.
Figure 11B:
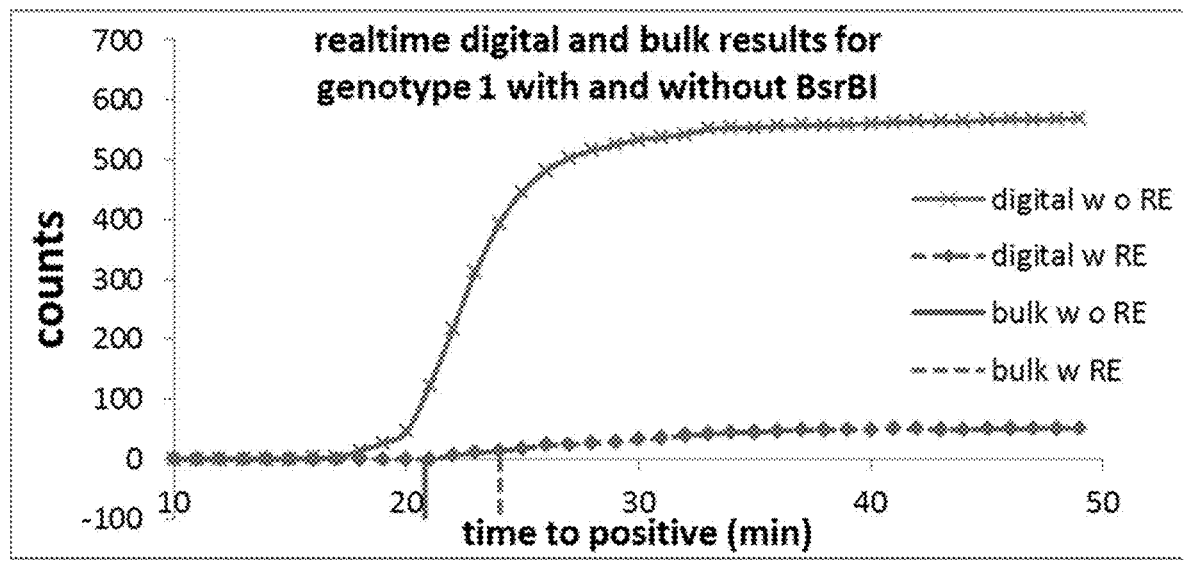
FIG. 11B shows exemplary results for real-time digital and bulk amplification of HCV genotype 1 with and without BsrBI.
Figure 11C:
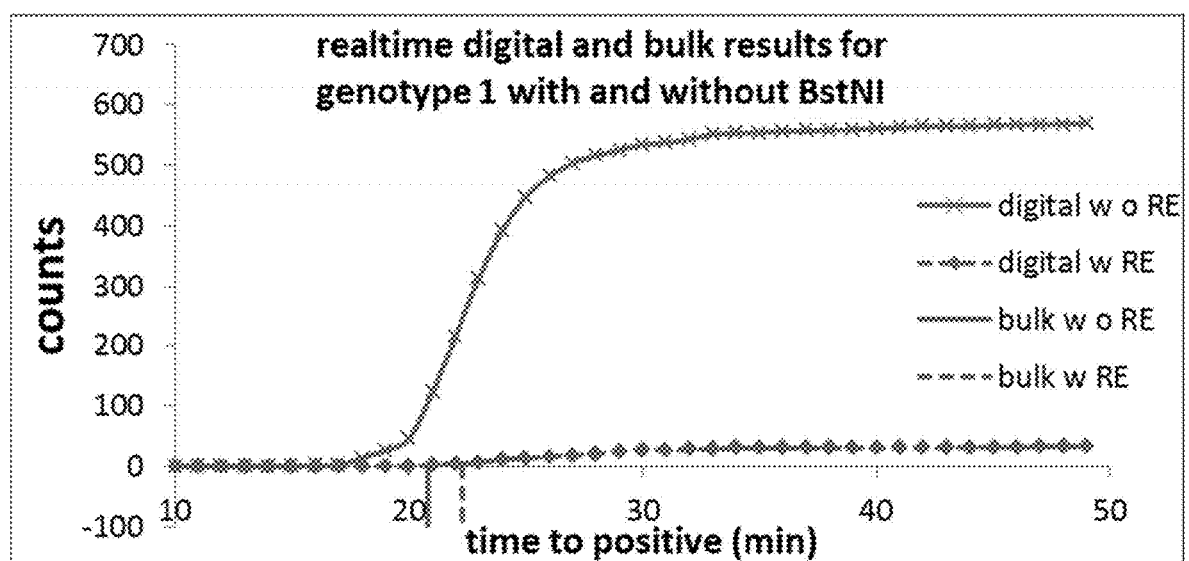
FIG. 11C shows exemplary results for real-time digital and bulk amplification of HCV genotype 1 with and without BstNI.
Figure 11D:
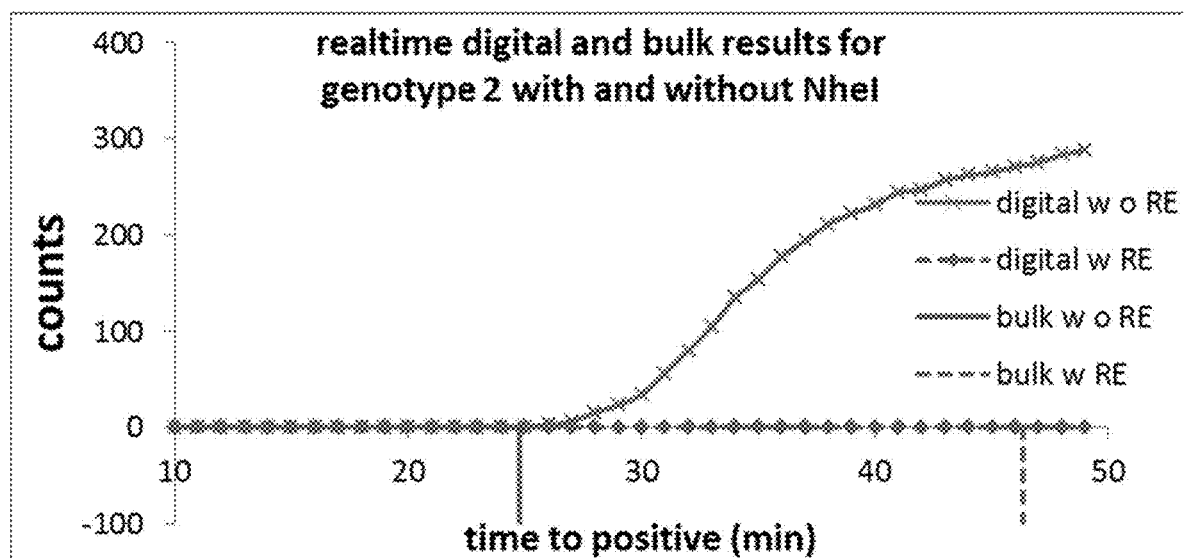
FIG. 11D shows exemplary results for real-time digital and bulk amplification of HCV genotype 2 with and without NheI.
Figure 11E:
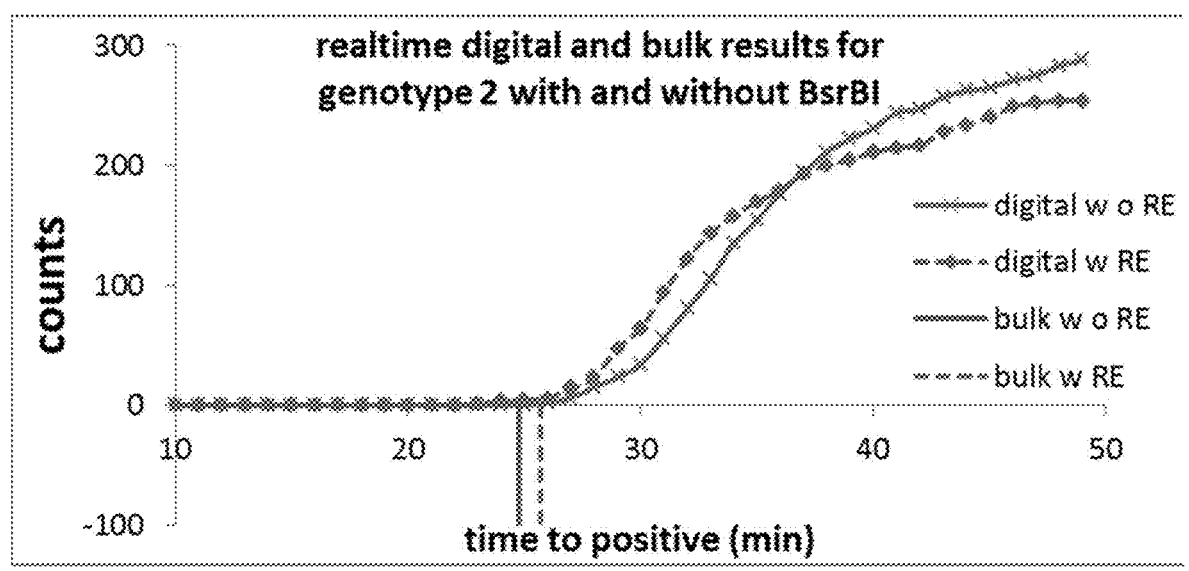
FIG. 11E shows exemplary results for real-time digital and bulk amplification of HCV genotype 2 with and without BsrBI.
Figure 11F:
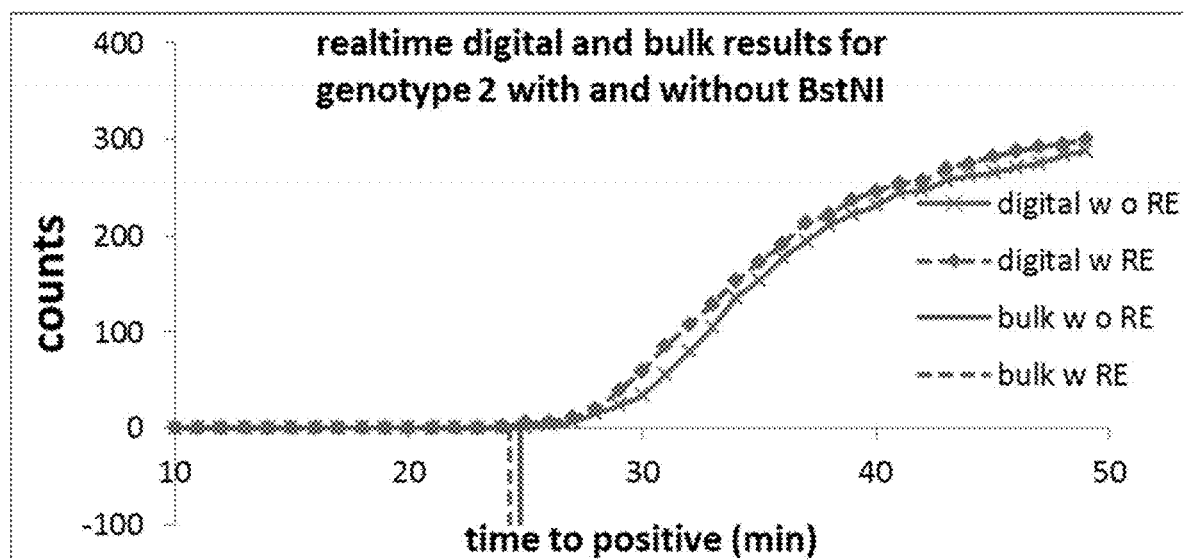
FIG. 11F shows exemplary results for real-time digital and bulk amplification of HCV genotype 2 with and without BstNI.
Figure 11G:
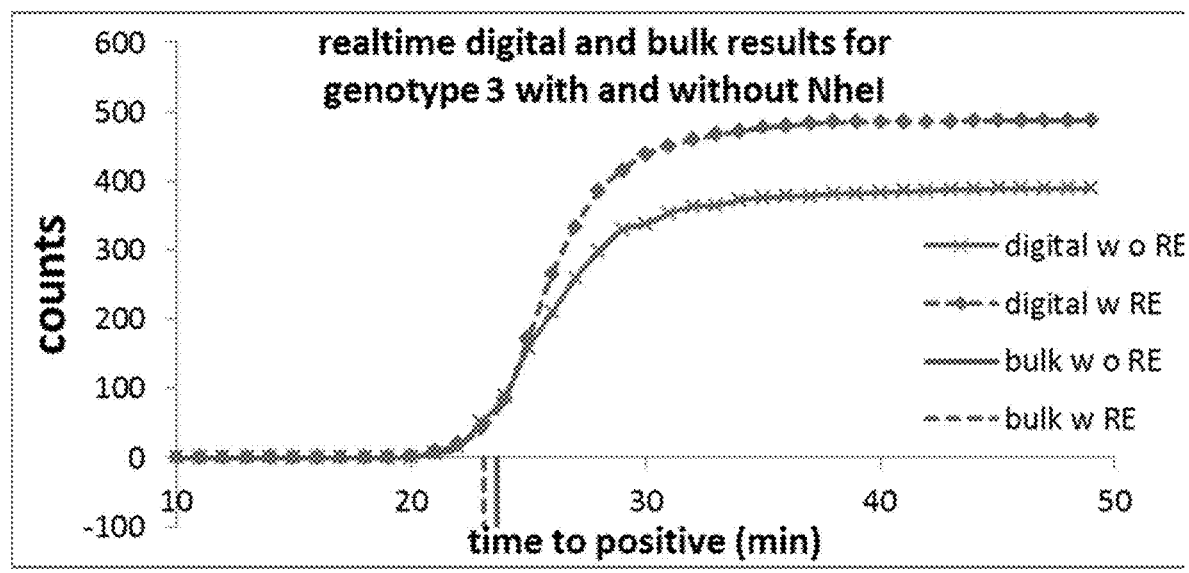
FIG. 11G shows exemplary results for real-time digital and bulk amplification of HCV genotype 3 with and without NheI.
Figure 11H:
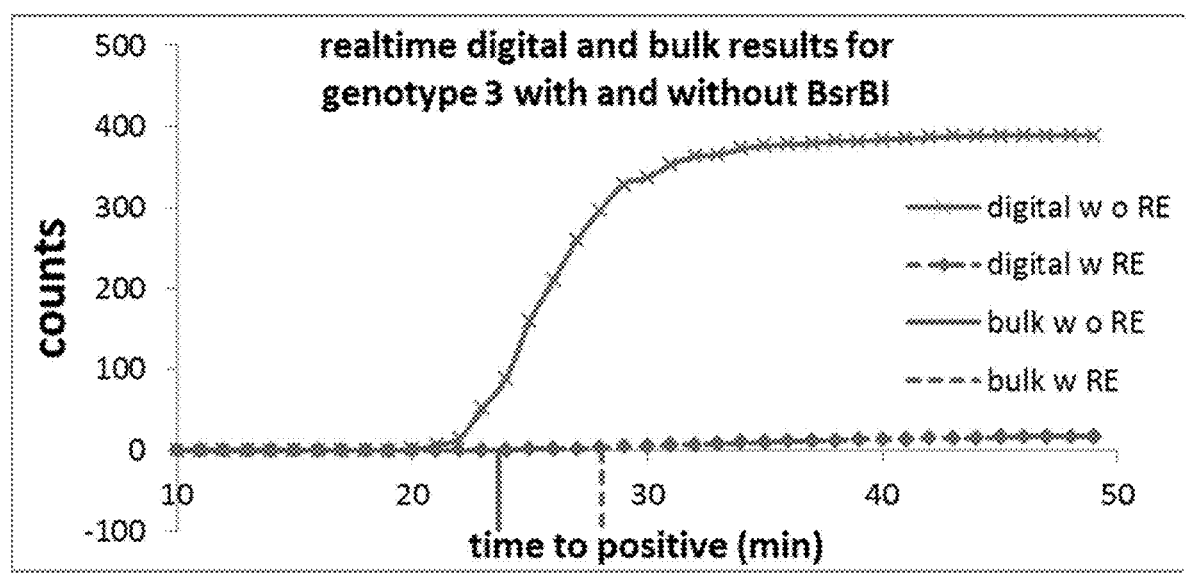
FIG. 11H shows exemplary results for real-time digital and bulk amplification of HCV genotype 3 with and without BsrBI.
Figure 11I:
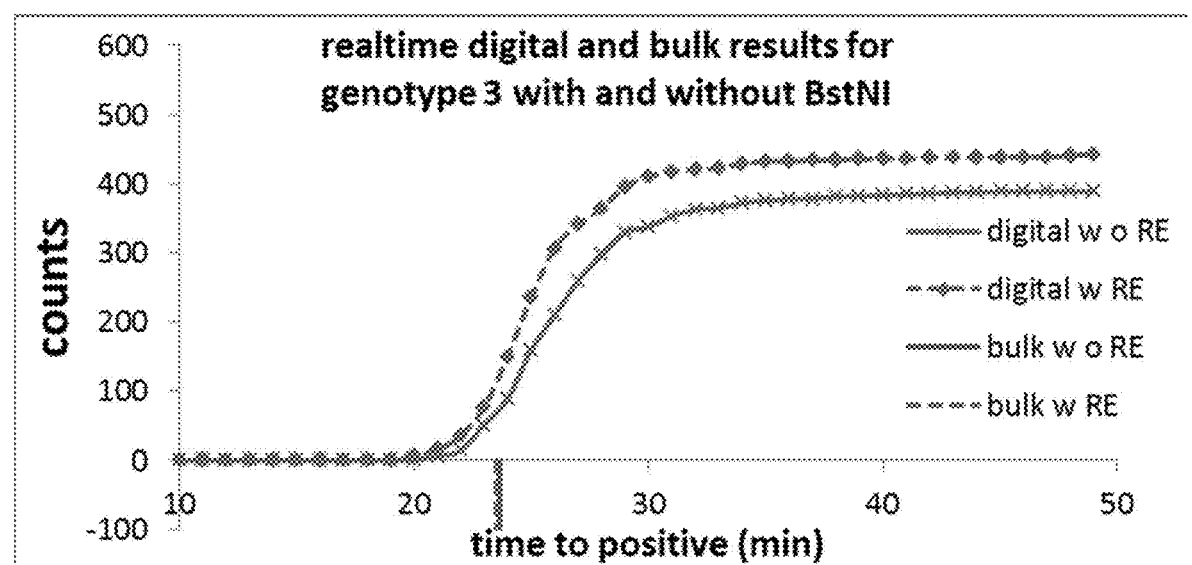
FIG. 11I shows exemplary results for real-time digital and bulk amplification of HCV genotype 3 with and without BstNI.
Figure 11J:
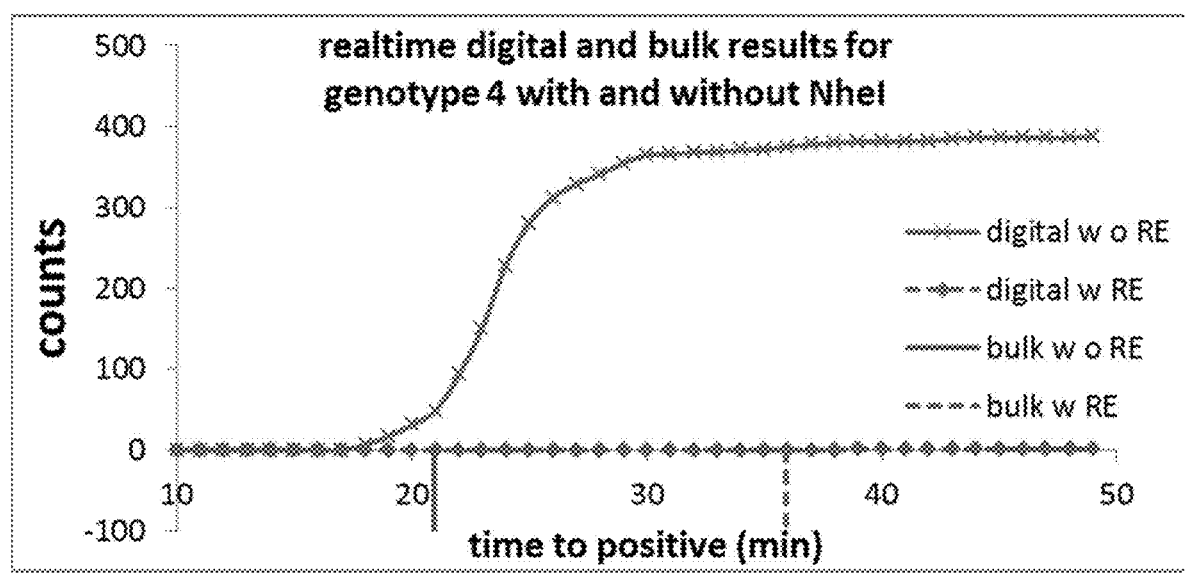
FIG. 11J shows exemplary results for real-time digital and bulk amplification of HCV genotype 4 with and without NheI.
Figure 11K:
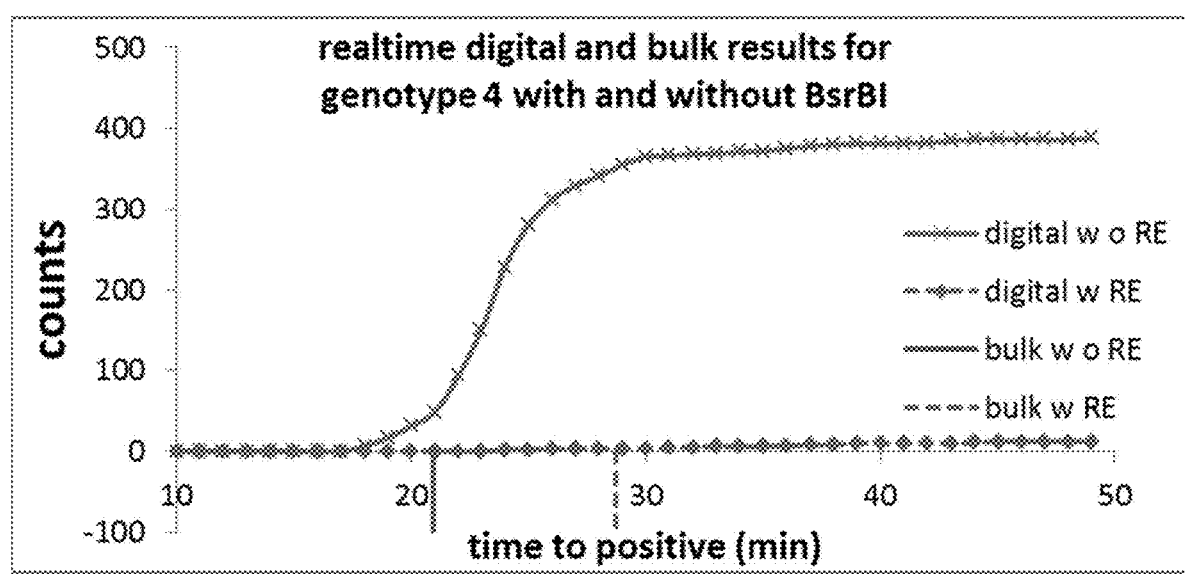
FIG. 11K shows exemplary results for real-time digital and bulk amplification of HCV genotype 4 with and without BsrBI.
Figure 11L:
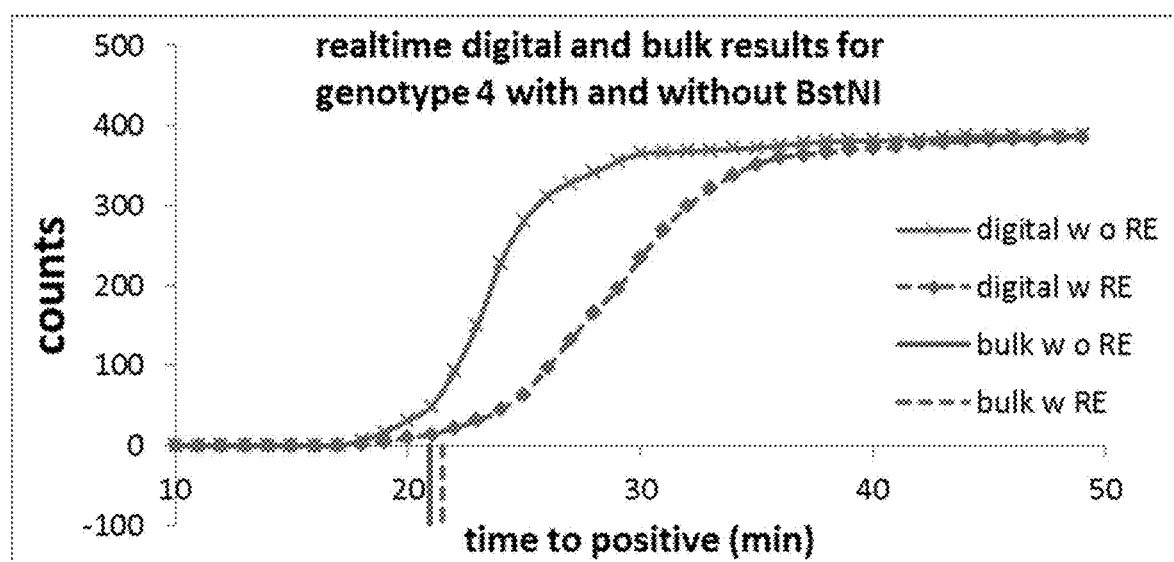
FIG. 11L shows exemplary results for real-time digital and bulk amplification of HCV genotype 4 with and without BstNI.

Example 3—Real-Time Digital HCV Genotyping Results Using RT-LAMP and Restriction Enzymes Experiments were performed as in the Example 2, except a house-built imaging instrument was used to monitor the reactions in individual wells of a SlipChip. Images were acquired every minute with an exposure time of 500 ms and gain of 1. Both counts and time to positive threshold changed with the addition of specific restriction enzymes, as shown in FIG. 11A-11L. FIG. 11 shows real-time digital HCV genotyping (genotype 1, 2, 3 and 4) results using RT-LAMP and restriction enzymes. The solid curve with markers in the first quadrant shows real-time monitored counts change over time without restriction enzyme, while the dashed curve with markers in the first quadrant shows real-time monitored counts change over time with restriction enzymes. The solid line without markers in the second quadrant shows time to positive (min) for bulk experiments without restriction enzymes, while the dashed line without markers in the second quadrant is time to positive (min) for bulk experiments with restriction enzymes. FIG. 11A shows real-time digital and bulk HCV genotyping results for Genotype 1 with and without restriction enzyme NheI. FIG. 11B shows real-time digital and bulk HCV genotyping results for Genotype 1 with and without restriction enzyme BsrBI. FIG. 11C shows real-time digital and bulk HCV genotyping results for Genotype 1 with and without restriction enzyme BstNI. FIG. 11D shows real-time digital and bulk HCV genotyping results for Genotype 2 with and without restriction enzyme NheI. FIG. 11E shows real-time digital and bulk HCV genotyping results for Genotype 2 with and without restriction enzyme BsrBI. FIG. 11F shows real-time digital and bulk HCV genotyping results for Genotype 2 with and without restriction enzyme BstNI. FIG. 11G shows real-time digital and bulk HCV genotyping results for Genotype 3 with and without restriction enzyme NheI. FIG. 11H shows real-time digital and bulk HCV genotyping results for Genotype 3 with and without restriction enzyme BsrBI. FIG. 11I shows real-time digital and bulk HCV genotyping results for Genotype 3 with and without restriction enzyme BstNI. FIG. 11J shows real-time digital and bulk HCV genotyping results for Genotype 4 with and without restriction enzyme NheI. FIG. 11K shows real-time digital and bulk HCV genotyping results for Genotype 4 with and without restriction enzyme BsrBI. FIG. 11L shows real-time digital and bulk HCV genotyping results for Genotype 4 with and without restriction enzyme BstNI. Real time digital traces can be analyzed in multiple ways in this methodology, including end-point analysis, time-course analysis, analysis of the area-under-the-curve, and so forth.

Example 4—Using Oligonucleotide Inhibitors to Selectively Delay a HCV LAMP Amplification Reaction Two oligonucleotide inhibitors were designed with the same sequence except at four mutation points (underlined). The four mutations were introduced in such a way that the melting temperatures (Tm) of the two oligonucleotides (hybridized to DNA) are the same. The sequences of the oligonucleotides are:

```
Matched inhibitor:
                                         (Seq ID No: 6)
CGGGGCACTCGCAAGCACCCTATCAGGCAGTACCACAAGGCCTTTCGCGA

CCCAACTGAT

Mismatched inhibitor:
                                         (Seq ID No: 7)
CGGGGCACTCGCAAGCACTCTACCAGACAGTGCCACAAGGCCTTTCGCGA

CCCAACTGAT
```

The results have been summarized in Table 1:

TABLE 1

Time-to-positive results for real-time RT-LAMP with different oligonucleotide inhibitors for HCV RNA

| Sample | Time to positive/cycle (std. dev.) |
|---|---|
| Positive Control | 17.8 (0.23) |
| With matched inhibitor | 31.9 (0.79) |
| With mismatched inhibitor (4 mismatches) | 23.1 (0.16) |
| Neg Ctrl. | 54.3 (13.38) |

Here time-to-positive is defined as the time required for the LAMP reaction to change from negative (below intensity threshold) to positive (above intensity threshold). In the real-time experiment, each cycle was set to be 1 minute and the fluorescence intensity was measured at the end of each cycle. Due to the time required for imaging (12 s per cycle), the cycle numbers did not reflect the absolute reaction time in the unit of minute.

Both matched and mismatched inhibitors have delayed the reaction; however the mismatched inhibitors displayed less inhibition effect, as expected. The matched and mismatched primers were specific (perfectly matched) to different genotypes, resulting in different inhibition effect to the same RNA. This difference leads to a differentiation between genotypes. This difference led to the differentiation between genotypes. For example, in the reaction where there was oligonucleotide inhibitor specific to Genotype 1 (matched inhibitor in this example), when Genotype 1 HCV RNA was introduced into the reaction a strong inhibition was observed. When the inhibitor is not specific to Genotype 1 (such as the mismatched inhibitor in this example) or is specific to other genotypes, when Genotype 1 HCV RNA was introduced, little inhibition was observed.

To amplify HCV RNA one-step RT-LAMP with oligonucleotide inhibitors, per each 40 µL the RT-LAMP mix contained the following: 20 µL of RM, 2 µL of BSA (20 mg/mL), 2 µL of EM, 1 µL of FD, 4 µL of primer mixture (20 µM BIP/FIP, 10 µM LooP_B/Loop_F, and 2.5 µM B3/F3), 2 µL of RNase Inhibitor (20 U/µl), 4 µL of HCV genotype 1 RNA, 1 µL of 80 µM oligonucleotide inhibitor, and enough nuclease-free water to bring the volume to 40 µL. The RNA was extracted from 140 µL of plasma (AcroMetrix® HCV Genotyping Panel) using QIAamp Viral RNA Mini Kit (Qiagen) with an elution volume of 60 µL. Loopamp® RT-LAMP mix was purchased from SA Scientific. The solution was split into 10 µL each and loaded onto Eco real-time PCR machine and heated at 63° C. for 60 cycles (1 min/cycle).

Example 5—Using Oligonucleotide Inhibitors Together with RT-LAMP Reaction for HCV RNA Genotype 1 in Digital SlipChip Device An experiment was also performed at single molecule level on a SlipChip, as shown in FIG. 12. The reaction mix as detailed in Example 4 was used. The digital experiments showed improved specificity compared to bulk experiment. The specific oligonucleotide inhibitor completely or nearly completely stopped the reaction (very few counts after reaction), while the mismatched oligonucleotide inhibitor did not change the count much (similar number of counts to positive control without inhibitors). FIG. 12 shows digital RT-LAMP for HCV RNA Genotype 1 results on SlipChip.

Figure 12A:
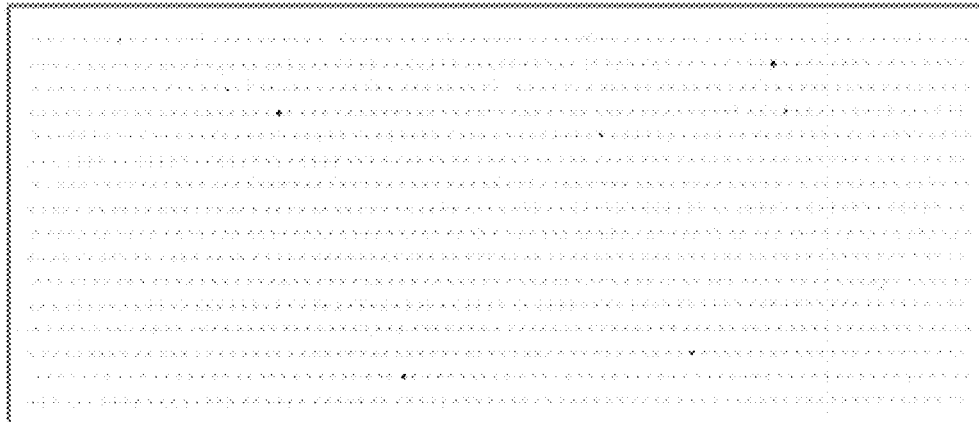
FIG. 12A shows exemplary results from digital RT-LAMP for HCV RNA Genotype 1 with a matched inhibitor on a SlipChip device.
Figure 12B:
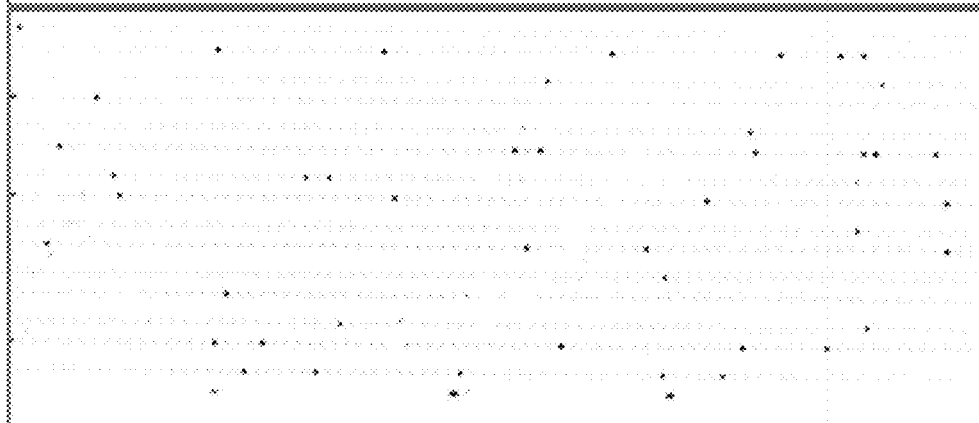
FIG. 12B shows exemplary results from digital RT-LAMP for HCV RNA Genotype 1 with a mismatched inhibitor on a SlipChip device.
Figure 12C:
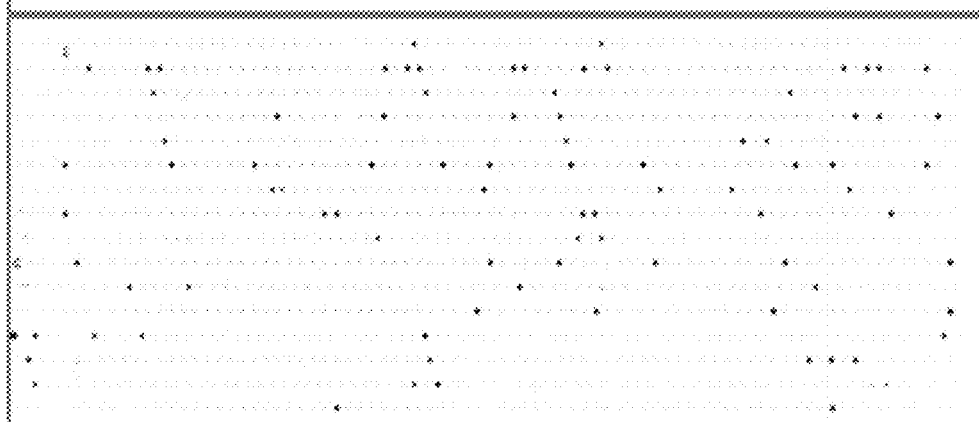
FIG. 12C shows exemplary results from digital RT-LAMP for HCV RNA Genotype 1 with no inhibitor on a SlipChip device.

Black dots represent positive counts. FIG. 12A shows results with matched inhibitor, FIG. 12B shows results with mismatched inhibitor, and FIG. 12C shows results from a positive control without inhibitors.

To perform HCV RNA one-step RT-LAMP with oligonucleotide inhibitors on a SlipChip, per each 40 μL the RT-LAMP mix contained the following: 20 μL of RM, 2 μL of BSA (20 mg/mL), 2 μL of EM, 1 μL of FD, 4 μL of primer mixture (20 μM BIP/FIP, 10 μM LooP_B/Loop_F, and 2.5 μM B3/F3), 2 μL of RNase Inhibitor (20 U/μl), 4 μL of HCV genotype 1 RNA, 1 μL of 80 μM oligo inhibitor and enough nuclease-free water to bring the volume to 40 μL. The RNA was extracted from 140 μL of plasma (AcroMetrix® HCV Genotyping Panel) using QIAamp Viral RNA Mini Kit (Qiagen) with an elution volume of 60 μL. Loopamp® RT-LAMP mix was purchased from SA Scientific. The solution was directly loaded onto SlipChip devices and subject to heating at 63° C. for 50 minutes.

Example 6—Real-Time Bulk HCV Genotyping Results Using NASBA and Restriction Enzymes Seven restriction enzymes—NheI, BsrBI, ApoI, BsrGI, NruI, BseYI and BstXI—were selected based on HCV sequence variation among different genotypes (Bsp681 is an isoschizomer of NruI having the same recognition and cleavage specificity). A set of customized nucleic acid sequence based amplification (NASBA) primers and molecular beacon probes targeting 5'UTR were designed; selected sequences are showed in Table 2, wherein bold type indicates the sequence of the bacteriophage T7 DNA-dependent RNA polymerase promoter and stem sequences are indicated with underlines.

TABLE 2

NASBA primers and molecular beacon probe targeting 5'UTR.

| Name | Sequence 5'-3' |
| --- | --- |
| 5'UTR_P2_NASBA_HCV_forward | GTCTAGCCATGGCGTTAGTA (Seq ID No: 2) |
| 5'UTR_P1_NASBA_HCV_reverse_1 | taatacgactcactagggCAAGCACCCTATCAGGCAGTA (Seq ID No: 8) |
| 5'UTR_P1_NASBA_HCV_reverse_2 | taattctaatacgactcactatagggCAAGCACCCTATCAGGCAGTA (Seq ID No: 9) |
| 5'UTR_probe_NASBA_HCV_sense_1 | /FAM/<u>CGTACG</u>GTCTGCGGAACCGGTGAGTA<u>CGTACG</u>/BHQ1/ |

TABLE 2-continued

NASBA primers and molecular beacon probe targeting 5'UTR.

| Name | Sequence 5'-3' |
| --- | --- |
| | (Seq ID No: 10) |
| 5'UTR_probe_NASBA_HCV_sense_2 | /FAM/<u>CGATCG</u>AGCCATAGTGGTCTGCGGAACCGGT<u>CGATCG</u>/BHQ1/ (Seq ID No: 3) |

Figure 13:
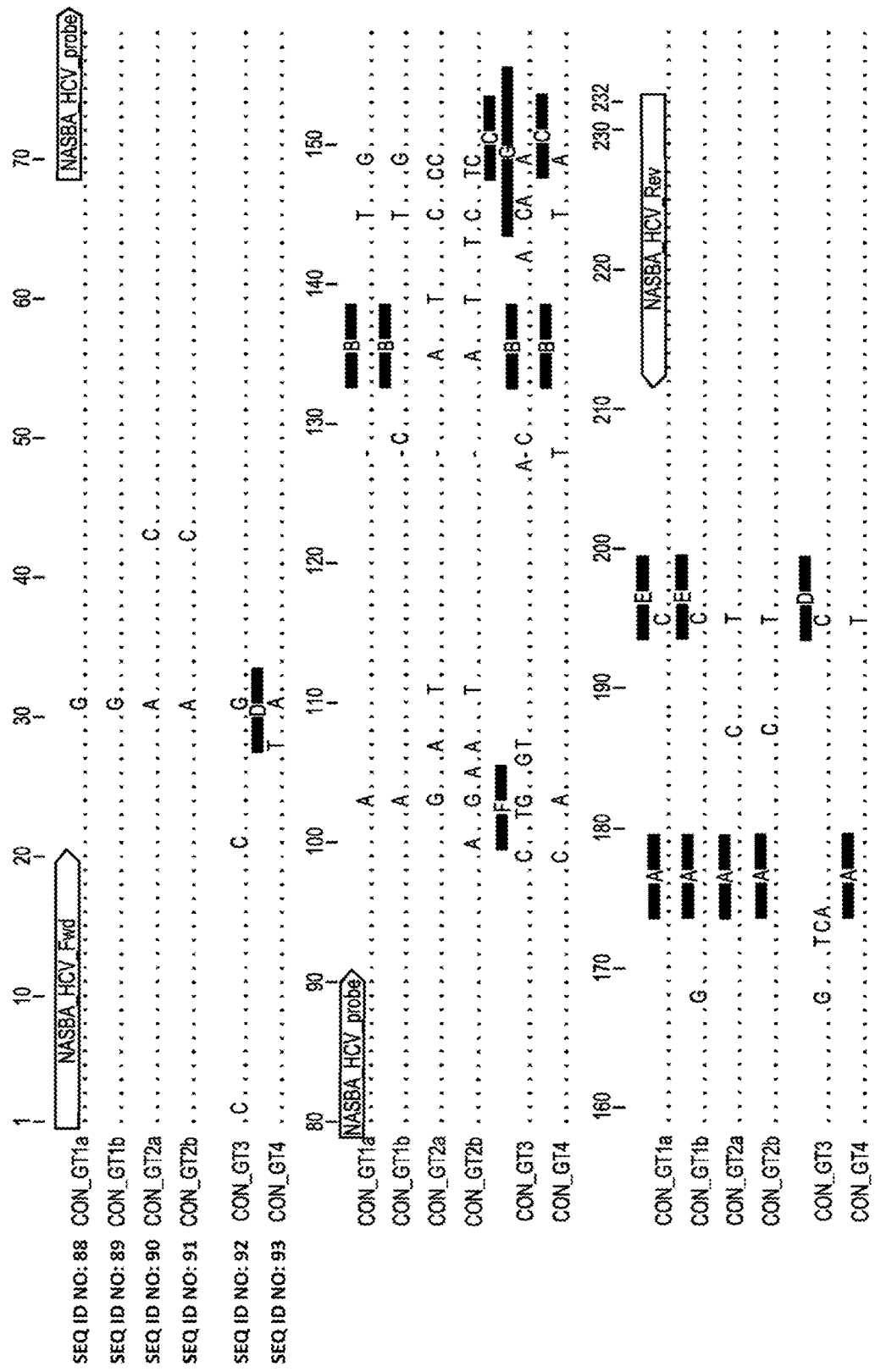
FIG. 13 shows exemplary alignment of RNA sequences for genotypes 1, 2, 3 and 4, priming and molecular beacon probe regions, and digestion sites of NheI, BsrBI, ApoI, BsrGI, NruI (or Bsp68I), BseYI and BstXI.
Figure 14:
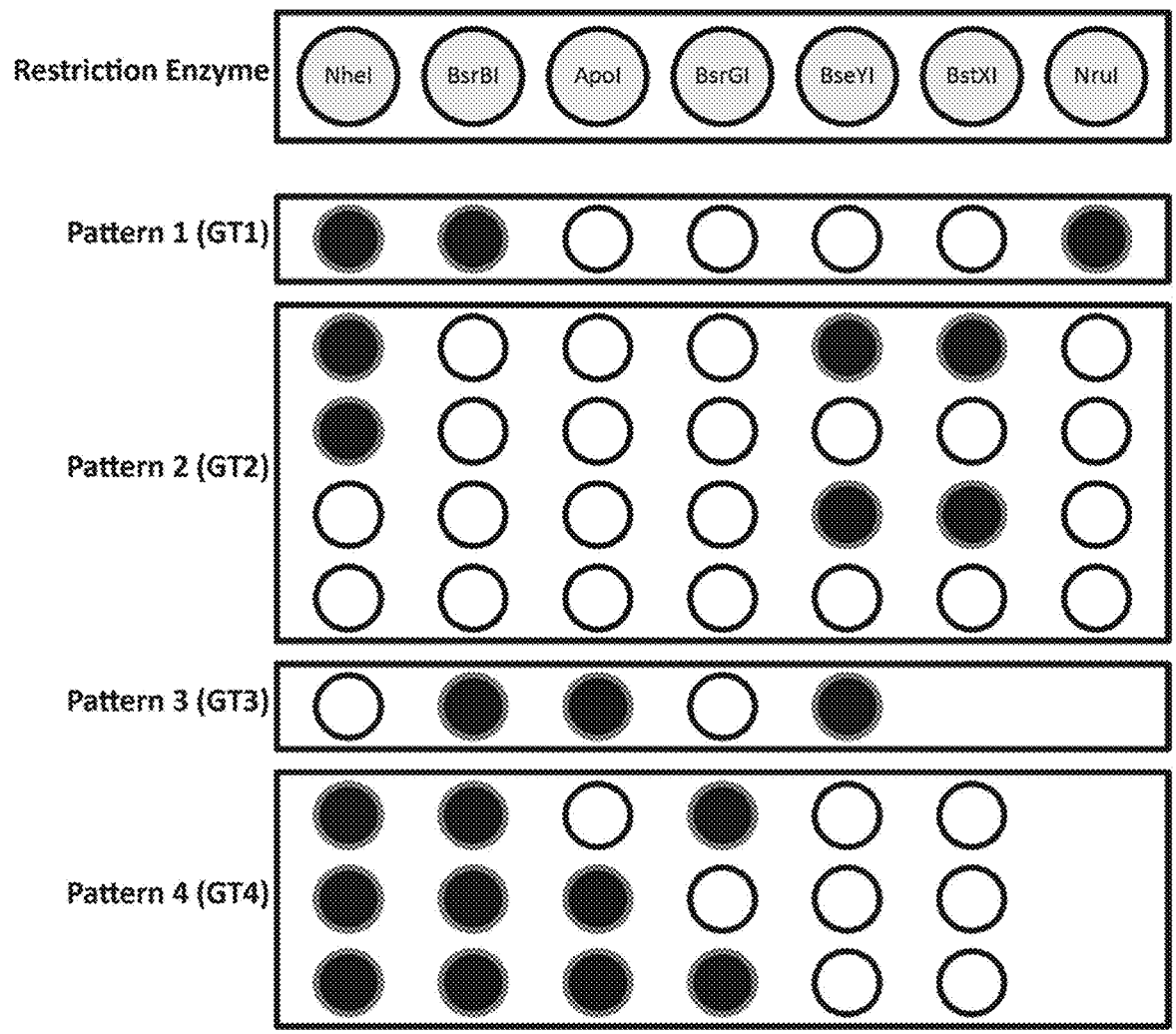
FIG. 14 shows exemplary expected amplification results from an assay.

The cutting site of the restriction enzymes is included in the produced amplicon (231 pb) inside the primer region, so that, for example, the enzyme cuts the product during amplification and leads to inhibition or delay of the reaction. Alignment of RNA sequences for genotypes 1, 2, 3 and 4, priming and molecular beacon probe regions, and digestion sites of NheI, BsrBI, ApoI, BsrGI, NruI (or Bsp681), BseYI and BstXI is shown in FIG. 13. In FIG. 13, Consensus genotype 1a (CON_GT1a); Consensus genotype 1b (CON_GT1b); Consensus genotype 2a (CON_GT2a); Consensus genotype 2b (CON_GT2b); Consensus genotype 3 (CON_GT3); Consensus genotype 4 (CON_GT4); A: NheI; B: BsrBI; C: ApoI; D: BsrGI; E: NruI; F: BseYI; G: BstXI. Based on the specificity of the enzymes, the pattern of NASBA-restriction enzyme (NASBA-RE) results were predicted as shown in FIG. 14. In FIG. 14, black circles represent negative NASBA reactions (inhibited reaction in the presence of the restriction enzyme shown on the top of the column) and white circles represent positive NASBA reactions (non-inhibited reaction in the presence of the restriction shown on the top of the column); each row represents a unique combination (pattern or fingerprint) of positive and negative NASBA reactions in the presence of different restriction enzymes associated with one HCV genotype. Multiple patterns of inhibition are possible for some genotypes due to the existence of mutations and multiple sequences within each genotype.

By using the proposed pattern, and based on multiple nucleotide sequence alignment obtained from HCV Los Alamos database, we analyzed the coverage for Genotype 1 (subtypes 1a and 1b), Genotype 2, Genotype 3 (subtype 3a) and Genotype 4. As shown in Table 3, in silico analysis showed that 97.6% (n=1,269) of HCV sequences were correctly typed; 2% (n=26) of sequences are untyped; and 0.4% (n=5) of sequences are mistyped. In Table 3, N seq stands for the number of sequences; Pattern 1, 2, 3 and 4 are described in FIG. 14; No Pattern includes the sequences that are not described by any of the predicted patterns in FIG. 14. Numbers of sequences and percentages in shaded boxes (Pattern 1 GT1, Pattern 2 GT2, Pattern 3 GT3, and Pattern 4 GT4) describe genotypes under the correct expected pattern.

TABLE 3

HCV genotype coverage based on predicted patterns.

| HCV Genotype (subtype) | N Seq | Pattern 1 | Pattern 2 | Pattern 3 | Pattern 4 | No Pattern |
| --- | --- | --- | --- | --- | --- | --- |
| GT1 (1a + 1b) | 869 | 861 (99.1%) | 1 (0.1%) | 0 (0.0%) | 1 (0.1%) | 6 (0.7%) |
| GT2 | 190 | 0 (0.0%) | 181 (95.3%) | 0 (0.0%) | 0 (0.0%) | 9 (4.7%) |

TABLE 3-continued

HCV genotype coverage based on predicted patterns.

| HCV Genotype (subtype) | N Seq | Pattern 1 | Pattern 2 | Pattern 3 | Pattern 4 | No Pattern |
|---|---|---|---|---|---|---|
| GT3 (3a) | 134 | 2 (1.5%) | 0 (0.0%) | 125 (93.3%) | 1 (0.7%) | 6 (4.5%) |
| GT4 | 107 | 0 (0.0%) | 0 (0.0%) | 0 (0.0%) | 102 (95.3%) | 5 (4.7%) |

Figure 15:
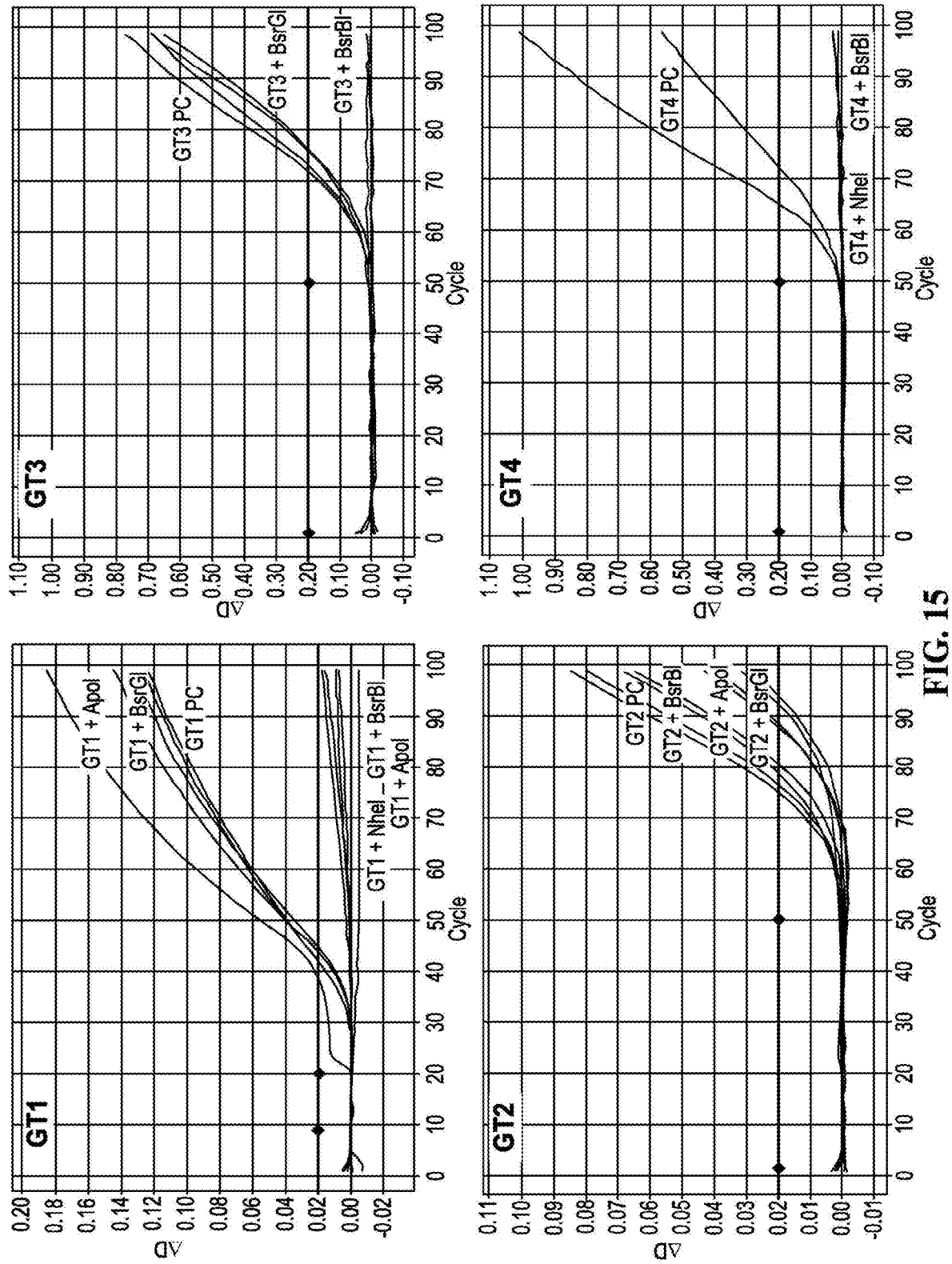
FIG. 15 shows exemplary results for the time required for NASBA reaction to change from negative.

The time required for NASBA reaction to change from negative (below intensity threshold) to positive (above intensity threshold) is shown in FIG. 15 and Table 4. The primer mix for 5'UTR NASBA reaction used in this example includes: 5'UTR_P2_NASBA_HCV_forward, 5'UTR_P1_NASBA_HCV_reverse_1 and 5'UTR_probe_NASBA_HCV_sense_1. Table 5 shows real-time NASBA results with and without restriction enzymes for HCV genotyping with improved NASBA reaction. The primer mix for 5'UTR NASBA reaction used for these results includes: 5'UTR_P2_NASBA_HCV_forward, 5'UTR_P1_NASBA_HCV_reverse_2 and 5'UTR_probe_NASBA_HCV_sense_2. NruI was replaced by BstEII. Predicted (in silico) negative or delayed results are shown in bold.

TABLE 4

Real-time NASBA results with and without restriction enzymes for HCV genotyping.

| Restriction Enzyme | HCV RNA (Cq) | | | |
|---|---|---|---|---|
| | GT1 | GT2 | GT3 | GT4 |
| Non-RE (PC) | 41.7 | 88.9 | 72.8 | 71.6 |
| | 41.7 | 90.6 | 71.8 | 64.9 |
| NheI | neg | NT | NT | neg |
| | neg | NT | NT | neg |
| BsrBI | neg | 78.3 | neg | neg |
| | neg | 80.0 | neg | neg |
| ApoI | 38.2 | 94.6 | NT | NT |
| | neg | 91.8 | NT | NT |
| BsrGI | 43.6 | 76.3 | 76.5 | NT |
| | 44.5 | 75.2 | 76.5 | NT |

TABLE 5

Real-time NASBA results with and without restriction enzymes for HCV genotyping with improved NASBA reaction.

| Restriction Enzyme | Time to Positive in minutes (SD) | | | |
|---|---|---|---|---|
| | GT1 | GT2 | GT3 | GT4 |
| Non-RE (PC) | 26.6 (0.2) | 30.9 (0.7) | 29.2 (1.2) | 27.3 (0.1) |
| NheI-HF | Neg | Neg | 35.4 (7.1) | 64.2 (20.3) |
| BsrBI | Neg | 42.6 (1.5) | Neg | 42.8 (0.3) |
| ApoI | 27.1 (0.2) | 34.8 (2.5) | Neg | 47.5 (7.1) |
| BsrGI | 33.0 (1.2) | 48.9 (1.8) | 45.4 (17.6) | 46.2 (6.3) |
| BstEII | 30.8 (0.4) | 44.5 (6.9) | Neg | 31.5 (1.3) |
| BstXI | 28.2 (0.8) | 37.0 (0.2) | Neg | 34.4 (3.3) |
| Bsp681 | Neg | 40.2 (3.3) | Neg | 45.8 (0.1) |

In the real-time experiment, each cycle was set to be 1 minute and the fluorescence intensity was measured at the end of each cycle. Due to the time required for imaging (additional 12 seconds per cycle), the cycle numbers did not reflect the absolute reaction time in the unit of minute. The performance of this idea has been evaluated by testing NheI, BsrBI, ApoI and BsrGI against HCV genotypes 1, 2, 3 and 4. Preliminary results showed that real time NASBA reactions for HCV Genotype 1 are inhibited in combination with BsrBI, NehI, and are not inhibited in the presence of ApoI and BsrGI. One of the replicates was also inhibited in the presence of ApoI. For Genotype 2, no negative reactions were observed in the presence of BsrBI, ApoI and BsrGI. For Genotype 3, reaction with BsrBI was negative and positive with BsrGI, and for Genotype 4 the reaction was negative with BsrBI and NehI.

After optimization of primers/probe for 5'UTR HCV NASBA reaction the assay was evaluated with HCV GT1, GT2, GT3 and GT4 in the presence of NheI-HF, BsrBI, ApoI, BsrGI, BstEII, BstXI and Bsp681 (restriction enzymes were selected based on Table 5). Time to positive obtained in the presence of the restriction enzymes were compared to a positive control reaction (without restriction enzyme) for each HCV genotype (Table 5). Predicted (in silico) negative or delayed reactions are shown in bold in Table 5. Obtained reactions agreed with predicted results: GT1 amplification reactions were completely inhibited by NheI-HF, BsrBI and Bsp681; GT2 amplification reaction was completely inhibited by NheI-HF; GT3 amplification was completely stopped by BsrBI, ApoI, BstEII, BstXI and Bsp681; GT4 amplification reaction were strongly inhibited by NheI-HF, BsrBI, ApoI, BsrGI, Bsp681. Presence of non-specific restriction enzymes also produced a delay in time to positive, but the extent of inhibition was less significant.

To amplify HCV viral RNA using a NASBA method on real-time PCR machine without restriction enzymes, the NASBA mix (NucliSens EasyQ Basic Kit v2, Biomerieux) was prepared as follows: 55 µL of Enzyme Diluent were added to an Enzyme Sphere and let sit for 20 min. The reagent mix was prepared in a clean tube containing 80 µL of Reagent Sphere Diluent, 12 µL NASBA Water, 16 µL KCl stock solution and the Reagent Sphere. After vortexing for 30 sec, 4.8 µL of vortexed NASBA forward primer (10 µM stock), 4.8 µL of vortexed NASBA reverse primer (10 µM stock) and 2.4 µL of vortexed NASBA probe (10 µM stock) were added to the reagent mix. The solution was split into 0.2 mL PCR tubes (10 µL each) and 4 µL of HCV RNA (sample) or nuclease-free water (non-template control) were loaded and incubated at 65° C. for 5 min Five µL of Enzyme solution (after gently flicking it to mix) and 1 µL of nuclease-free water were added to each PCR tube. The solution was split into 10 µL each and loaded into 2 wells on a Eco real-time PCR (Illumina, CA) plate and heated at 41° C. for 120 min.

To amplify HCV viral RNA using a NASBA method a on real-time PCR machine in the presence of restriction enzyme, the NASBA mix (NucliSens EasyQ Basic Kit v2, Biomerieux) was prepared as follows: 55 µL of Enzyme Diluent were added to an Enzyme Sphere and let sit for 20 min. The reagent mix was prepared in a clean tube containing 80 µL of Reagent Sphere Diluent, 12 µL NASBA Water, 16 µL KCl stock solution and the Reagent Sphere. After vortexing for 30 sec, 4.8 µL of vortexed NASBA forward primer (10 µM stock), 4.8 µL of vortexed NASBA reverse primer (10 µM stock) and 2.4 µL of vortexed NASBA probe (10 µM stock) were added to the reagent mix. The solution was split into 0.2 mL PCR tubes (10 µL each) and 4 µL of HCV RNA (sample) or nuclease-free water (non-template control) were loaded and incubated at 65° C. for 5 min. Five µL of Enzyme solution (after gently flicking it to mix) and 1 µL of diluted RE (20 fold diluted from purchased stock solution) were added to each PCR tube. The solution was split into 10 µL each and loaded into 2 wells on an Eco real-time PCR (Illumina, CA) plate and heated at 41° C. for 120 min.

Furthermore, a Nokia 808 Pureview cell phone was used to image microwells of a multivolume device (see, e.g., Feng Shen, Bing Sun, Jason E. Kreutz, Elena K. Davydova, Wenbin Du, Poluru L. Reddy, Loren J. Joseph, and Rustem F. Ismagilov, "Multiplexed Quantification of Nucleic Acids with Large Dynamic Range Using Multivolume Digital RT-PCR on a Rotational SlipChip Tested with HIV and Hepatitis C Viral Load," JACS 2011 133: 17705-17712) containing NASBA amplification product. This cell phone features a CMOS sensor with a Xenon flash. The Nokia 808 uses a 1/1.4-inch 41-megapixel sensor with a pixel size of 1.4 µm. Cell phone imaging was performed with a painted shoebox painted black inside. All images were taken using the standard cell phone camera application. The white balance was set to automatic, the ISO was set at 800, the exposure value was set at +2, the focus mode was set to "close-up," and the resolution was adjusted to 8 MP.

Example 7—Real-Time Bulk HCV Genotyping and Subtyping Using NASBA and Restriction Enzymes 14 restriction enzymes—AlwI, ApoI, BseYI, BsiEI, BsmAI, BsrBI, BsrGI, BsrI, BstEII, BstXI, BtsCI, HinfI, NheI and NruI—were selected for HCV genotyping (genotypes 1, 2, 3, 4, 5 and 6) and subtyping. The presence of target sequences for these restriction enzymes have been tested within the amplicon generated with the 5'UTR NASBA primers described in Example 6 and against a sequence alignment (n=1622) obtained from the Los Alamos HCV database. Results obtained by in silico analysis are shown in Table 6. In Table 6, the number of cutting sites per restriction enzyme against HCV sequences are represented as percentage, numbers in shaded boxes represent >70% coincidence. Included are Genotype 1 (GT1): subtype 1a (GT1a), subtype 1b (GT1b) and other GT1 subtypes (GT1nonAB); genotype 2 (GT2); Genotype 3 (GT3): subtype 3a (GT3a), subtype 3b (GT3b), subtype 3k (GT3k) and other GT3 subtypes (GT3nonABK); genotype 4 (GT4); genotype 5 (GT5); genotype 6 (GT6); N seq stands for the number of analyzed HCV sequences.

HCV NASBA primers and molecular beacon probes were also designed in CORE and NS5B regions for subtyping purposes; examples are shown in Table 7, Table 8, and Table 9. In Table 7, Table 8, and Table 9, bold type indicates the sequence of the bacteriophage T7 DNA-dependent RNA polymerase promoter, stem sequences are indicated with underlines, Y represents C or T, R represents A or G, and I represents inosine.

TABLE 6

Percentage of restriction enzyme cutting site per HCV genotype/subtype within 5'UTR NASBA amplicon.

| HCV Genotype/Subtype | N seq | AlwI | ApoI | BseYI | BsiEI | BsmAI | BsrBI | BsrGI | BsrI | BstEII | BstXI | BtsCI | HinfI | NheI | NruI |
|---|---|---|---|---|---|---|---|---|---|---|---|---|---|---|---|
| GT1a | 504 | 30.8 | 0.2 | 0.0 | 98.6 | 12.1 | 100.0 | 0.0 | 0.2 | 0.0 | 0.0 | 1.4 | 1.8 | 99.6 | 99.6 |
| GT1b | 365 | 88.5 | 0.0 | 0.0 | 94.5 | 96.4 | 99.5 | 0.0 | 0.5 | 0.0 | 0.3 | 4.4 | 1.1 | 99.7 | 99.5 |
| GT1nonAB | 29 | 48.3 | 17.2 | 0.0 | 93.1 | 27.6 | 100.0 | 3.4 | 0.0 | 0.0 | 0.0 | 6.9 | 20.7 | 100.0 | 100.0 |
| GT2 | 190 | 3.2 | 0.0 | 2.1 | 0.0 | 0.5 | 2.1 | 0.5 | 97.9 | 0.0 | 1.6 | 0.0 | 1.1 | 96.8 | 0.0 |
| GT3a | 134 | 3.7 | 97.0 | 96.3 | 1.5 | 2.2 | 99.3 | 0.0 | 0.7 | 94.0 | 96.3 | 3.0 | 97.8 | 3.0 | 99.3 |
| GT3b | 25 | 0.0 | 96.0 | 0.0 | 20.0 | 0.0 | 100.0 | 0.0 | 0.0 | 0.0 | 0.0 | 80.0 | 96.0 | 0.0 | 100.0 |
| GT3k | 23 | 0.0 | 100.0 | 0.0 | 0.0 | 91.3 | 100.0 | 0.0 | 0.0 | 0.0 | 0.0 | 0.0 | 100.0 | 100.0 | 95.7 |
| GT3nonABK | 21 | 9.5 | 81.0 | 14.3 | 14.3 | 19.0 | 100.0 | 0.0 | 0.0 | 85.7 | 14.3 | 0.0 | 100.0 | 14.3 | 100.0 |
| GT4 | 107 | 17.8 | 87.9 | 0.0 | 13.1 | 18.7 | 100.0 | 70.1 | 0.0 | 0.0 | 0.0 | 82.2 | 86.9 | 97.2 | 80.4 |
| GT5 | 52 | 1.9 | 1.9 | 0.0 | 17.3 | 98.1 | 100.0 | 0.0 | 0.0 | 0.0 | 0.0 | 82.7 | 5.8 | 100.0 | 100.0 |
| GT6 | 172 | 71.5 | 0.0 | 0.0 | 60.5 | 73.8 | 89.5 | 1.2 | 0.6 | 0.0 | 0.6 | 29.1 | 30.2 | 99.4 | 77.3 |

TABLE 7

NASBA primers and molecular beacon probes targeting NS5B.

| Name | Sequence 5'-3' |
|---|---|
| NS5B NASBA HCV forward primer_1 | ACGGAGGCTATGACCYGGTA (Seq ID No: 11) |
| NS5B NASBA HCV forward primer_2 | CTTCACGGAGGCTATGAC (Seq ID No: 12) |
| NS5B NASBA HCV reverse primer_1 | aattctaatacgactcactatagggagaaggAT GTTGCCTAGCCAGGARTT (Seq ID No: 13) |
| NS5B NASBA HCV reverse primer_2 | aattctaatacgactcactatagggagaaggAT IATGTTGCCTAGCCAGG (Seq ID No: 14) |
| NS5B NASBA HCV probe_1 | FAM <u>CCTGCAC</u>CAGAATACGACTTGGAGCTCAT AA<u>CGTGCAGG</u>BHQ1 (Seq ID No: 15) |
| NS5B NASBA HCV probe_2 | FAM <u>CCTGCAC</u>TAACATCATGITCCTCCAAY GTGTC<u>GTGCAGG</u>BHQ1 (Seq ID No: 16) |

TABLE 8

NASBA primers and molecular beacon probes targeting CORE.

| Name | Sequence 5'-3' |
|---|---|
| CORE NASBA HCV forward primer_1 | AGGACGTYAAGTTCCCGGG (Seq ID No: 17) |
| CORE NASBA HCV forward primer_2 | GATCGTTGGTGGAGTTTAC (Seq ID No: 18) |
| CORE NASBA HCV forward primer_3 | TCCTAAACCTCAAAGAAAAAC (Seq ID No: 19) |
| CORE NASBA HCV reverse primer_1 | aattctaatacgactcactatagggagaaggGC CAAGGRTACCCGGGCTG (Seq ID No: 20) |
| CORE NASBA HCV reverse primer_2 | aattctaatacgactcactatagggagaaggTC RTTGCCATAGAGGGGCC (Seq ID No: 21) |

TABLE 8-continued

NASBA primers and molecular beacon probes targeting CORE.

| Name | Sequence 5'-3' |
|---|---|
| CORE NASBA HCV reverse primer_3 | aattctaatacgactcactatagggagaaggGG AGCCATCCYGCCCACCC (Seq ID No: 22) |
| CORE NASBA HCV probe_1 | FAM CCTGCAAAGACTTCCGA GCGGTCRCAACCTGCAGGBHQ1 (Seq ID No: 23) |
| CORE NASBA HCV probe_2 | FAM CCTGCAAGGAAGACTTCC GAGCGGTCRCATGCAGGBHQ1 (Seq ID No: 24) |
| CORE NASBA HCV probe_3 | FAM CCTGCAAAGACTTCCGAGC GGTCRCAACCTCGTGCAGGBHQ1 (Seq ID No: 25) |
| CORE NASBA HCV probe_4 | FAM CCTGCAGGGTGTGCGCGCG ACGAGGAAGACTGCAGGBHQ1 (Seq ID No: 26) |

TABLE 9

NASBA primers and molecular beacon probes specific for HCV NS5B GT1A and GT1B.

| Name | Sequence 5'-3' | Amplicon size |
|---|---|---|
| P1_GT1A | AATTCTAATACGACTCACTATAGGGAAATCTACGG ATAGCAAGTTRGC (Seq ID No: 27) | 120 bp |
| P2_GT1A | CCAAAGGCAGAAGAAAGTCA (Seq ID No: 28) | |
| Beacon_GT1A | /FAM/CGCGATGGAGGTTAARGCRGCGGCGTATCGCG /BHQ1/ (Seq ID No: 29) | |
| P1_GT1B_set1 | AATTCTAATACGACTCACTATAGGGAAACTCCAAG TCGTATTCTGGTT (Seq ID No: 30) | 130 bp |
| P2_GT1B_set1 | CGACCTTGTCGTTATCTGTGA (Seq ID No: 31) | |
| Beacon_GT1B_set1 | /FAM/CGCGATTTCACGGAGGCTATGACTAGGTATCG CG/BHQ1/ (Seq ID No: 32) | |
| P1_GT1B_set2 | AATTCTAATACGACTCACTATAGGGAAATGAATGA TCTGAGGTAG (Seq ID No: 33) | 107 bp |
| P2_GT1B_set2 | TTCTTCTCCATCCTYMTA (Seq ID No: 34) | |
| Beacon_GT1B_set2 | /FAM/CGCGAT AARGCCCTRGAYTGYCAGATCTAATCGCG/BHQ1/ (Seq ID No: 35) | |
| P1_GT1B_set3 | AATTCTAATACGACTCACTATAGGGAAACACAACA TTGGTANATTGACT (Seq ID No: 36) | 119 bp |
| P2_GT1B_set3 | GGTGAAHRCCTGGAAAKCRAA (Seq ID No: 37) | |
| Beacon_GT1B_set3_1 | /FAM/CGCGATCACRGTCACYGAGARYGAYATCCGAT CGCG/BHQ1/ (Seq ID No: 38) | |
| Beacon_GT1B_set3_2 | /FAM/CGCGATCGACACCCGYTGYTTYGACTCAAGAT CGCG/BHQ1/ (Seq ID No: 39) | |
| P1_GT1B_set4 | AATTCTAATACGACTCACTATAGGGAAAAAGTGG YTCAATGGAGTA (Seq ID No: 40) | 110 bp |

TABLE 9-continued

NASBA primers and molecular beacon probes specific
for HCV_NS5B_GT1A and GT1B.

| Name | Sequence 5'-3' | Amplicon size |
|---|---|---|
| P2_GT1B_set4 | CAAGGATGATYCTGATGAC (Seq ID No: 41) | |
| Beacon_GT1B_set4 | /FAM/CGCGATCCCTYCTAGCNCAGGARCAACTGATCGCG/BHQ1/ (Seq ID No: 42) | |
| P1_GT1B_set5 | AATTCTAATACGACTCACTATAGGGAAAGCTAGAA GGATGGAGAAR (Seq ID No: 43) | 113 bp |
| P2_GT1B_set5 | GARACAGCTAGACACACT (Seq ID No: 44) | |
| Becon_GT1B_set5 | /FAM/GCGATCGGCTAGGCAACATCATCATGATCGC/BHQ1/ (Seq ID No: 45) | |

Example 8—Quantitative Nucleic Acid Detection by Loop-Mediated Isothermal Amplification (LAMP)

A Reverse-Transcription Loop mediated amplification (RT LAMP) assay was conducted for quantitative isothermal detection of nucleic acids such as detection of Hepatitis C viral (HCV) RNA. The test comprises at least one nucleic acid primer set capable of detecting Hepatitis C viral (HCV) RNA in a LAMP based molecular test, the primer set being chosen from the primer sets listed in Table 10. Each assay consists of a primer set including one pair of forward (FIP) and reverse (BIP) inner primers, forward (F3) and reverse (B3) outer primers. The assay can also include loop forward (LF) and/or loop back (LB) primers to accelerate the reaction. HCV genotypes 1, 2, 3, 4, 5, 6, and 7 can be detected using the assay. The assay is applicable for studying a number of diseases, including but not limited to accurate HCV quantification using a digital format (i.e., confining single molecules into compartments and amplifying them separately) on a SlipChip device.

Figure 17:
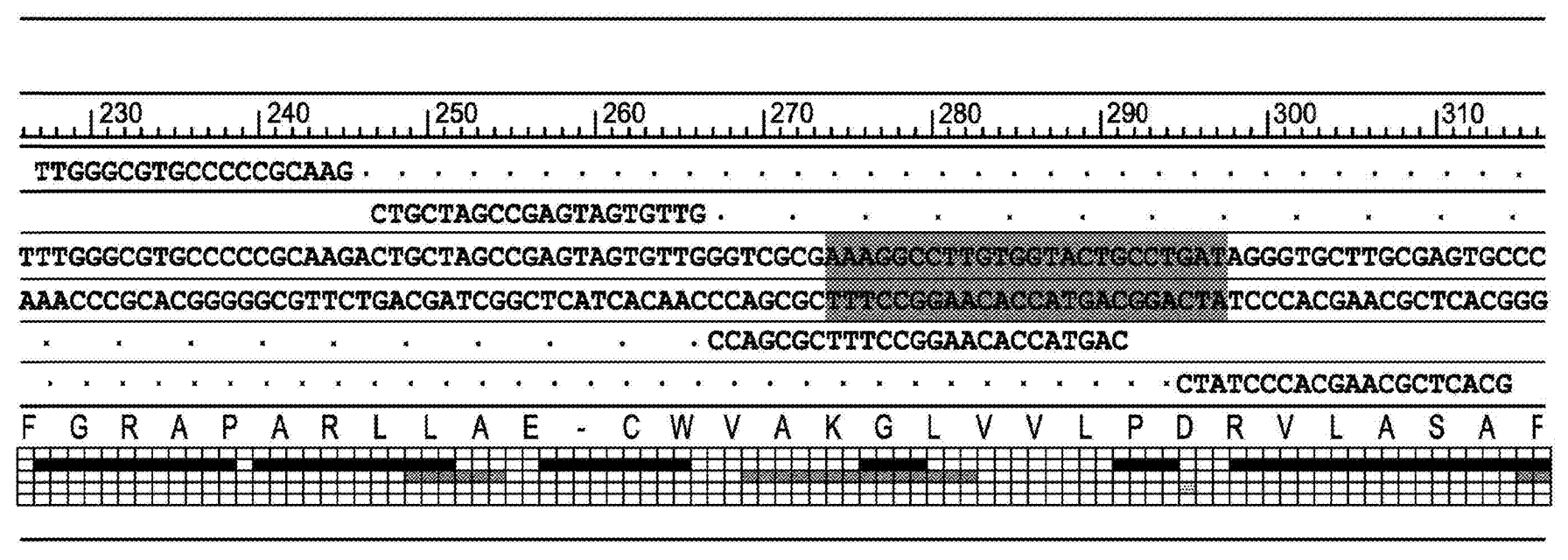
Figure 18:
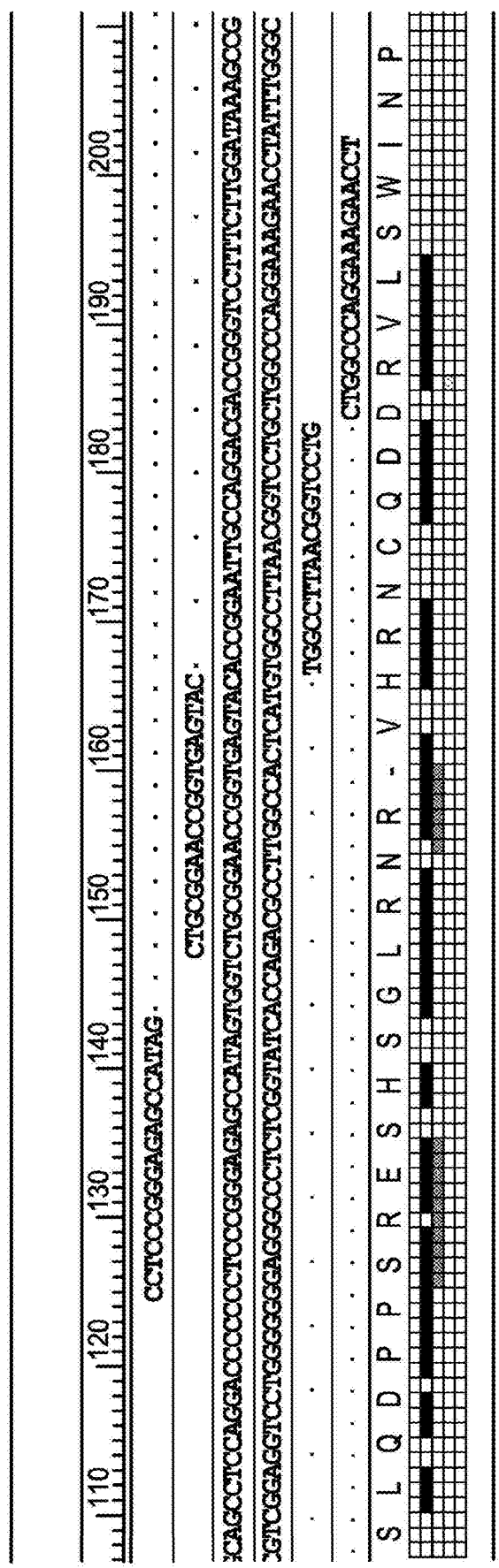
FIG. 18 shows an exemplary illustration of F side primer and primer part sequence variants (Seq ID No: 43, Seq ID No: 44, Seq ID No: 73 and Seq ID No: 74) aligned to a typical HCV sequence (Seq ID No: 98, Seq ID No: 99) shown together with amino acid sequences encoded thereby (Seq ID No: 100, and Seq ID No: 101).

Primers for LAMP were designed to achieve improvements including a higher melting temperature for reverse-transcription primers, weakened loopF primer annealing to improve efficiency and delaying time to product signal, and positioning important-to-anneal fast primer parts (B1c and F1c) to be complementary to the secondary structures loop in RNA template to improve detection efficiency. HCV, like HIV, has a large variety of genotypes and mutates rapidly due to the error-prone nature of the reverse transcriptase. As a result, it is beneficial for a quantification assay to be able to detect all the genotypes or genotypes with high prevalence. To make the primer set general, the 3' halves of the B3, F3, B2, F2 primers sequences and the 5' halves of the B1c and F1c primers sequences were positioned to the most conserved positions in the all HCV known sequences alignment. The primers were further made to be universal and suitable to a widest known variety of HCV isolates, and are shown in Table 10, Table 11, and Table 12. FIG. 17 shows an illustration of one of the disclosed B side primers and primer parts sequences variant aligned to one of the typical HCV sequences. FIG. 18 shows an illustration of one of the disclosed F side primers and primer parts sequences variant aligned to one of the typical HCV sequences.

TABLE 10

A summary of basic and universal (containing Inosine as a general nucleic acid base pairer) primers developed for efficient and specific detection of, for example, HCV RNA via RT-LAMP.

| Primer | F3 | FIP | loopF (LF) |
|---|---|---|---|
| basic | CCTCCCGGGA GAGCCATAG (Seq ID No: 46) | TCCAAGAAAGGACCCGGTCTTTTTCT GCGGAACCGGTGAGTAC (Seq ID No: 47) | GTCCTGGCAAT TCCGGT (Seq ID No: 48) |
| universal | CCTCCCGGGA GAGCCATAG (Seq ID No: 46) | TCCAAGAAAGGACCCIGTCTTTTTCT GCGGAACCGGTGAGTAC (Seq ID No: 49) | TTICCGGIAATT CCGGT (Seq ID No: 50) |

| Primer | B3 | BIP | loopB (LB) |
|---|---|---|---|
| basic | GCACTCGCAA GCACCCTATC (Seq ID No: 51) | TTGGGCGTGCCCCCGCAAGTTTTTCA GTACCACAAGGCCTTTCGCGACC (Seq ID No: 52) | CTGCTAGCCGA GTAGTGTTG (Seq ID No: 53) |

TABLE 10-continued

A summary of basic and universal (containing Inosine as a general nucleic acid base pairer) primers developed for efficient and specific detection of, for example, HCV RNA via RT-LAMP.

| | | | |
|---|---|---|---|
| universal | GCACTCGCAA GCACCITATC (Seq ID No: 54) | TTGGGCGTGCCCCCGCIAGATTTTTC AGTACCACAAGGCCITTCGCIACC (Seq ID No: 55) | CTGCTAGCCGA GTAGIGTTG (Seq ID No: 56,) |

TABLE 11

A summary of additional FIP primers, designed in this case to compensate for a known HCV isolates of different subtypes/genotypes, via RT-LAMP detection.

| genotype | FIP variant |
|---|---|
| 1 | TCCAAGAAAGGICCCIGTCTTTTT CTGCGGAACCGGTGAGTAC (Seq ID No: 57) |
| 2 | CCCAAGAAAGGICCCIGTCTTTTT CTGCGGAACCGGTGAGTAC (Seq ID No: 58) |
| 3 | TCCAATGGAAAGGICCCIGTCTTTTT CTGCGGAACCGGTGAGTAC (Seq ID No: 59) |
| Some 4 and 6 | TCCAAGAAAGGICCCIGTCTTTTT CTGCGGAACCGGTGAGTTC (Seq ID No: 60) |
| Some 1 | TCCAIGAAAGGACCCGGTCTTTTT CTGCGGAACCGGTGAGTAC (Seq ID No: 61) |

TABLE 12

A summary of universal loopF (LF) primers, designed to compensate for known subtypes/genotypes sequence variations.

| Template consensus | genotype | LF primer |
|---|---|---|
| ACCGNAATTGCCAGGAC (Seq ID No: 62) | 1 | GTCCTGGCAATTICGGT (Seq ID No: 63) |
| ACCGGAATTNCCGGNAA (Seq ID No: 64) | 2 and 1 | TTICCGGIAATTCCGGT (Seq ID No: 50) |
| ACCGGAATNGCNGGGNN (Seq ID No: 65) | 3 and 4 | IICCCIGCIATTCCGGT (Seq ID No: 66) |
| ACCGGAATNGCNGGGGT (Seq ID No: 67) | | AICCCIGCIATTCCGGT (Seq ID No: 68) |

Back side primers can comprise the following:

BIP:
(Seq ID No: 69)
5'TTGGGCGTGCCCCCGCAAGttttCAGTACCACAAGGCCTTTCGCGACC 3'

BIP primer comprises of the B2 and B1c parts, which may be connected directly, or through any linker sequence, including but not limited to tttt.

B2 part of BIP:
(Seq ID No: 70)
the core sequence is 5'-CAGTACCACAAGGCCTTTCGCGACC-3'

As a B2 part of BIP primer, an oligonucleotide is used comprising at least 5 consecutive nucleotides of the nucleotide sequence CAGTACCACAAGGCCTTTCGCGACC (Seq ID No: 70).

B1c part of BIP:
(Seq ID No: 71)
the core sequence is 5'-TTGGGCGTGCCCCCGCAAG-3'

Variations of the B1c part of BIP incorporation of inosin, LNA or BNA modified, and other modified bases.

(Seq ID No: 72)
loopB: 5' CTGCTAGCCGAGTAGTGTTG 3'

A loopB element may or may not be present in the amplification reaction. Variations of loopB include incorporation of inosine, LNA or BNA modified, and other modified bases. As a loopB primer an oligonucleotide can be used comprising at least 5 consecutive nucleotides of the nucleotide sequence CTGCTAGCCGAGTAGTGTTG (Seq ID No: 72).

(Seq ID No: 51)
B3: 5'-GCACTCGCAAGCACCCTATC-3'

B3 primer may or may not be present in 1-step RT-LAMP reactions. As a B3 primer an oligonucleotide can be used comprising at least 5 consecutive nucleotides of the nucleotide sequence GCACTCGCAAGCACCCTATC (Seq ID No: 51).

Forward side primers can comprise the following:

(Seq ID No: 46)
F3 primer: 5'-CCTCCCGGGAGAGCCATAG-3'

As a F3 primer an oligonucleotide can be used comprising at least 5 consecutive nucleotides of the nucleotide sequence CCTCCCGGGAGAGCCATAG (Seq ID No: 46).

FIP primer:
(Seq ID No: 47)
5'-TCCAAGAAAGGACCCGGTCTTTTTCTGCGGAACCGGTGAGTAC-3'

Variations on the FIP primer can include universal variants with inosines, or any other nucleotide bases instead of them are as follows:

(Seq ID No: 47)
5'-TCCAAGAAAGGACCCGGTC TTTTT CTGCGGAACCGGTGAGTAC-3'

(Seq ID No: 57)
5'-TCCAAGAAAGGICCCIGTC TTTTT CTGCGGAACCGGTGAGTAC-3' (#1)

(Seq ID No: 58)
5'-CCCAAGAAAGGICCCIGTC TTTTT CTGCGGAACCGGTGAGTAC-3' (#2)

(Seq ID No: 59)
5'-TCCAATGGAAAGGICCCIGTC TTTTT CTGCGGAACCGGTGAGTAC-3' (#3)

(Seq ID No: 60)
5'-TCCAAGAAAGGICCCIGTC TTTTT CTGCGGAACCGGTGAGTTC-3' (#4 for some #4,6)

(Seq ID No: 61)
5'-TCCAI-GAAAGGACCCGGTC TTTTT CTGCGGAACCGGTGAGTAC-3' (#5 for some #1)

The FIP primer comprises of the F2 and F1c parts, which may be connected directly, or through any linker sequence, including but not limited to ttttt.

F2 part of FIP:
(Seq ID No: 73)
the core sequence is 5'-CTGCGGAACCGGTGAGTAC-3',

Variations of F2 can include incorporation of inosin, LNA or BNA modified, and other modified bases. As a F2 part of FIP primer an oligonucleotide can be used comprising at least 5 consecutive nucleotides of the nucleotide sequence 5' CTGCGGAACCGGTGAGTAC 3' (Seq ID No: 73).

F1c part of FIP:
(Seq ID No: 74)
the core sequence is 5'-TCCAAGAAAGGACCCGGTC-3', As a F1c part of FIP primer an oligonucleotide can be used comprising at least 5 consecutive nucleotides of the nucleotide sequence TCCAAGAAAGGACCCGGTC (Seq ID No: 74) Loop F primers (LF): LF may or may not be used in the amplification reaction. Some of LF variants used are:

(Seq ID No: 48)
5'GTCCTGGCAATTCCGGT 3'

(Seq ID No: 75)
5'TCGTCCTGGCAATTCCG 3'

(Seq ID No: 48)
5' GTCCTGGCAATTCCGGT 3'

Variations of LF can include but are not limited to incorporation of inosine, LNA or BNA modified, and other modified bases. As a LF primer an oligonucleotide can be used comprising at least 5 consecutive nucleotides of the nucleotide sequence TCGTCCTGGCAATTCCG (Seq ID No: 75).

In addition, variations of all the mentioned primers and primer parts can include but are not limited to incorporation of inosine, LNA or BNA modified, and other modified bases; changing up to 20% of the bases for the other nucleotides, including inosine, dUTPs, LNA or BNA modified bases, RNA bases, abased nucleotides or any nucleotide analogs; shifting or shortening the primer or primer part up to 7 bases counting from either it's 5' or 3' ends, or both; and simple elongating the primer. The primers were designed based on HCV genotype 1a, but after modification it can be used to detect all the major genotypes circulating in the US as well as other nucleic acids.

Figure 19:
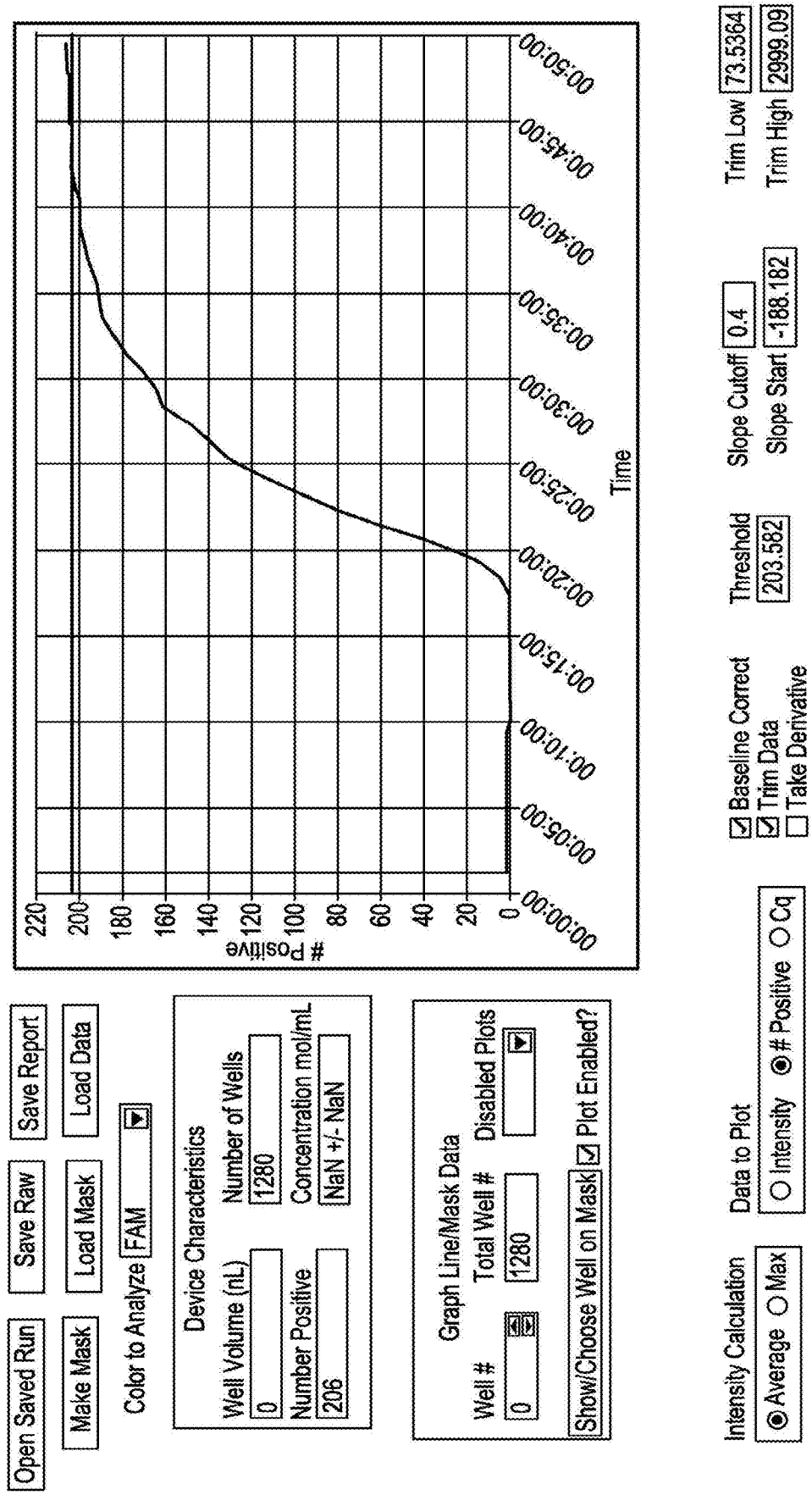
FIG. 19 shows exemplary results for the number of positive wells versus time from a one-step dRT-LAMP HCV RNA detection assay.
Figure 20:
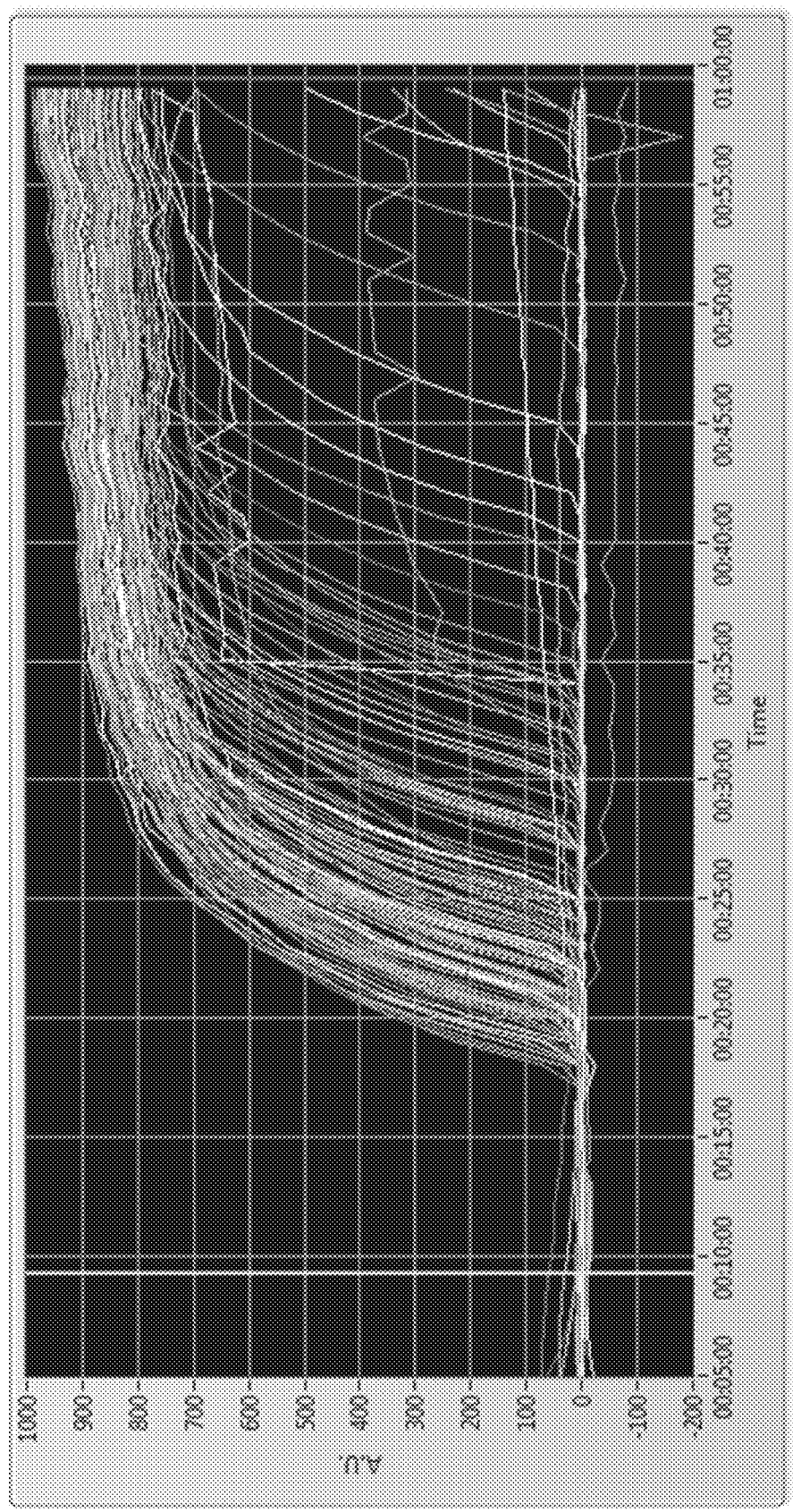
FIG. 20 shows exemplary results for the signal from each well versus time from a one-step dRT-LAMP HCV RNA detection assay.
Figure 21:
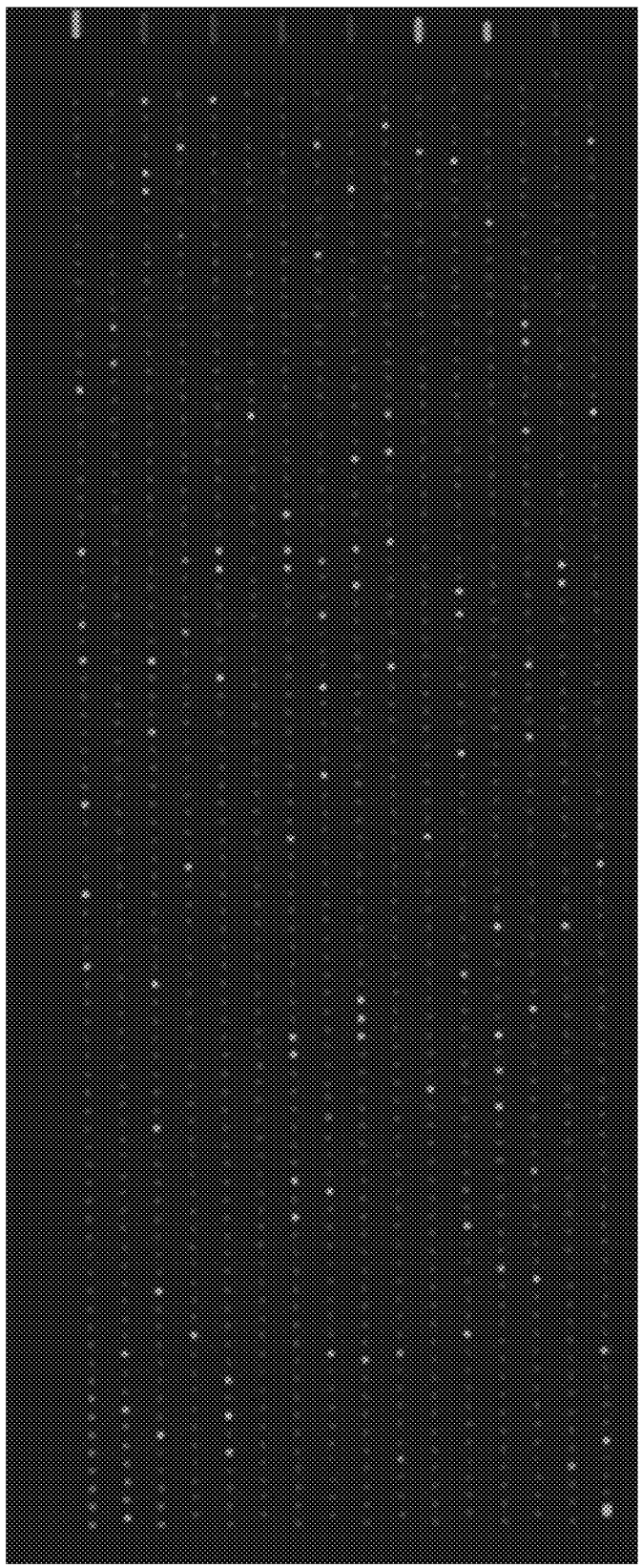
FIG. 21 shows an exemplary image of a SlipChip device with results from a one-step dRT-LAMP HCV RNA detection assay.
Figure 22A:
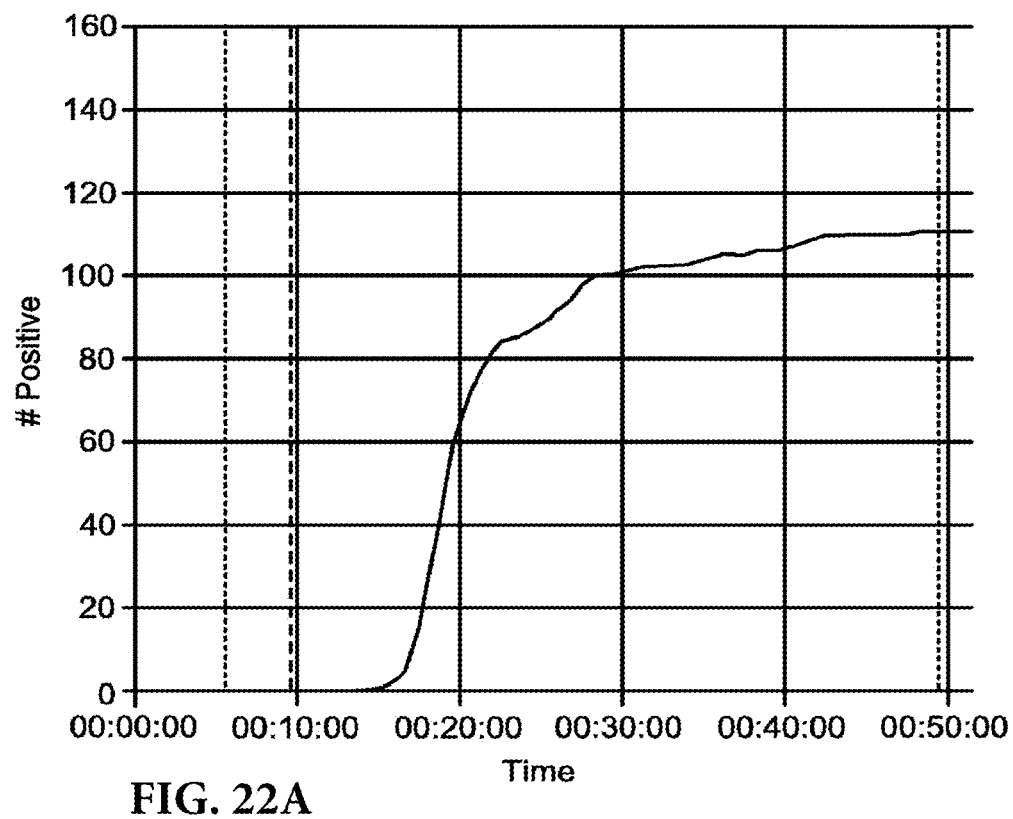
FIG. 22A shows exemplary results for the number of positive wells versus time from a one-step dRT-LAMP HCV RNA detection assay.
Figure 22B:
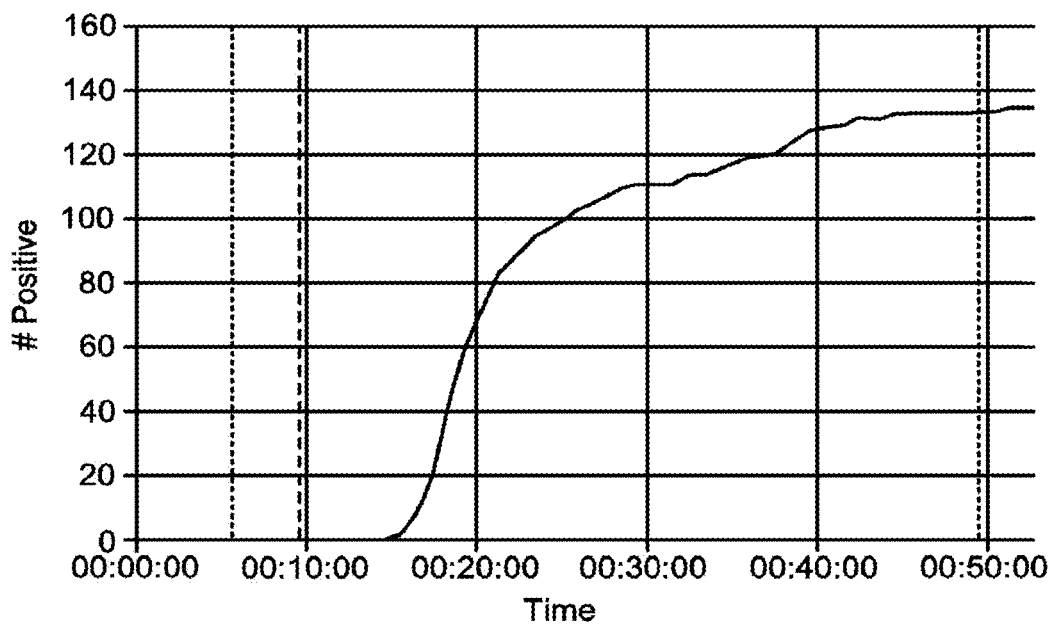
FIG. 22B shows exemplary results for the number of positive wells versus time from a one-step dRT-LAMP HCV RNA detection assay.

LAMP was conducted in a digital format (e.g., confining single molecules into compartments and amplifying them separately) on a SlipChip device comprising 1280 wells. FIG. 19 shows results for the number of positive wells versus time, from one step dRT-LAMP HCV RNA detection with real-time tracking of the 1280 wells' intensity over time. The reaction was done on standard fresh HCV RNA quantified with dRT-PCR, in a presence of total RNA extracted from human blood plasma, in 1× final concentration in reaction mixture. ~250 HCV RNA were loaded, copies quantified with RT-PCR. FIG. 20 shows results for the signal from each well versus time, from one step dRT-LAMP HCV RNA detection with real-time tracking of the 1280 wells' intensity over time. At 50 minutes, 128 positive counts had been observed out of an estimated total 133+/−11 viral copies loaded and quantified with RT-PCR. FIG. 21 shows an image of a SlipChip device with results from one step dRT-LAMP HCV RNA detection. At 50 minutes, 99 positive counts are visible out of an estimated total 133+/−11 viral copies loaded, quantified with RT-PCR. FIG. 22 shows results for the number of positive wells versus time, from one step dRT-LAMP HCV RNA detection with real-time tracking of the 1280 wells' intensity over time. Reaction was done on standard fresh HCV RNA quantified with dRT-PCR, ~133 HCV RNA copies were loaded (+/−~11 copies). At 50 minutes, 111 copies were detected in a first experiment (FIG. 22A) 111 and 134 copies were detected in a second experiment (FIG. 22B).

Example 9—Real-Time Digital RT-LAMP/Restriction Enzyme (RT-LAMP/RE) Assay for HCV Genotyping Real-time digital RT-LAMP/restriction enzyme (RT-LAMP/RE) experiments were performed with HCV Genotype 1 (GT1) RNA using BsrBI as the restriction enzyme. RT-LAMP primers are shown in Table 13. HCV GT1 isolate was obtained commercially and sequenced after RNA purification to confirm the genotype assignment; sequencing results for HCV RNA purified from the isolates is shown in Table 14.

TABLE 13

Sequence of primers used in RT-LAMP.

| primer | sequence (5'-3') |
|---|---|
| F3 | CCTCCCGGGAGAGCCATAG (Seq ID No: 46) |
| HP | TCCAAGAAAGGACCCIGTCTTTTTCTGCGGAACCGGTGAGTAC (Seq ID No: 49) |
| LF | TTICCGGIAATTCCGGT (Seq ID No: 50) |
| B3 | GCACTCGCAAGCACCITATC (Seq ID No: 54) |

TABLE 13-continued

Sequence of primers used in RT-LAMP.

primer sequence (5'-3')

BIP     TTGGGCGTGCCCCCGCIAGATTTTTCAGTACCACAAGGCCITT
        CGCIACC
        (Seq ID No: 55)

LB      CTGCTAGCCGAGTAGIGTTG
        (Seq ID No: 56)

TABLE 14

Sequencing results for HCV RNA
purified from purchased isolates.

Genotype 1  TCGTGCAGCCTCCAGGACCCCCCCTCTCGGGAGAGCCATAGTGGTCTGC
            GGAACCGGTGAGTACACCGGAATTGCCAGGACGACCGGGTCCTTTCTT
            GGATCAACCCGCTCAATGCCTGGAGATTTGGGCGTGCCCCCGCGAGACT
            GCTAGCCGAGTAGTGTTGGGTCGCGAAAGGCCTTGTGGTACTGCCTGAT
            AGGGTGCTTGCGAGTGCCTCGGGAGGT
            (Seq ID No: 76)

Genotype 2  TCGTACAGCCTCCAGGCCCCCCCCTCCCGGGAGAGCCATAGTGGTCTGC
            GGAACCGGTGAGTACACCGGAATTGCCGGGAAGACTGGGTCCTTTCTT
            GGATAAACCCACTCTATGCCCGGCCATTTGGGCGTGCCCCCGCAAGACT
            GCTAGCCGAGTAGCGTTGGGTTGCGAAAGGCCTTGTGGTACTGCCTGAT
            AGGGTGCTTGCGAGTGCCCCGGGAGGT
            (Seq ID No: 77)

Genotype 3  TCGTGCAGCCTCCAGGATCCCCCCTCCCGGGAGAGCCATAGTGGTCTGC
            GGAACCGGTGAGTACACCGGAATCGCTGGGGTGACCGGGTCCTTTCTTG
            GAGCAACCCGCTCAATACCCAGAAATTTGGGCGTGCCCCCGCGAGATC
            ACTAGCCGAGTAGTGTTGGGTCGCGAAAGGCCTTGTGGTACTGCCTGAT
            AGGGTGCTTGCGAGTGCCCCGGGAGGT
            (Seq ID No: 78)

Genotype 4  TTGTACAGCCTCCAGGACCCCCCCTCCCGGGAGAGCCATAGTGGTCTGC
            GGAACCGGTGAGTACACCGGAATCGCCGGGATGACCGGGTCCTTTCTT
            GGATAAACCCGCTCAATGCCCGGAAATTTGGGCGTGCCCCCGCAAGAC
            TGCTAGCCGAGTAGTGTTGGGTCGCGAAAGGCCTTGTGGTACTGCCTGA
            TAGGGTGCTTGCGAGTGCCCCGGGAGGT
            (Seq ID No: 79)

Figure 23:
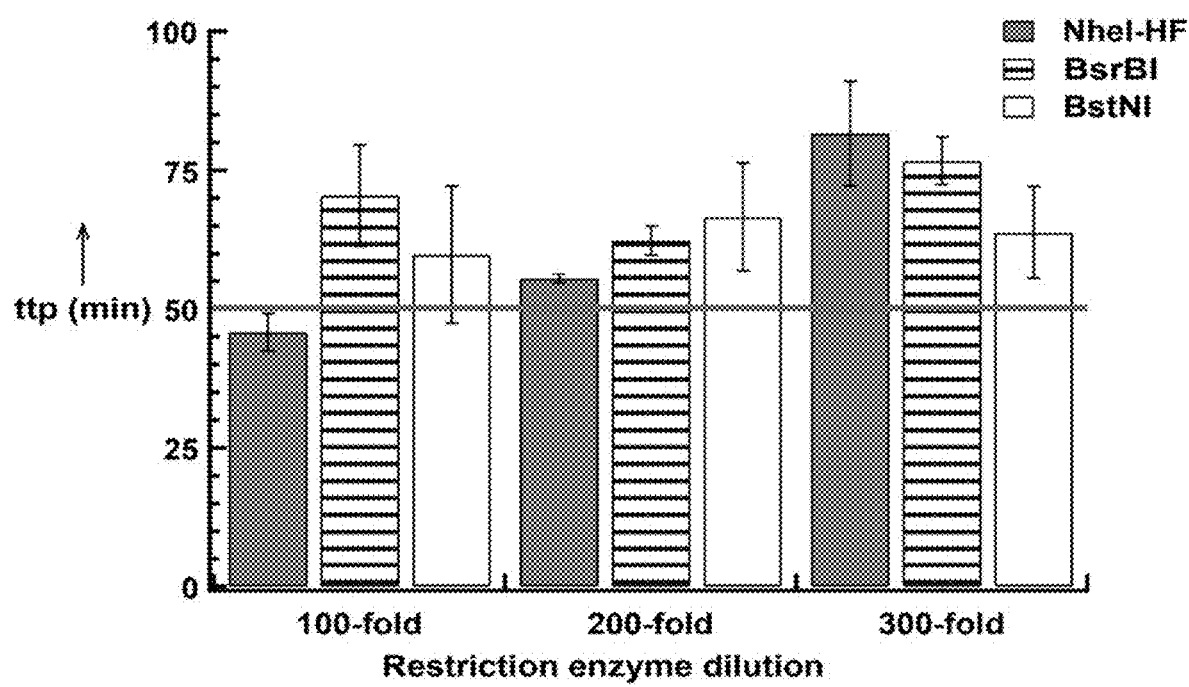
FIG. 23 shows exemplary results comparing time to positive for different restriction enzymes at different dilutions.

BsrBI cuts dsDNA at sequences CCGCTC, and this sequence exists in the RT-LAMP amplicon of GT1 RNA. With negative control experiments, the highest possible BsrBI concentration that did not trigger ab initio DNA synthesis within the time of interest under reaction conditions was identified, as shown in FIG. 23. The concentration was determined by performing a restriction enzyme dilution experiment in the presence of all RT-LAMP components except HCV RNA and choosing the concentration for which ab initio synthesis was not observed within 50 min. Columns represent time to positive (ttp) caused by ab initio DNA synthesis and error bars stand for standard deviation. RT-LAMP reactions were performed in the absence of HCV RNA and in the presence of three different dilutions (100-fold, 200-fold and 300-fold) of NheI (grey), BsrBI (striped), and BstNI (white). Horizontal solid line shows the ttp threshold set for analysis (50 min). In the experiments reported in this paper, 200-fold RE dilution was used because 100-fold dilution was not enough to remove the influence of ab initio DNA synthesis within 50 min.

Figure 25A:
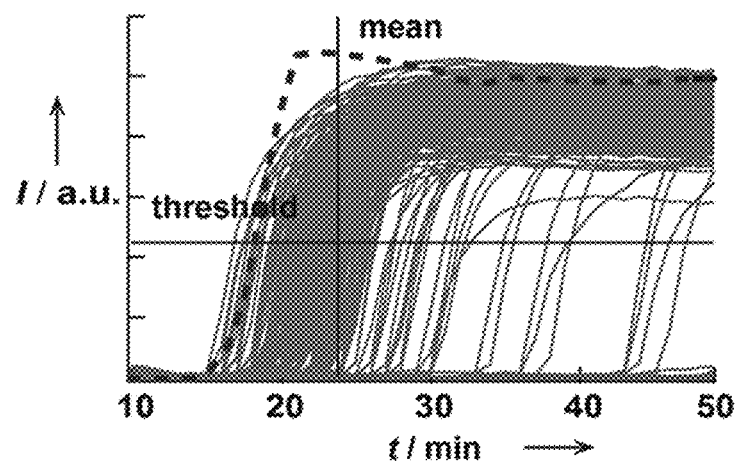
FIG. 25A shows exemplary results for 1280 fluorescence traces for the RT-LAMP amplification process of all the wells on a SlipChip device (solid lines) and normalized averaged fluorescence curve in bulk (dashed line) in the absence of restriction enzymes.
Figure 25B:
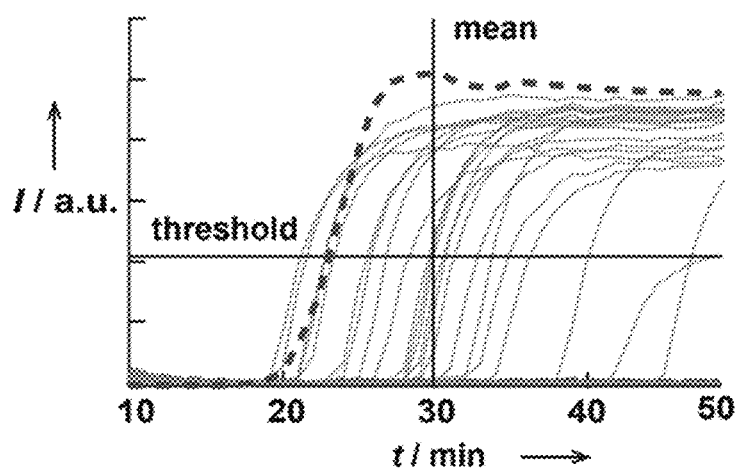
FIG. 25B shows exemplary results for traces for a digital assay (solid lines) and for a bulk assay (dashed line) in the presence of restriction enzyme BsrBI.
Figure 25C:
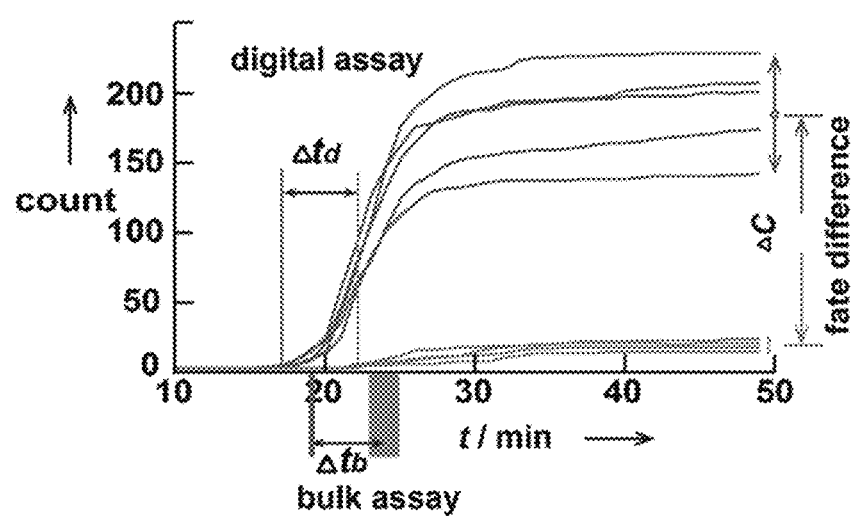
FIG. 25C shows exemplary results for the change of cumulative counts over time for wells exceeding the threshold in FIG. 25A, (upper five lines), and FIG. 25B (lower lines).
Figure 26:
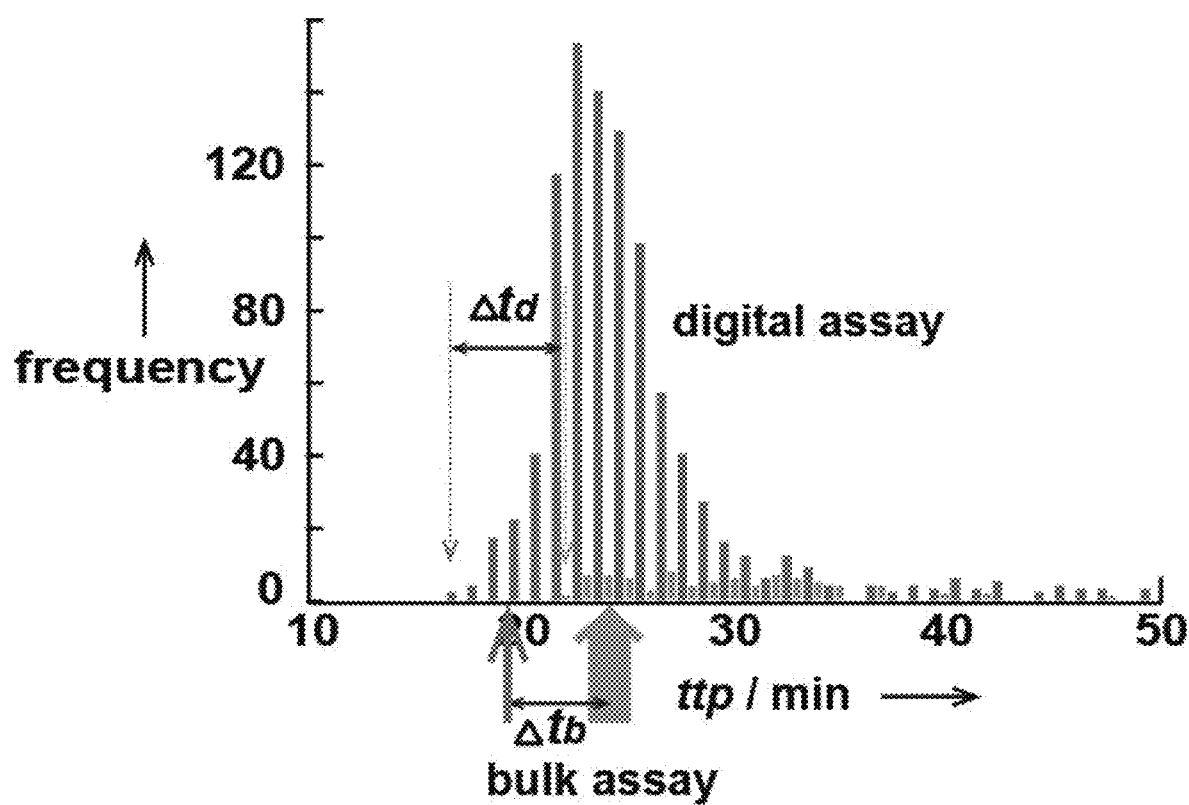
FIG. 26 shows an exemplary histogram of real-time, single-molecule digital RT-LAMP/RE experiments for HCV GT1 RNA.

A SlipChip microfluidic device was used to compartmentalize the reaction mixture, as shown in FIG. 24. Schematic drawings show the layout of top and bottom piece of the entire device on the right and a zoomed-in region (black box) on the left (FIG. 24A), the relative position of two pieces when they are aligned to allow the loading of solution through the channel (FIG. 24B), and the relative position of two pieces when they are slipped to separate droplets from one another and form compartments (FIG. 24C). The progress of amplification was monitored for each single molecule using a CCD-based imaging system, with results shown in FIG. 25. FIG. 25A shows 1280 fluorescence traces for the RT-LAMP amplification process of all the wells on a SlipChip device (solid lines) and normalized averaged fluorescence curve in bulk (dashed line) in the absence of restriction enzymes. FIG. 25B shows traces for digital (solid lines) and for bulk (dashed line) in the presence of restriction enzyme BsrBI. Horizontal solid lines indicate the threshold levels to consider a well positive. Vertical solid lines show the mean of the time-to-positive distribution. FIG. 25C shows the change of cumulative counts over time for wells exceeding the threshold in FIG. 25A, (upper five lines), and FIG. 25B (lower lines). The two bars below the x-axis show time-to-positive for real-time bulk experiments, the widths of which stand for standard deviation for the bulk assay (n=5) (left line for FIG. 25A results, right line from FIG. 25B results). Even in the amplification reaction in the absence of the restriction enzyme, significant heterogeneity was observed among rates of amplification of different molecules (FIG. 25A). Addition of BsrBI did not abolish this heterogeneity (FIG. 25B). On average, even though the rates of the reactions decreased upon addition of BsrBI, the shift in reaction times (approximately 5 min, for the first well that turned positive) was small relative to the width of the distribution of the reaction times (over 30 min). On the other hand, the fate of single-molecule amplification did change significantly upon addition of BsrBI: ~10-fold fewer molecules gave rise to successful amplification (with a p-value of 0.00033), indicating that in digital RT-LAMP, BsrBI affects fate more than it affects rate. FIG. 26 shows a histogram of real-time, single-molecule digital RT-LAMP/RE experiments for HCV GT1 RNA; the graph shows the change of rate for positive wells in the absence of restriction enzyme and in the presence of BsrBI; the two bars below the x-axis show time-to-positive for real-time bulk experiments, the widths of which stand for standard deviation for the bulk assay (n=5) (left arrow for absence of restriction enzyme, right arrow for presence of restriction enzyme).

Figures 27A, 27B:
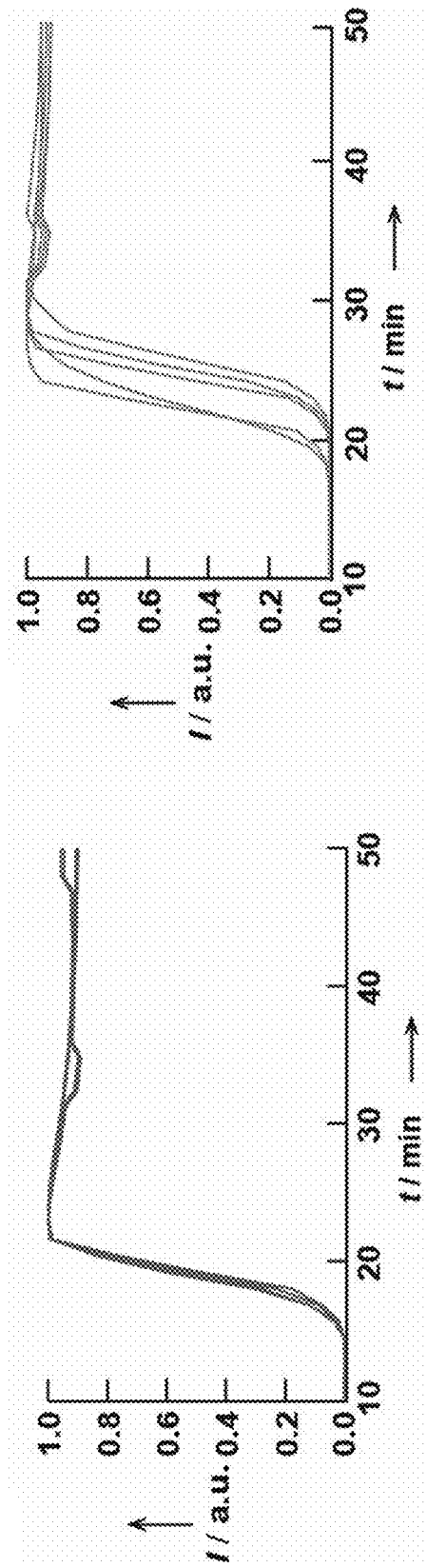
FIG. 27A shows exemplary real-time RT-LAMP curves for GT1 in the absence of restriction enzyme (positive control).
FIG. 27B shows exemplary real-time RT-LAMP curves for GT1 in the presence of BsrBI.

The same competition experiments were performed in a bulk real-time format using an RNA concentration of ~3.3× 105 copies/mL (estimated based on digital RT-LAMP results), equivalent to the concentration of a single molecule in a 3 nL well. Without BsrBI, the reaction in this bulk experiment was approximately 5 min faster than the mean amplification time in the corresponding digital experiment (FIG. 25A); it was closer to the time of the amplification of the first molecule (approximately 2 min slower) (FIG. 25C). Upon addition of BsrBI, the bulk reaction showed increased variance and slowed down by $\Delta tb=4.9\pm1.9$ min (FIG. 25C); this delay was similar to the delay of the time-to-positive of the first molecule in the digital format, $\Delta td=4.2\pm1.1$ min (FIG. 25C). These data suggest that once exponential amplification of some molecules takes off, this process dominates the reaction mixture and is not affected by the amplification of the molecules that amplify later in the digital format—the bulk reaction has ended by then. In other words, the bulk experiment is dominated by the rate of amplification of the earliest molecules, and not sensitive to the fate of the rest of the molecules. FIG. 27A shows real-time RT-LAMP curves for GT1 in the absence of restriction enzyme (positive control); FIG. 27B shows real-time RT-LAMP curves for GT1 in the presence of BsrBI.

Figure 28A:
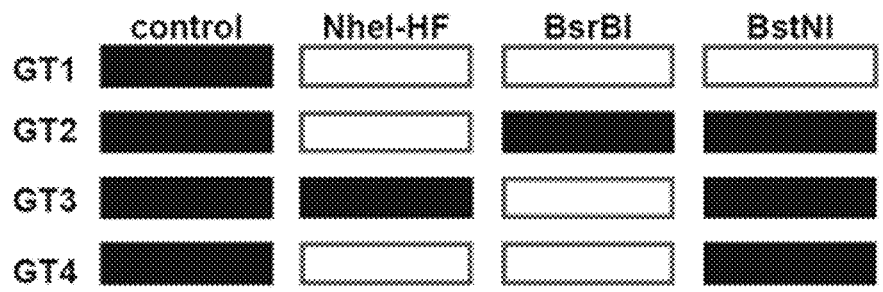
FIG. 28A shows exemplary predicted results for an amplification reaction assay with different restriction enzymes and genotypes.
Figure 28B:
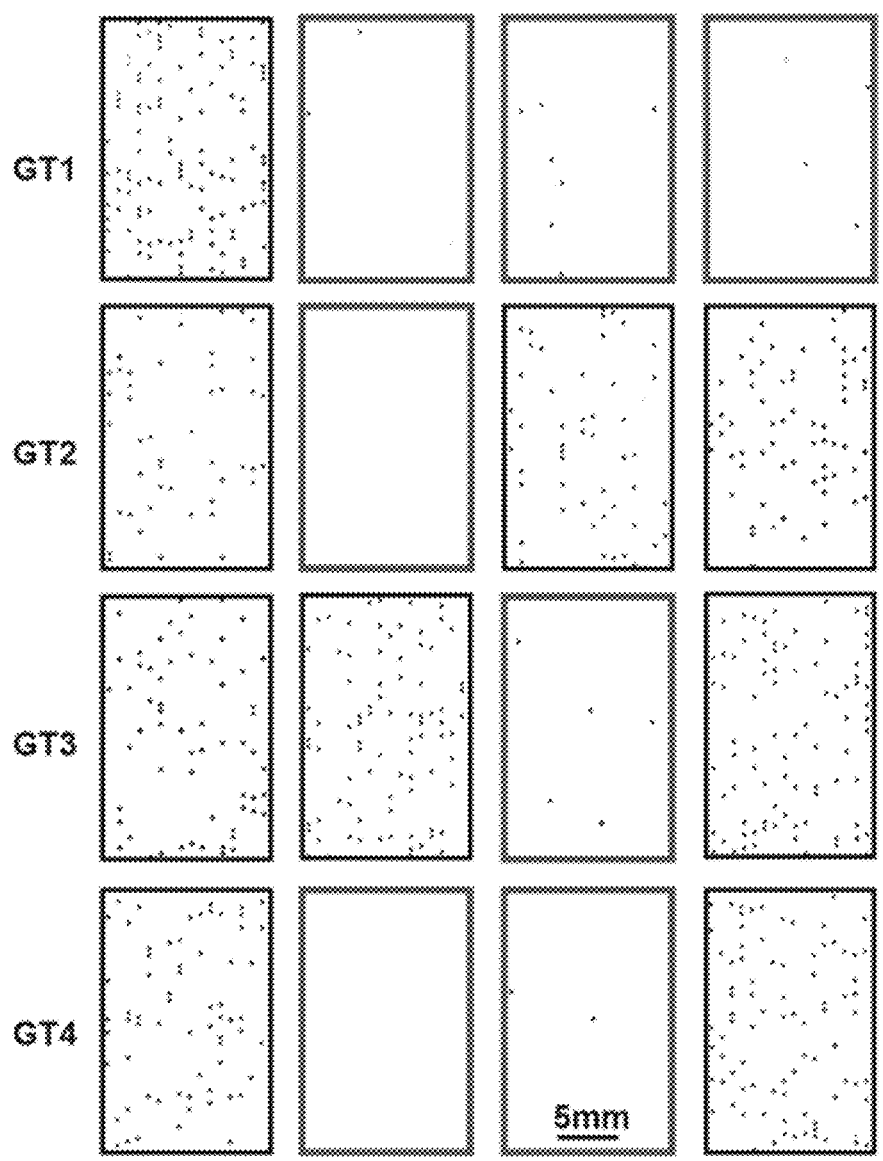
FIG. 28B shows exemplary experimental results on a device for an amplification reaction assay with different restriction enzymes and genotypes.
Figures 29A, 29B:
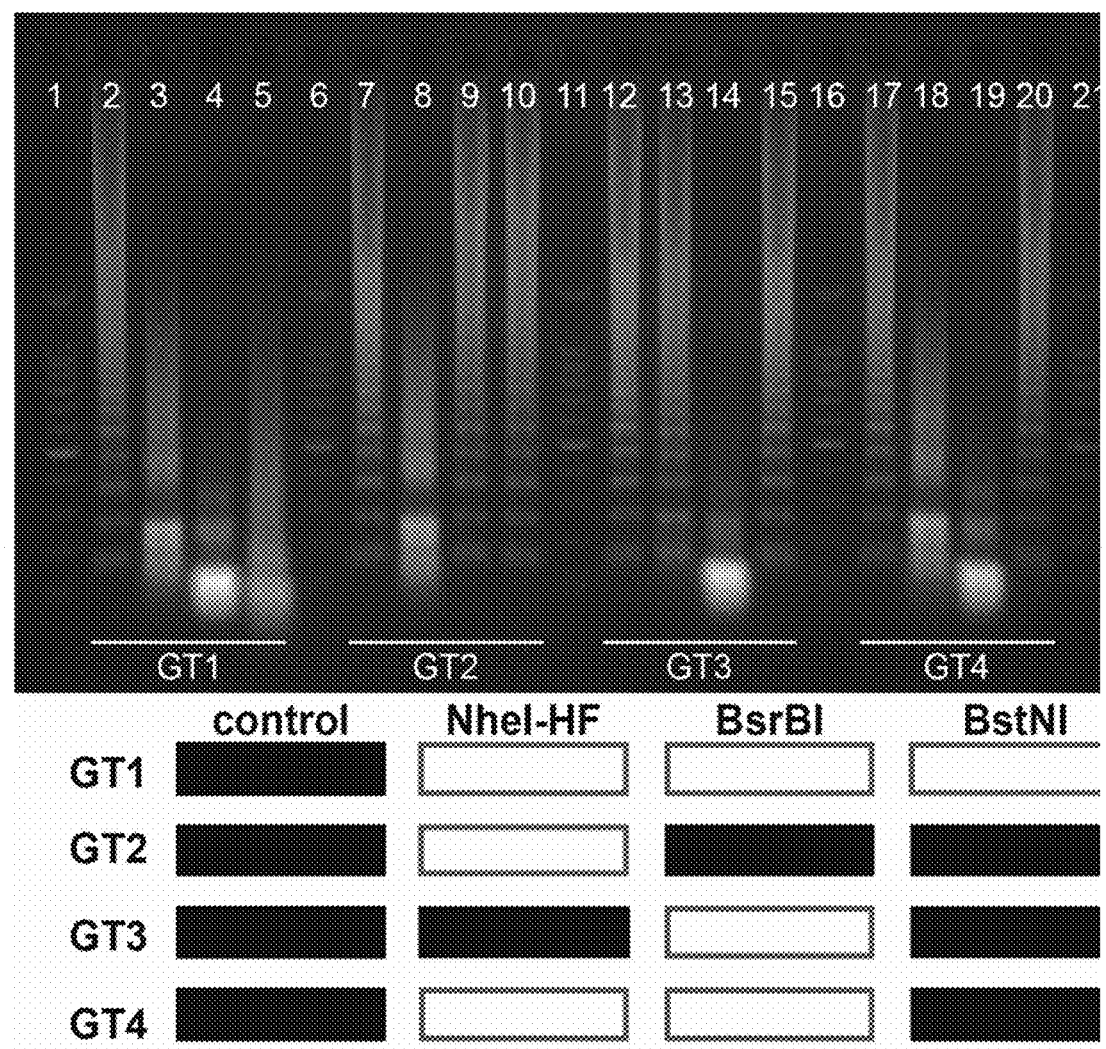
FIG. 29A shows exemplary experimental results in an electrophoresis gel for an amplification reaction assay with different restriction enzymes and genotypes.
FIG. 29B shows exemplary predicted results for an amplification reaction assay with different restriction enzymes and genotypes.

Based on consensus obtained by aligning sequences of each genotype obtained from Los Alamos National Laboratory (LANL), three restriction enzymes thermostable under RT-LAMP conditions were chosen to target the sequence differences between these four genotypes within the RT-LAMP amplicon. NheI-HF (targeting GCTAGC) should recognize genotypes 1, 2, and 4; BsrBI (targeting CCGCTC) should recognize genotypes 1, 3, and 4; and BstNI (targeting CCWGG) should recognize only GT1. These predictions are illustrated schematically in FIG. 28A, where black boxes represent predicted positive signal (amplification) and empty boxes represent predicted negative signal (inhibition). In FIG. 28, the first column in both sections represents the positive control in the absence of restriction enzyme and the following three columns indicate experiments with different restriction enzymes; each row represents a genotype (GT) of HCV RNA. Under LAMP conditions, these three enzymes remained active and sequence specific, as shown in FIG. 29A with gel electrophoresis and represented schematically in FIG. 29B. In FIG. 29A, lanes 1, 6, 11, 16 and 21 are 100 bp DNA ladders; lanes 2-5 are positive control, NheI-HF digestion product, BsrBI digestion product, and BstNI digestion product for genotype 1, respectively; lanes 7-10 are positive control and 3 restriction enzyme digestion products for genotype 2; lanes 12-15 are for genotype 3; and lanes 17-20 for genotype 4. The specificity of restriction enzyme to different genotypes are the same as predicted in FIG. 28A: for genotype 1, all 3 restriction enzymes digested the product; for genotype 2 only NheI-HF digested the product; for genotype 3 only BsrBI digested the product, and for genotype 4 both NheI-HF and BsrBI digested the product.

Figure 30A:
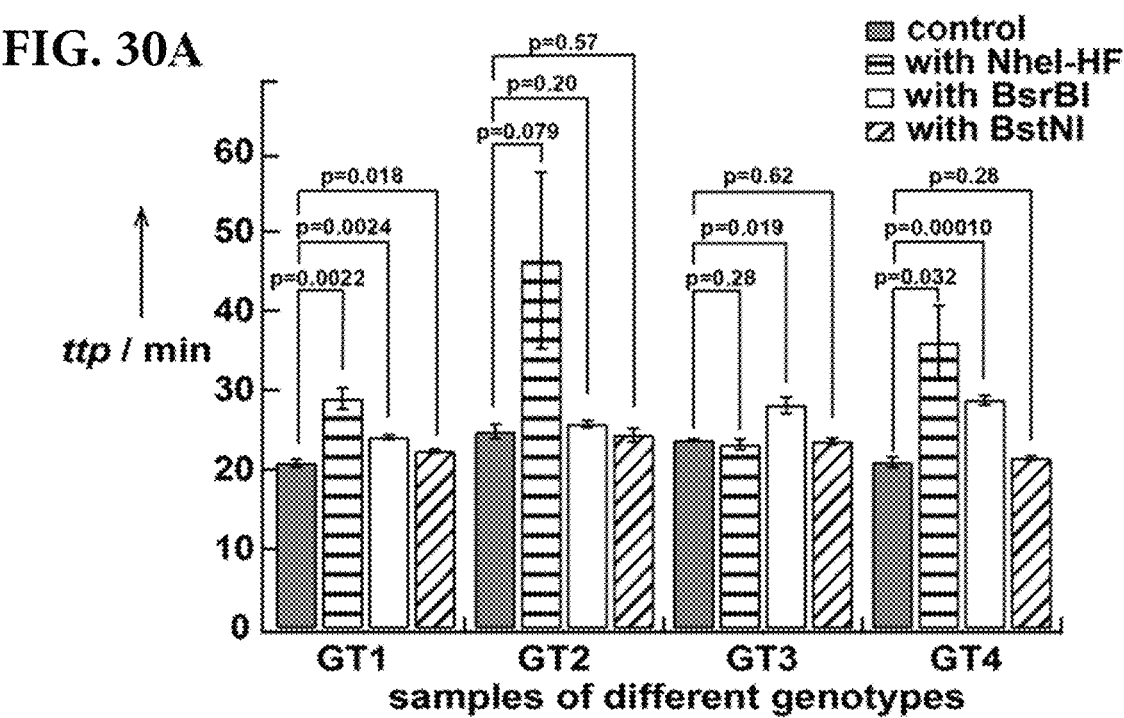
FIG. 30A shows exemplary results from a real-time bulk format HCV genotyping assay.
Figure 30B:
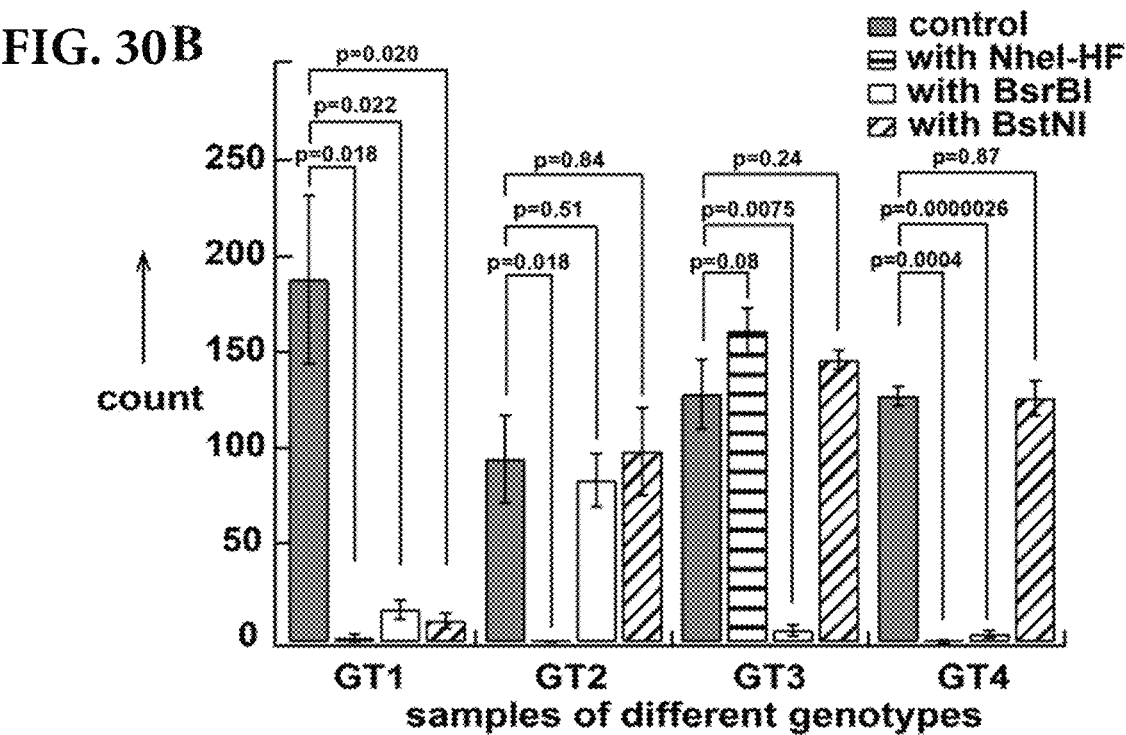
FIG. 30B shows exemplary results from a digital format HCV genotyping assay.
Figure 31A:
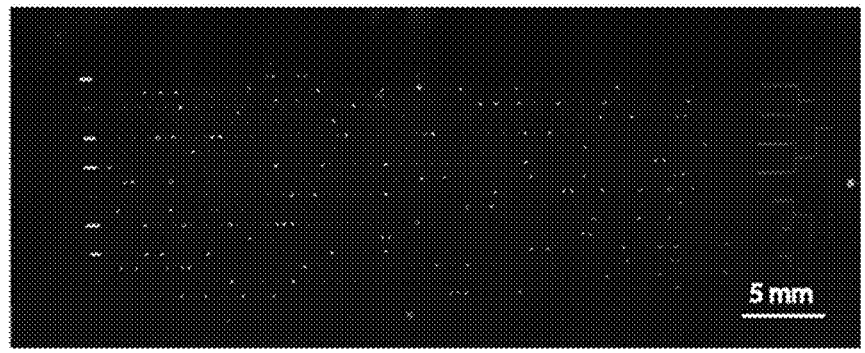
FIG. 31A shows exemplary results from a digital format HCV genotyping assay for genotype 3 without a restriction enzyme, conducted on a SlipChip device.
Figure 31B:
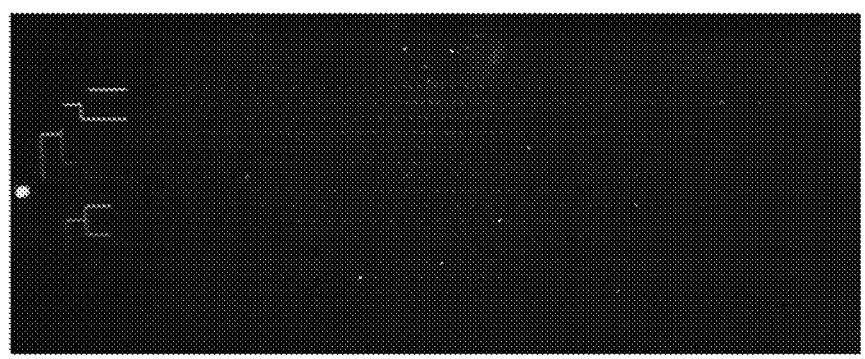
FIG. 31B shows exemplary results from a digital format HCV genotyping assay for genotype 3 with BsrBI, conducted on a SlipChip device.
Figure 31C:
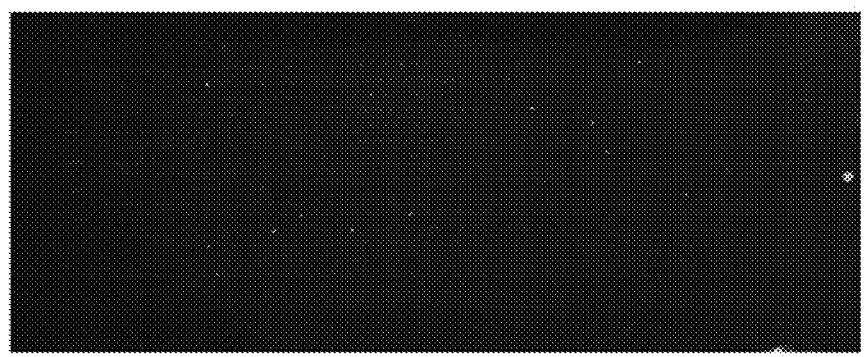
FIG. 31C shows exemplary results from a digital format HCV genotyping assay for genotype 1 with BsrBI, conducted on a SlipChip device.
Figure 31D:
FIG. 31D shows exemplary results from a digital format HCV genotyping assay for genotype 3 with BstNI, conducted on a SlipChip device.

For each genotype, four digital experiments were performed: one positive control without restriction enzymes, and three experiments with one restriction enzyme each. The positive control also provided a measurement of the viral load and validation for performing digital experiments, with results shown in Table 15. The experimental results (FIG. 28B) agreed with the inhibition pattern predicted (FIG. 28A) Amplification of GT1 was inhibited by all three restriction enzymes; amplification of GT2 was inhibited by NheI-HF only; amplification of GT3 was inhibited by BsrBI; and amplification of GT4 was inhibited by NheI-HF and BsrBI. The fate of molecules for each combination was dependent somewhat on the restriction enzyme being used, but in all cases the inhibition was strong and statistically significant (FIG. 30B).

TABLE 15

Statistical analysis of digital counts obtained in positive controls for RT-LAMP of different HCV genotypes. Distribution of numbers of amplifiable RNA molecules in wells calculated based on observed digital counts and Poisson statistics.

| HCV RNA | GT1 | GT2 | GT3 | GT4 |
|---|---|---|---|---|
| Average counts | 190 | 96 | 130 | 129 |
| Standard deviation | 44 | 23 | 18 | 5 |
| Poisson estimate of zero amplifiable molecules per well | 1090 | 1184 | 1150 | 1151 |
| Poisson estimate of one amplifiable molecule per well | 175 | 92 | 123 | 122 |
| Poisson estimate of two amplifiable molecules per well | 14 | 4 | 7 | 6 |
| Poisson estimate of three amplifiable molecules per well | 1 | 0 | 0 | 0 |
| Poisson estimate of average amplifiable molecules per well | 0.16 | 0.078 | 0.11 | 0.11 |

The performance of this HCV genotyping approach in a real-time bulk format (FIG. 30A) was then compared to that in a digital format (FIG. 30B). Experimental repeats were performed on different days to ensure these experiments were not merely technical replicates. Both formats agreed with the prediction shown in FIG. 24A. In the digital format (FIG. 30B), reactions with restriction enzymes specific to the genotype showed counts reduced by at least 10 fold, giving statistically significant results (p<0.022). In the bulk format (FIG. 30A), reactions with restriction enzymes that are specific to the genotype were all delayed by a certain amount of time ranging from 2 min (~10% relative to time-to-positive of positive control) to 20 min (~100% relative to time-to-positive of positive control). Acceptable p-values were obtained for three of the four genotypes (p=0.079 for GT2 and p<0.032 for others). As the strength of inhibition by the restriction enzyme increased, (e.g., NheI-HF in FIG. 30B), in digital, lower counts and smaller p-values were observed.

Results from the SlipChip device were also imaged on a cell phone, as shown in FIG. 31. Positive wells were clearly distinguished from negative wells, indicating the compatibility of this assay with cell phone imaging. The combinations of RNA genotypes and REs are GT3 without restriction enzyme (FIG. 31A), GT3 with BsrBI (FIG. 31B); GT1 with BsrBI (FIG. 31C); and GT3 with BstNI (FIG. 31D).

Details for conducting experiments as described in Example 9 are as follows: All solvents and salts purchased from commercial sources were used as received unless otherwise stated. The Loopamp® RNA amplification kit and the Loopamp® Fluorescent Detection Reagent kit were purchased from SA Scientific (San Antonio, Tex., USA). The LoopAmp® RNA amplification kit contains 2× Reaction Mix (RM) (40 mM Tris-HCl pH 8.8, 20 mM KCl, 16 mM MgSO4, 20 mM (NH4)2SO4, 0.2% Tween20, 1.6 M Betaine and dNTPs 2.8 mM each), Enzyme Mix (EM) (mixture of Bst DNA polymerase and AMV reverse transcriptase), and distilled water (DW). Loopamp® Fluorescent Detection Reagent kit contains Fluorescent Detection Reagent (FD) (including calcein). SsoFast EvaGreen Supermix (2×) was purchased from Bio-Rad Laboratories (Hercules, Calif.). Bovine serum albumin (BSA) was purchased from Roche Diagnostics (Indianapolis, Ind.). All restriction enzymes were purchased from New England Biolabs (Ipswich, Mass.). All primers were ordered from Integrated DNA Technologies (Coralville, Iowa). Mineral oil (DNase, RNase, and Protease free), tetradecane, and DEPC-treated nuclease-free water were purchased from Fisher Scientific (Hanover Park, Ill.). Dichlorodimethylsilane was purchased from Sigma-Aldrich (St. Louis, Mo.). AcroMetrix® HCV-s panel and AcroMetrix® HCV High Control and EXPRESS One-Step SYBR GreenER Universal were purchased from Life Technologies (Grand Island, N.Y.). Genotype 3 and genotype 4 HCV viral isolates were purchased from Sera-Care Life Sciences (Gaithersburg, Md.). Nucleic acid extraction kit QIAamp Viral RNA Mini kit was purchased from QIAGEN (Inc, Valencia, Calif., USA) PCR Mastercycler and in situ adapter were purchased from Eppendorf (Hamburg, Germany) Eco real-time PCR system was purchased from Illumina, Inc. (San Diego, Calif.). Photomasks were designed in AutoCAD 2013 and ordered from CAD/Art Services, Inc. (Bandon, Oreg.). Soda-lime glass plates coated with layers of chromium and photoresist were ordered from the Telic Company (Valencia, Calif.). Sanger sequencing service was provided by Laragen, Inc. HCV sequences were extracted from Los Alamos database and aligned with Geneious software.

4 different HCV genotypes were assayed. Genotypes 1 and 2 were purchased from Acrometrix Corporation (Benicia, Calif., USA) and genotypes 3 and 4 from SeraCare Life Sciences (Milford, Mass., USA). Genotype and viral load information was provided by these companies: viral load of $2.5 \times 10^7$ IU/mL for GT1, $1.1 \times 10^6$-$3.4 \times 10^6$ IU/mL for GT2, $5.7 \times 10^6$ IU/mL for GT3, and $4.97 \times 10^6$ IU/mL for GT4. The genotype information was also provided by the companies and we confirmed the genotype by sequencing and phylogenetic analysis. The presence of targeted single-nucleotide polymorphisms or SNPs (restriction enzyme cutting sites) was confirmed by manual inspection of the sequencing chromatograms. RNA was extracted using the QIAamp Viral RNA Mini Kit (QIAGEN Inc, Valencia, Calif., USA) according to the manufacturer's instructions, using 200 µL of plasma and eluting the resulting nucleic acid extraction in 60 µL of elution buffer. Nucleic acid extractions were analyzed immediately or stored at −80° C. until further analysis. To amplify HCV viral RNA, the RT-PCR mix contained the following: 20 µL of 2× SsoFast Evagreen SuperMix, 1 µL of EXPRESS SYBR GreenER RT module, 1 µL of each primer (10 µM), 2 µL of template, and enough nuclease-free water to bring the volume to 40 µL. The reverse transcription was carried out at 50° C. for 15 min, followed by 2 min of reaction termination at 95° C. The amplification step was performed by 40 cycles of the following conditions: 95° C. for 15 seconds, 55° C. for 1 min and 72° C. for 1 min. The dendogram was constructed by alignment of the 222 nucleotide sequences within the 5'UTR region of HCV based on the UPGMA method under the Tamura-Nei model (bootstrap=1,000 replicates). Reference sequences from HCV strains (genotypes 1 to 4) were obtained from the Los Alamos HCV database. To amplify HCV viral RNA using RT-LAMP on a real-time PCR machine, the RT-LAMP mix contained the following: 20 µL of 2× reaction mix (RM), 2 µL of enzyme mix (EM), 1 µL of fluorescent detection reagent (FD), 4 µL of primer mixture (20 µM BIP/FIP, 10 µM LB/LF, and 2.5 µM B3/F3), various amounts of RNA template solution (2.86 µL GT1 RNA for FIG. 3, 2 µL 10-fold diluted GT1 RNA and 2 µL RNA for all the other genotypes for FIGS. 4 and 5), and enough nuclease-free water to bring the volume to 40 µL. The solution was split into 10 µL each and loaded into 3 wells on the Eco real-time PCR plate and heated at 63° C. for 50 min. RT-LAMP reagents and FD were used as purchased from SA Scientific and used as it was. To amplify HCV viral RNA using RT-LAMP in the presence of RE on real-time PCR machine, the RT-LAMP mix contained the following: 20 µL of RM, 2 µL of EM, 1 µL of FD, 4 µL of primer mixture (20 µM BIP/FIP, 10 µM LB/LF, and 2.5 µM B3/F3), various amounts of RNA template solution (2.86 µL GT1 RNA for FIG. 3, 2 µL 10-fold diluted GT1 RNA and 2 µL RNA for all the other genotypes for FIGS. 4 and 5), 4 µL 20-fold diluted RE (to make a 200-fold dilution in the final solution) and enough nuclease-free water to bring the volume to 40 µL. RE was diluted in nuclease-free water before immediately mixed with RT-LAMP reagents, and fresh dilution was made each time. The solution was split into 10 µL each and loaded into 3 wells on the Eco real-time PCR plate and heated at 63° C. for 50 min Bulk RT-LAMP/RE assays were carried out in an Eco Real-Time PCR System (Illumina, SD, USA) and data analysis was performed using Eco Real-Time PCR System Software (version 4.0). To determine the time-to-positive (time required for the fluorescent signal to cross the threshold), fluorescence intensity between 5 min and 15 min was used as the baseline and the threshold value was set to be half height of the maximum intensity. For the single-volume 1280-well SlipChip, all features were etched to a depth of 55 µm in soda lime glass to make the volume of loading well equal to 3 nL. To amplify HCV viral RNA using RT-LAMP method on real-time PCR machine, the RT-LAMP mix contained the following: 20 µL of RM, 2 µL of EM, 1 µL of FD, 4 µL of primer mixture (20 µM BIP/FIP, 10 µM LB/LF, and 2.5 µM B3/F3), 2 µL of BSA (20 mg/mL), various amounts of RNA template solution (2.86 µL GT1 RNA for FIG. 3, 2 µL 10-fold diluted GT1 RNA and 2 µL RNA for all the other genotypes for FIGS. 4 and 5), 4 µL diluted RE if not for positive control, and enough nuclease-free water to bring the volume to 40 µL. The solution was loaded onto SlipChip and heated at 63° C. for 50 min on a custom-built real-time instrument. RT-LAMP reagents and FD were used as purchased from SA Scientific. BSA was used as purchased from Roche Diagnostics. Experiments were performed on a Bio-Rad PTC-200 thermocycler with a custom machined block. The block contains a flat 3"×3" portion onto which the devices are placed ensuring optimal thermal contact. The excitation light source used was a Philips Luxeon S (LXS8-PW30) 1315 lumen LED module with a Semrock filter (FF02-475). Image Acquisition was performed with a VX-29MG camera and a Zeiss Macro Planar T F2-100 mm lens. A Semrock filter (FF01-540) was used as an emission filter. Images acquired were analyzed using self-developed Labview software. The data were analyzed by first creating a binary mask that defined the location of each reaction volume within the image. The masked spots were then overlaid on the stack of images collected over the course of the experiment and the average intensity of each individual masked spot was tracked over the course of the stack. Background subtraction of the real-time trace was performed by creating a least mean square fit of each individual trace. Threshold was then manually set at the half height of the averaged maximum intensity, and the time-to-positive of each reaction was then determined as the point at which the real-time curve crossed the defined threshold. Cell phone imaging white balance was set to automatic, the ISO was set at 800, the exposure value was set at +2, the focus mode was set to "close-up", and the resolution was adjusted to 8 MP. To test the specificity and activity of RE at the condition for RT-LAMP, we first prepared RT-LAMP product from HCV RNA of genotype 1, 2, 3, and 4, respectively. The amplification procedure was the same as described in above except that an additional 5 min at 85° C. was used to inactivate the polymerase. 2 μL RT-LAMP product was mixed with 4 μL fresh RM, 3 μL nuclease-free water and 1 μL RE (or water for non-RE control) and incubated at 63° C. for 30 min. The digestion product was analyzed on 1.2% agarose DNA gel stained with ethidium bromide at 75 Volt for 40 min. To determine the restriction enzyme concentration which did not trigger ab initio synthesis within 50 min, three dilutions (100-fold, 200-fold and 300-fold dilution in the final mixture) of each RE were added to RT-LAMP mix containing the same components as in the genotyping assay with the exception of HCV RNA template that was replaced with nuclease-free water. RE was diluted in nuclease-free water before immediately mixed with RT-LAMP reagents, and fresh dilution was made each time. The solution was split into 10 μL each and loaded into 3 wells on the Eco real-time PCR plate and heated at 63° C. for 96 min High-complexity molecular tests such as commercially available HCV genotyping assays are not well suited for limited-resource settings: for example, hybridization assays (Roche LINEAR ARRAY Hepatitis C Virus Genotyping Test, Siemens VERSANT HCV Genotype 2.0 assay (LiPA)) and hybridization followed by electrochemical readout (GenMark eSensor) assays start with a PCR step, take from several hours up to one day, and require strict control of conditions; sequencing analysis is also slow and requires complex protocols and instrumentation (TRUGENE HCV Genotype Test). Automated real-time RT-PCR with Taqman probes (Abbott RealTime HCV Genotype II) is faster (~5 hrs) but is still too complex and as a kinetic measurement not sufficiently robust for limited-resource settings.

Example 10—Modified NASBA with Oligonucleotide Modulator

To amplify HCV viral RNA using a usual NASBA protocol on a real-time PCR machine without oligonucleotide modulator, the NASBA mix contained the following: 6.7 μL of 3× Reaction Buffer (NECB), 3.3 μL of the nucleotide mix (NECN), 1.2 μL of primer mixture (10 μM P1, 10 μM P2 and 10 μM DNA molecular beacon), various amounts of RNA template solution, and nuclease-free water (to bring the volume to 15 μL). This mixture was gently mixed and microcentrifuged for a few seconds, then P1 was annealed by heating for 2 min at 65° C. and cooling 10 min at 41° C. (pre-incubation step) Immediately after the annealing, 5 μL of enzyme mixture (NEC) was added to this mixture. The solution was loaded into two wells (9 μL each) of an Eco real-time PCR plate and incubated at 41° C. for 90 min while monitoring the fluorescent signal in one-minute intervals. NASBA reagents were purchased from Life Sciences Advanced Technologies.

To amplify HCV viral RNA using a modified NASBA method on a real-time PCR machine without oligonucleotide modulator, the NASBA mix contained the following: 6.7 μL of 3× Reaction Buffer (NECB), 3.3 μL of the nucleotide mix (NECN), 1.2 μL of primer mixture (10 μM P1, 10 μM P2 and 10 μM RNA molecular beacon), 0.6 μL of Hybridase Thermostable Rnase H various amount of RNA template solution, and enough nuclease-free water (to bring the volume to 15 μL). This mixture was gently mixed and microcentrifuged for a few seconds, then P1 was annealed by heating for 2 min at 65° C. and cooling 10 min at 41° C. (pre-incubation step). Immediately after the annealing 5 μL of enzyme mixture (NEC) was added to this mixture. The solution was loaded into two wells (9 μL each) of an Eco real-time PCR plate and heated at 41° C. for 90 min while monitoring the fluorescent signal in one-minute intervals. NASBA reagents were purchased from Life Sciences Advances Technologies and Hybridase Thermostable Rnase H was purchased from Epicentre.

To amplify HCV viral RNA using a modified NASBA method on a real-time PCR machine with oligonucleotide modulator, the NASBA mix contained the following: 6.7 μL of 3× Reaction Buffer (NECB), 3.3 μL of the nucleotide mix (NECN), 1.2 μL of primer mixture (10 μM P1, 10 μM P2 and 10 μM RNA molecular beacon), 0.5 μL of specific oligonucleotide modulator (10 μM), 0.6 μL of Hybridase Thermostable Rnase H various amount of RNA template solution, and enough nuclease-free water (to bring the volume to 15 μL). The mixture was gently mixed and microcentrifuged for a few seconds, then P1 was annealed by heating for 2 min at 65° C. and cooling 10 min at 41° C. (pre-incubation step) Immediately after the annealing 5 μL of enzyme mixture (NEC) was added to this mixture. The solution was loaded into two wells (9 μL each) of an Eco real-time PCR plate and heated at 41° C. for 90 min while monitoring the fluorescent signal in one-minute intervals. NASBA reagents were purchased from Life Sciences Advances Technologies and Hybridase Thermostable Rnase H was purchased from Epicentre.

Table 16 shows a comparison between a regular NASBA reaction and the modified NASBA reaction as discussed above. Table 17 shows real-time NASBA results with and without specific antisense oligonucleotide modulators targeting HCV RNA template. HCV Genotype 1 (GT1) without antisense oligonucleotide modulator showed a Cq of 26.54; HCV GT1 in the presence of specific GT1 oligonucleotide showed a Cq of 56.20, more than 20 min delay; HCV GT1 in the presence of specific GT2 oligonucleotide showed a Cq of 28.86, more than 2 min delay. Cq values are equivalent to 1.2 min.

TABLE 16

Regular NASBA reaction compared to the modified NASBA reaction.

| Reagent | regular NASBA | modified NASBA |
| --- | --- | --- |
| NASBA Enzyme Cocktail | 5.0 μL | 5.0 μL |
| 3X NASBA Reaction buffer | 6.7 μL | 6.7 μL |
| 6X Nucleotide Mix | 3.3 μL | 3.3 μL |
| RNase H (5 U/μL) | — | 0.6 μL |
| P1 (10 uM stock) | 0.4 μL | 0.4 μL |
| P2 (10 uM stock) | 0.4 μL | 0.4 μL |
| DNA molecular beacon (10 uM stock) | 0.4 μL | — |
| RNA molecular beacon (10 uM stock) | — | 0.4 μL |
| RNA | 2.5 μL | 2.5 μL |
| nuclease-free water | 1.3 μL | 0.7 μL |

TABLE 17

Specific inhibition with guide-RNAseH.

| Sample | Cq (SD) |
|---|---|
| HCV GT1 + RNAse H | 26.54 (0.40) |
| HCV GT1 + oligonucleotide modulator GT1 + RNase H | 56.20 (16.12) |
| HCV GT1 + oligonucleotide modulator GT2 + RNase H | 28.86 (1.10) |

FIG. 32 shows a comparison of NASBA reactions with DNA and RNA molecular beacon before and after addition of extra amount of RNase H. FIG. 32A shows the performance of a NASBA reaction using a DNA molecular beacon (dashed line) and RNA molecular beacon (solid line) with standard concentration of RNase H, as provided from a commercial company. FIG. 32B shows the performance of a NASBA reaction using a DNA molecular beacon (dashed line) and RNA molecular beacon (solid line) with increased concentration of RNase H. All 9 µL reactions contained approximately 1,000 genomic copies of hepatitis C virus GT1. Each experimental condition represents a mean from triplicate reactions. NASBA reactions with RNA molecular beacon were faster than reactions with DNA molecular beacon. In the presence of higher RNase H concentration and RNA molecular beacon efficiency of the reaction was improved, plateau was reached faster.

FIG. 33 shows results from a modified NASBA reaction. Modified NASBA as described in Table 16 was performed while varying the final concentration of RNA molecular beacon in the mixture. Triplicate reactions showed that the measured time to positive (FIG. 33A) was effected very slightly as the beacon concentration increased from 0.1 µM to 0.4 µM. In contrast, the endpoint fluorescent intensity of the molecular beacons (FIG. 33B) increased from 0.39 to 0.9.

Example 11—Restriction Enzyme (ApoI) Enhanced RNA NASBA

FIG. 34 shows results from experiments on the effect of preincubation on the time to positive of restriction enzyme (ApoI) enhanced RNA NASBA compared to regular NASBA. NASBA reagents were purchased from Life Sciences Advances Technologies. Restriction Enzyme ApoI was purchased from New England Biolabs, and experiments were conducted under the following conditions:

Pre-incubation+ApoI (FIG. 34A, first from left): NASBA mix containing the following: 6.7 µL of 3× Reaction Buffer (NECB), 3.3 µL of the nucleotide mix (NECN), 1.2 µL of primer mixture (10 µM P1, 10 µM P2 and 10 µM DNA molecular beacon), and 2 µL HCV RNA GT1 (final volume of 14 µL). The mixture was gently mixed and microcentrifuged for a few seconds, then P1 was annealed by heating for 2 min at 65° C. and cooling 10 min at 41° C. (pre-incubation step) Immediately after the annealing 5 µL of enzyme mixture (NEC)+1 µL of ApoI (5-fold diluted in water from original stock) were added to this mixture. The solution was loaded into two wells (9 µL each) of an Eco real-time PCR plate and heated at 41° C. for 90 min while monitoring the fluorescent signal in one-minute intervals;

Pre-incubation (FIG. 34A, second from left): NASBA mix containing the following: 6.7 µL of 3× Reaction Buffer (NECB), 3.3 µL of the nucleotide mix (NECN), 1.2 µL of primer mixture (10 µM P1, 10 µM P2 and 10 µM DNA molecular beacon), and 2 µL HCV RNA GT1 (final volume of 14 µL). The mixture was gently mixed and microcentrifuge for a few seconds, then P1 was annealed by heating for 2 min at 65° C. and cooling 10 min at 41° C. (pre-incubation step) Immediately after the annealing 5 µL of enzyme mixture (NEC)+1 µL of distilled water were added to this mixture. The solution was loaded into two wells (9 µL each) of an Eco real-time PCR plate and heated at 41° C. for 90 min while monitoring the fluorescent signal in one-minute intervals;

Ice+ApoI (FIG. 34A, third from left): NASBA mix containing the following: 6.7 µL of 3× Reaction Buffer (NECB), 3.3 µL of the nucleotide mix (NECN), 1.2 µL of primer mixture (10 µM P1, 10 µM P2 and 10 µM DNA molecular beacon), and 2 µL HCV RNA GT1 (final volume of 14 µL). The mixture was gently mixed and microcentrifuge for a few seconds and kept on ice for 12 min, time equivalent to pre-incubation Immediately after the annealing 5 µL of enzyme mixture (NEC)+1 µL of ApoI (5-fold diluted in water from original stock) were added to this mixture. The solution was loaded into two wells (9 µL each) of an Eco real-time PCR plate and heated at 41° C. for 90 min while monitoring the fluorescent signal in one-minute intervals;

Ice (FIG. 34A, fourth from left): NASBA mix containing the following: 6.7 µL of 3× Reaction Buffer (NECB), 3.3 µL of the nucleotide mix (NECN), 1.2 µL of primer mixture (10 µM P1, 10 µM P2 and 10 µM DNA molecular beacon), and 2 µL HCV RNA GT1 (final volume of 14 µL). The mixture was gently mixed and microcentrifuge for a few seconds and kept on ice for 12 min, time equivalent to pre-incubation Immediately after the annealing 5 µL of enzyme mixture (NEC)+1 µL of distilled water were added to this mixture. The solution was loaded into two wells (9 µL each) of an Eco real-time PCR plate and heated at 41° C. for 90 min while monitoring the fluorescent signal in one-minute intervals.

The time to positive was reduced by the same degree via the addition of ApoI and the inclusion of a pre-incubation step; including both further reduced the time to positive (FIG. 34A). FIG. 34B shows the effect of pre-incubation on the RNA product of restriction enzyme (ApoI) enhanced RNA NASBA reaction compared to regular NASBA as visualized by gel electrophoresis. When the reaction is performed without pre-incubation, nonspecific products dominate the visible reaction product. Including a pre-incubation step reduces this product to a single predominant band. In a similar manner, the addition of ApoI prevents the accumulation of nonspecific product, to a greater degree. Each experimental condition was run in duplicate.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method, comprising:
    providing a volume suspected of containing a target nucleic acid;
    dispersing said volume among a plurality of areas, such that said plurality of areas comprises a distribution of nucleic acids, and
    conducting an isothermal nucleic acid amplification reaction in said volume in the dispersed volume in said plurality of areas in presence of a modulator comprising an engineered or non-natural sequence-specific nuclease selected from the group consisting of zinc-finger nuclease, transcription activator-like effector nuclease, meganuclease and RNA-guided Cas9 nuclease, the engineered or non-natural sequence-specific nuclease cleaving said target nucleic acid within a region amplified by said isothermal nucleic acid amplification reaction.

2. The method of claim 1, wherein said distribution generates digital nucleic acid amplification signals.

3. The method of claim 2, wherein said plurality of areas each comprises at most one copy of said target nucleic acid.

4. The method of claim 2, further comprising prior to the conducting, providing the modulator to said plurality of areas.

5. The method of claim 1, wherein the providing comprises providing a first volume comprising a first nucleic acid and a second volume comprising a second nucleic acid, wherein the dispersing comprises dispersing said first volume among a plurality of first areas and dispersing said second volume among a plurality of second areas, and wherein the conducting is performed in the dispersed first volume in said plurality of first areas and in the dispersed second volume in said plurality of second areas.

6. The method of claim 5, wherein said plurality of first areas each comprise at most one copy of said first nucleic acid and said plurality of second areas each comprise at most one copy of said second nucleic acid.

7. The method of claim 5, further comprising prior to the conducting, providing the modulator to said plurality of first areas or to said plurality of second areas.

8. The method of claim 5, further comprising detecting a difference in said isothermal nucleic acid amplification reaction between said first nucleic acid and said second nucleic acid.

9. The method of claim 8, wherein said difference is diagnostic of the presence of the target nucleic acid within said first nucleic acid and said second nucleic acid.

10. The method of claim 1, wherein modulation by the modulator comprises producing a difference in amplification efficiency.

11. The method of claim 10, wherein the said distribution generates digital nucleic acid amplification signals, wherein said difference in amplification efficiency produces a positive amplification signal in a subset of said plurality of areas.

12. The method of claim 11, wherein said positive amplification signal in said subset of said plurality of areas is diagnostic of the presence of said target nucleic acid within said volume.

13. The method of claim 1, wherein the target nucleic acid comprises an HCV nucleic acid.

14. The method of claim 13, wherein said method generates a signal from which an HCV genotype can be determined.

15. The method of claim 1, further comprising comparing results of said isothermal nucleic acid amplification reaction to results of a control isothermal nucleic acid amplification reaction carried out in the absence of the modulator.

16. The method of claim 1, wherein said isothermal nucleic acid amplification reaction is selected from the group consisting of Recombinase Polymerase Amplification (RPA), Loop-mediated isothermal amplification (LAMP), Helicase-dependent amplification (HAD), Strand displacement amplification (SDA), Nucleic acid sequence based amplification (NASBA), and Nicking enzyme amplification reaction (NEAR).

17. The method of claim 16, wherein said isothermal nucleic acid amplification reaction is LAMP or NASBA.

18. The method of claim 1, wherein the modulator is RNA-guided Cas9 nuclease.

19. The method of claim 18, wherein the modulator further comprises a crRNA and a tracrRNA, the crRNA, tracRNA and Cas9 forming a Cas9-crRNA-tracrRNA complex.

* * * * *